(12) United States Patent
Gao et al.

(10) Patent No.: US 10,072,251 B2
(45) Date of Patent: Sep. 11, 2018

(54) RECOMBINANT AAVS HAVING USEFUL TRANSCYTOSIS PROPERTIES

(71) Applicant: University of Massachusetts, Boston, MA (US)

(72) Inventors: Guangping Gao, Westborough, MA (US); Li Zhong, Worcester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/120,294

(22) PCT Filed: Feb. 19, 2015

(86) PCT No.: PCT/US2015/016691
§ 371 (c)(1),
(2) Date: Aug. 19, 2016

(87) PCT Pub. No.: WO2015/127128
PCT Pub. Date: Aug. 27, 2015

(65) Prior Publication Data
US 2017/0191039 A1    Jul. 6, 2017

Related U.S. Application Data

(60) Provisional application No. 61/942,002, filed on Feb. 19, 2014.

(51) Int. Cl.
| | | |
|---|---|---|
| *C12N 15/113* | (2010.01) | |
| *C12N 7/00* | (2006.01) | |
| *C12N 15/86* | (2006.01) | |
| *A61K 48/00* | (2006.01) | |
| *A61K 38/17* | (2006.01) | |

(52) U.S. Cl.
CPC ............ *C12N 7/00* (2013.01); *A61K 38/1709* (2013.01); *A61K 48/0058* (2013.01); *C12N 15/113* (2013.01); *C12N 15/86* (2013.01); *C12N 2310/141* (2013.01); *C12N 2710/10332* (2013.01); *C12N 2710/10342* (2013.01); *C12N 2750/14143* (2013.01)

(58) Field of Classification Search
CPC .............. A61K 48/0058; C12N 15/113; C12N 15/8645; C12N 2710/10341; C12N 2750/14111; C12N 2750/14122; C12N 2750/14132; C12N 2750/14141; C12N 2750/14143

See application file for complete search history.

(56) References Cited

U.S. PATENT DOCUMENTS

| | | | |
|---|---|---|---|
| 5,478,745 A | 12/1995 | Samulski et al. | |
| 5,871,982 A | 2/1999 | Wilson et al. | |
| 6,251,677 B1 | 6/2001 | Wilson et al. | |
| 6,485,966 B2 | 11/2002 | Gao et al. | |
| 6,498,244 B1 | 12/2002 | Patel et al. | |
| 6,544,786 B1 | 4/2003 | Xiao et al. | |
| 6,953,690 B1 | 10/2005 | Gao et al. | |
| 6,962,815 B2 | 11/2005 | Bartlett | |
| 7,022,519 B2 | 4/2006 | Gao et al. | |
| 7,198,951 B2 | 4/2007 | Gao et al. | |
| 7,235,393 B2 | 6/2007 | Gao et al. | |
| 7,427,396 B2 | 9/2008 | Arbetman et al. | |
| 7,456,015 B2 | 11/2008 | Bohn et al. | |
| 7,906,111 B2 | 3/2011 | Wilson et al. | |
| 8,222,221 B2 | 7/2012 | Corey et al. | |
| 8,524,446 B2 | 9/2013 | Gao et al. | |
| 8,734,809 B2 | 5/2014 | Gao et al. | |
| 9,102,949 B2 | 8/2015 | Gao et al. | |
| 9,217,155 B2 | 12/2015 | Gao et al. | |
| 9,226,976 B2 | 1/2016 | Flotte et al. | |
| 9,272,053 B2 | 3/2016 | Gao et al. | |
| 9,284,357 B2 | 3/2016 | Gao et al. | |
| 2001/0016355 A1 | 8/2001 | Samulski et al. | |
| 2002/0164783 A1 | 11/2002 | Feldhaus | |
| 2003/0103939 A1 | 6/2003 | Engelhardt et al. | |
| 2003/0110526 A1 | 6/2003 | Brown et al. | |
| 2003/0138772 A1 | 7/2003 | Gao et al. | |
| 2004/0101514 A1 | 5/2004 | Liu et al. | |
| 2005/0014262 A1 | 1/2005 | Gao et al. | |
| 2005/0037988 A1 | 2/2005 | Zamore et al. | |
| 2005/0137153 A1 | 6/2005 | McSwiggen et al. | |
| 2005/0287122 A1 | 12/2005 | Bartlett et al. | |
| 2006/0063174 A1 | 3/2006 | Turner et al. | |

(Continued)

FOREIGN PATENT DOCUMENTS

| | | |
|---|---|---|
| WO | WO 2003/042397 | 5/2003 |
| WO | WO 2005/033321 | 4/2005 |

(Continued)

OTHER PUBLICATIONS

Adachi et al., Drawing a high-resolution functional map of adeno-associated virus capsid by massively parallel sequencing. Nat Commun. 2014;5:3075. doi: 10.1038/ncomms4075.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Arbuthnot et al., Hepatic delivery of RNA interference activators for therapeutic application. Curr. Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

(Continued)

*Primary Examiner* — Kevin Kai Hill
(74) *Attorney, Agent, or Firm* — Wolf, Greenfield & Sacks, P.C.

(57) ABSTRACT

The disclosure in some aspects relates to recombinant adeno-associated viruses having distinct tissue targeting capabilities. In some aspects, the disclosure relates to gene transfer methods using the recombinant adeno-associate viruses. In some aspects, the disclosure relates to isolated AAV capsid proteins and isolated nucleic acids encoding the same.

19 Claims, 28 Drawing Sheets

Specification includes a Sequence Listing.

(56) References Cited

U.S. PATENT DOCUMENTS

| | | | |
|---|---|---|---|
| 2006/0093589 | A1 | 5/2006 | Warrington et al. |
| 2006/0189564 | A1 | 8/2006 | Burright et al. |
| 2006/0292117 | A1 | 12/2006 | Loiler et al. |
| 2007/0036760 | A1 | 2/2007 | Wilson et al. |
| 2007/0243526 | A1 | 10/2007 | Kay et al. |
| 2008/0292595 | A1 | 11/2008 | Arbetman et al. |
| 2009/0042828 | A1 | 2/2009 | Xu et al. |
| 2009/0111766 | A1 | 4/2009 | Atkinson et al. |
| 2009/0149409 | A1 | 6/2009 | Bohn et al. |
| 2009/0197338 | A1 | 8/2009 | Vandenberghe et al. |
| 2010/0104561 | A1 | 4/2010 | Zhong et al. |
| 2010/0186103 | A1 | 7/2010 | Gao et al. |
| 2010/0323001 | A1 | 12/2010 | Pachuk |
| 2011/0171262 | A1 | 7/2011 | Bakker et al. |
| 2011/0172293 | A1 | 7/2011 | Fish et al. |
| 2011/0258716 | A1 | 10/2011 | Baltimore et al. |
| 2012/0137379 | A1* | 5/2012 | Gao ............... C07K 14/005 800/8 |
| 2012/0270930 | A1 | 10/2012 | Van Der Maarel et al. |
| 2012/0309050 | A1 | 12/2012 | Kumon et al. |
| 2013/0101558 | A1 | 4/2013 | Gao et al. |
| 2013/0109742 | A1 | 5/2013 | Hewitt et al. |
| 2013/0195801 | A1 | 8/2013 | Gao et al. |
| 2013/0281516 | A1 | 10/2013 | Gao et al. |
| 2014/0142161 | A1 | 5/2014 | Flotte et al. |
| 2014/0142288 | A1 | 5/2014 | Davidson et al. |
| 2014/0179770 | A1 | 6/2014 | Zhang et al. |
| 2014/0296486 | A1 | 10/2014 | Gao et al. |
| 2014/0335054 | A1 | 11/2014 | Gao et al. |
| 2016/0208257 | A1 | 1/2016 | Gao et al. |
| 2016/0135438 | A1 | 5/2016 | Gao et al. |
| 2016/0186211 | A1 | 6/2016 | Flotte et al. |

FOREIGN PATENT DOCUMENTS

| | | |
|---|---|---|
| WO | WO 2006/031267 A2 | 3/2006 |
| WO | WO 2006/119432 A2 | 11/2006 |
| WO | WO 2007/000668 A2 | 1/2007 |
| WO | WO 2007/027775 A2 | 3/2007 |
| WO | WO 2008/091703 | 7/2008 |
| WO | WO 2008/147839 A1 | 12/2008 |
| WO | WO 2008/150897 A2 | 12/2008 |
| WO | WO 2009/109665 A1 | 9/2009 |
| WO | WO 2009/146178 A1 | 12/2009 |
| WO | WO 2010/027446 A2 | 3/2010 |
| WO | WO 2010/034314 A1 | 4/2010 |
| WO | WO 2010/071454 A1 | 6/2010 |
| WO | WO 2010/129021 A1 | 11/2010 |
| WO | WO 2010/138263 A2 | 12/2010 |
| WO | WO 2013/170078 A1 | 11/2013 |
| WO | WO 2013/190059 A1 | 12/2013 |
| WO | WO 2014/160092 A1 | 10/2014 |
| WO | WO 2014/186746 A1 | 11/2014 |
| WO | WO 2014/197748 A2 | 11/2014 |

OTHER PUBLICATIONS

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Brown et al., A microRNA-regulated lentiviral vector mediates stable correction of hemophilia B mice. Blood. Dec. 15, 2007;110(13):4144-52. Epub Aug. 28, 2007.

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006;12(5):585-91. Epub Apr. 23, 2006.

Buning et al., Receptor targeting of adeno-associated virus vectors. Gene Ther. Jul. 2003;10(14):1142-51.

Bussing et al., let-7 microRNAs in development, stem cells and cancer. Trends Mol Med. Sep. 2008;14(9):400-9. doi: 10.1016/j.molmed.2008.07.001. Epub Jul. 31, 2008.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.

Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.

Chen et al., Unique molecular signatures of disease brain endothelia provide new sites for CNS-directed enzyme therapy. Nat Med. Oct. 2009;15(10):1215-8. doi: 10.1038/nm.2025. Epub Sep. 13, 2009.

Chen et al., Regulation of immune responses and tolerance: the microRNA perspective. Immunol Rev. May 2013;253(1):112-28. doi:10.1111/imr.12060.

Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.

Cideciyan et al., Human RPE65 gene therapy for Leber congenital amaurosis: persistence of early visual improvements and safety at 1 year. Hum Gene Ther. Sep. 2009;20(9):999-1004.

Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.

Conlon et al., Ribozyme Approaches towards Down-Regulation of Pi*Z Mutant Human a-1 Anti-Trypsin. Mol. Therapy. 2004;9:5333. Abstract 875.

Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.

Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.

Cruz et al., The promise of gene therapy for the treatment of alpha-1 antitrypsin deficiency. Pharmacogenomics. Sep. 2007;8(9):1191-8.

Czech, MicroRNAs as therapeutic targets. N. Engl J Med. Mar. 16, 2006;354(11):1194-5.

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.

Daya et al., Gene therapy using adeno-associated virus vectors. Clin Microbiol Rev. Oct. 2008;21(4):583-93. doi: 10.1128/CMR.00008-08.

(56) References Cited

OTHER PUBLICATIONS

Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Ebert et al., MicroRNA sponges: competitive inhibitors of small RNAs in mammalian cells. Nat Methods. Sep. 2007;4(9):721-6. Epub Aug. 12, 2007.
Elmén et al., LNA-mediated microRNA silencing in non-human primates. Nature. Apr. 1, 2008;452(17): 896-900.
Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.
Esau et al., miR-122 regulation of lipid metabolism revealed by in vivo antisense targeting. Cell Metab. Feb. 2006;3(2):87-98.
Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.
Foust et al., Intravascular AAV9 preferentially targets neonatal-neurons and adult-astrocytes. Nature Biotechnology, 27; 59-65 2009.
Foust et al., Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
Genbank Submission; Accession No. ADZ26851; Wilson et al.; Jun. 30, 2005.
Genbank Submission; Accession No. AF028705.1; Rutledge et al.; Jan. 12, 1998.
Genbank Submission; NCBI, Accession No. AAB95450; Rutledge et al.; Jan. 12, 1998.
Genbank Submission; NCBI, Accession No. AAS99264; Gao et al.; Jun. 24, 2004.
Genbank Submission; NCBI, Accession No. ABA71701; Schmidt et al.; May 10, 2006.
Genbank Submission; NCBI, Accession No. ACB55301; Vandenberghe et al.; Jul. 31, 2008.
Genbank Submission; NCBI, Accession No. ACB55310; Vandenberghe et al.; Jul. 31, 2008.
Genbank Submission; NCBI, Accession No. NP_049542; Xiao et al.; Mar. 11, 2010.
Genbank Submission; NCBI, Accession No. YP_680426; Ruffing et al.; Nov. 19, 2010.
Gentner et al., Stable knockdown of microRNA in vivo by lentiviral vectors. Nat Methods. Jan. 2009;6(1):63-6. doi: 10.1038/nmeth.1277. Epub Nov. 30, 2008.
Girard et al., miR-122, a paradigm for the role of microRNAs in the liver. J Hepatol. Apr. 2008;48(4):648-56. doi: 10.1016/j.jhep.2008.01.019. Epub Feb. 12, 2008.
Gramantieri et al., Cyclin G1 is a target of miR-122a, a microRNA frequently down-regulated in human hepatocellular carcinoma. Cancer Res. Jul. 1, 2007;67(13):6092-9.
Grimm et al., Fatality in mice due to oversaturation of cellular microRNA/short hairpin RNA pathways. Nature. May 25, 2006;441(7092):537-41.
Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.
Haussecker et al., miR-122 continues to blaze the trail for microRNA therapeutics. Mol Ther. Feb. 2010;18(2):240-2. doi: 10.1038/mt.2009.313.
Hernandez et al., Latent adeno-associated virus infection elicits humoral but not cell-mediated immune responses in a nonhuman primate model. J Virol. Oct. 1999;73(10):8549-58.
Horwich et al., Design and delivery of antisense oligonucleotides to block microRNA function in cultured *Drosophila* and human cells. Nat Protoc. 2008;3(10):1537-49. doi: 10.1038/nprot.2008.145.
Hutvágner et al., Sequence-specific inhibition of small RNA function. PLoS Biol. Apr. 2004;2(4):E98. Epub Feb. 24, 2004.
Johnson et al., RAS is regulated by the let-7 microRNA family. Cell. Mar. 11, 2005;120(5):635-47.
Kota et al., AAV8-Mediated Delivery of miR-26a inhibits cancer cell proliferation and induces tumor-specific apoptosis in a liver cancer model. Mol. Therapy. May 2009. 17(1):5300. Abstract 783.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Krützfeldt et al., Silencing of microRNAs in vivo with 'antagomirs'. Nature. Dec. 1, 2005;438(7068):685-9. Epub Oct. 30, 2005.
Kutay et al., Downregulation of miR-122 in the rodent and human hepatocellular carcinomas. J Cell Biochem. Oct. 15, 2006;99(3):671-8.
Lanford et al., Therapeutic silencing of microRNA-122 in primates with chronic hepatitis C virus infection. Science. Jan. 8, 2010;327(5962):198-201. Epub Dec. 3, 2009.
Lewis et al., Conserved seed pairing, often flanked by adenosines, indicates that thousands of human genes are microRNA targets. Cell. Jan. 14, 2005;120(1):15-20.
Lewis et al., Prediction of mammalian microRNA targets. Cell. Dec. 26, 2003;115(7):787-98.
Li et al., Intronic microRNA: discovery and biological implications. DNA Cell Biol. Apr. 2007;26(4):195-207.
Li et al., Protein trans-splicing as a means for viral vector-mediated in vivo gene therapy. Hum Gene Ther. Sep. 2008;19(9):958-64. doi: 10.1089/hum.2008.009.

(56) References Cited

OTHER PUBLICATIONS

Lin et al., Impact of preexisting vector immunity on the efficacy of adeno-associated virus-based HIV-1 Gag vaccines. Hum Gene Ther. Jul. 2008;19(7):663-9.
Lowenstein, Crossing the rubicon. Nat Biotechnol. Jan. 2009;27(1):42-4.
Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.
Lux et al., Green fluorescent protein-tagged adeno-associated virus particles allow the study of cytosolic and nuclear trafficking. J Virol. Sep. 2005;79(18):11776-87.
Lynn, Meta-regulation: microRNA regulation of glucose and lipid metabolism. Trends Endocrinol Metab. Nov. 2009;20(9):452-9. doi: 10.1016/j.tem.2009.05.007. Epub Sep. 30, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Maguire et al., Directed evolution of adeno-associated virus for glioma cell transduction. J Neurooncol. Feb. 2010;96(3):337-47. doi:10.1007/s11060-009-9972-7. Epub Jul. 19, 2009.
Manfredsson et al., AAV9: a potential blood-brain barrier buster. Mol Ther. Mar. 2009;17(3):403-5.
Matalon et al., Adeno-associated virus-mediated aspartoacylase gene transfer to the brain of knockout mouse for canavan disease. Mol Ther. May 2003;7(5 Pt 1):580-7.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
Meister et al., Sequence-specific inhibition of microRNA- and siRNA-induced RNA silencing. RNA. Mar. 2004;10(3):544-50.
Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Schnepp et al., Characterization of adeno-associated virus genomes isolated from human tissues. J Virol. Dec. 2005;79(23):14793-803.
Sen et al., Micromanaging vascular biology: tiny microRNAs play big band. J Vasc Res. 2009;46(6):527-40. doi: 10.1159/000226221. Epub Jun. 30, 2009.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Vermeulen et al., Double-stranded regions are essential design components of potent inhibitors of RISC function. RNA. May 2007;13(5):723-30. Epub Mar. 30, 2007.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., MicroRNA regulated tissue specific transduction by rAAV vector. Molecular Therapy. May 2009;17(1): S279. Abstract 732.
Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.
Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): S140. Abstract 362.
Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.
Yu et al., let-7 regulates self renewal and tumorigenicity of breast cancer cells. Cell. Dec. 14, 2007;131(6):1109-23.
Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.

(56) References Cited

OTHER PUBLICATIONS

Zhong et al., Chimpanzee-derived novel natural variants of aav9: vector development and interrogation of correlations between capsid structure and vector biology. Molecular Therapy. May 2010;18(1): S24. Abstract 58.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2):158-67.

\* cited by examiner

FIG. 1

```
                                                                                    Section 6
         (356)  356        370        380        390        400        410        426
AAV9     (356) LGSAHEGCLPPFPADVFMIPQYGYLTLNDGSQAVGRSSFYCLEYFPSQMLRTGNNFQFSYEFENVPFHSSY
CLvD8    (356) LGSAHEGCLPPFPADVFMIPQYGYLTLNDGSQAVGRSSFYCLEYFPSQMLRTGNNFQFSYEFENVPFHSSY
AAV9Y    (356) LGSAHEGCLPPFPADVFMIPQYGYLTLNDGSQAVGRSSFYCLEYFPSQMLRTGNNFQFSYEFENVPFHSSY
AAV9H    (356) LGSAHEGCLPPFPADVFMIPQYGYLTLNDGSQAVGRSSFYCLEYFPSQMLRTGNNFQFSYEFENVPFHSSY
AAV9R    (356) LGSAHEGCLPPFPADVFMIPQYGYLTLNDGSQAVGRSSFYCLEYFPSQMLRTGNNFQFSYEFENVPFHSSY
AAV9I    (356) LGSAHEGCLPPFPADVFMIPQYGYLTLNDGSQAVGRSSFYCLEYFPSQMLRTGNNFQFSYEFENVPFHSSY
AAVHR    (356) LGSAHEGCLPPFPADVFMIPQYGYLTLNDGSQAVGRSSFYCLEYFPSQMLRTGNNFQFSYEFENVPFHSSY
Consensus (356) LGSAHEGCLPPFPADVFMIPQYGYLTLNDGSQAVGRSSFYCLEYFPSQMLRTGNNFQFSYEFENVPFHSSY Section 7
         (427)  427        440        450        460        470        480        497
AAV9     (427) AHSQSLDRLMNPLIDQYLYYLSKTINGSGQNQQTLKFSVAGPSNMAVQGRNYIPGPSYRQQRVSTTVTQNN
CLvD8    (427) AHSQSLDRLMNPLIDQYLYYLSKTINGSGQNQQTLKFSVAGPSNMAVQGRNYIPGPSYRQQRVSTTVTQNN
AAV9Y    (427) AHSQSLDRLMNPLIDQYLYYLSKTINGSGQNQQTLKFSVAGPSNMAVQGRNYIPGPSYRQQRVSTTVTQNN
AAV9H    (427) AHSQSLDRLMNPLIDQYLYYLSKTINGSGQNQQTLKFSVAGPSNMAVQGRNYIPGPSYRQQRVSTTVTQNN
AAV9R    (427) AHSQSLDRLMNPLIDQYLYYLSKTINGSGQNQQTLKFSVAGPSNMAVQGRNYIPGPSYRQQRVSTTVTQNN
AAV9I    (427) AHSQSLDRLMNPLIDQYLYYLSKTINGSGQNQQTLKFSVAGPSNMAVQGRNYIPGPSYRQQRVSTTVTQNN
AAVHR    (427) AHSQSLDRLMNPLIDQYLYYLSKTINGSGQNQQTLKFSVAGPSNMAVQGRNYIPGPSYRQQRVSTTVTQNN
Consensus (427) AHSQSLDRLMNPLIDQYLYYLSKTINGSGQNQQTLKFSVAGPSNMAVQGRNYIPGPSYRQQRVSTTVTQNN Section 8
         (498)  498        510        520        530        540        550        568
AAV9     (498) NSEFAWPGASSWALNGRNSLMNPGPAMASHKEGEDRFFPLSGSLIFGKQGTGRDNVDADKVMITNEEEIKT
CLvD8    (498) NSEFAWPGASSWALNGRNSLMNPGPAMASHKEGEDSFFPLSGSLIFGKQGTGRDNVDADKVMITNEEEIKT
AAV9Y    (498) NSEFAWPGASSWALNGRNSLMNPGPAMASHKEGEDRFFPLSGSLIFGKQGTGRDNVDADKVMITNEEEIKT
AAV9H    (498) NSEFAWPGASSWALNGRNSLMNPGPAMASHKEGEDRFFPLSGSLIFGKQGTGRDNVDADKVMITNEEEIKT
AAV9R    (498) NSEFAWPGASSWALNGRNSLMNPGPAMASHKEGEDRFFPLSGSLIFGKQGTGRDNVDADKVMITNEEEIKT
AAV9I    (498) NSEFAWPGASSWALNGRNSLMNPGPAMASHKEGEDRFFPLSGSLIFGKQGTGRDNVDADKVMITNEEEIKT
AAVHR    (498) NSEFAWPGASSWALNGRNSLMNPGPAMASHKEGEDRFFPLSGSLIFGKQGTGRDNVDADKVMITNEEEIKT
Consensus (498) NSEFAWPGASSWALNGRNSLMNPGPAMASHKEGEDRFFPLSGSLIFGKQGTGRDNVDADKVMITNEEEIKT
```

FIG. 1
CONTINUED

```
                                                                                    Section 9
         (569) 569       580       590       600       610       620       639
AAV9     (569) TNPVATESYGQVATNHQSAQAQAQTGWVQNQGILPGMVWQDRDVYLQGPIWAKIPHTDGNFHPSPLMGGFG
ClvD8    (569) TNPVATESYGQVATNHQSAQAQAQTGWVQNQGILPGMVWQDRDVYLQGPIWAKIPHTDGNFHPSPLMGGFG
AAV9Y    (569) TNPVATESYGQVATNHQSAQAQAQTGWVQNQGILPGMVWQDRDVYLQGPIWAKIPHTDGNFHPSPLMGGFG
AAV9H    (569) TNPVATESYGQVATNHQSAQAQAQTGWVQNQGILPGMVWQDRDVYLQGPIWAKIPHTDGNFHPSPLMGGFG
AAV9R    (569) TNPVATESYGQVATNHQSAQAQAQTGWVQNQGILPGMVWQDRDVYLQGPIWAKIPHTDGNFHPSPLMGGFG
AAV9I    (569) TNPVATESYGQVATNHQSAQAQAQTGWVQNQGILPGMVWQDRDVYLQGPIWAKIPHTDGNFHPSPLMGGFG
AAVHR    (569) TNPVATESYGQVATNHQSAQAQAQTGWVQNQGILPGMVWQDRDVYLQGPIWAKIPHTDGNFHPSPLMGGFG
Consensus(569) TNPVATESYGQVATNHQSAQAQAQTGWVQNQGILPGMVWQDRDVYLQGPIWAKIPHTDGNFHPSPLMGGFG Section 10
         (640) 640       650       660       670       680       690       700       710
AAV9     (640) MKHPPPQILIKNTPVPADPPTAFNKDKLNSFITQYSTGQVSVEIEWELQKENSKRWNPEIQYTSNYYKSNN
ClvD8    (640) MKHPPPQILIKNTPVPADPPTAFNKDKLNSFITQYSTGQVSVEIEWELQKENSKRWNPEIQYTSNYYKSNN
AAV9Y    (640) MKHPPPQILIKNTPVPADPPTAFNKDKLNSFITQYSTGQVSVEIEWELQKENSKRWNPEIQYTSNYYKSNN
AAV9H    (640) MKHPPPQILIKNTPVPADPPTAFNKDKLNSFITQYSTGQVSVEIEWELQKENSKRWNPEIQYTSNYYKSNN
AAV9R    (640) MKHPPPQILIKNTPVPADPPTAFNKDKLNSFITQYSTGQVSVEIEWELQKENSKRWNPEIQYTSNYYKSNN
AAV9I    (640) MKHPPPQILIKNTPVPADPPTAFNKDKLNSFITQYSTGQVSVEIEWELQKENSKRWNPEIQYTSNYYKSNN
AAVHR    (640) MKHPPPQILIKNTPVPADPPTAFNKDKLNSFITQYSTGQVSVEIEWELQKENSKRWNPEIQYTSNYYKSNN
Consensus(640) MKHPPPQILIKNTPVPADPPTAFNKDKLNSFITQYSTGQVSVEIEWELQKENSKRWNPEIQYTSNYYKSNN Section 11
         (711) 711       720       736
AAV9     (711) VEFAVNTEGVYSEPRPIGTRYLTRNL
ClvD8    (711) VEFAVNTEGVYSEPRPIGTRYLTRNL
AAV9Y    (711) VEFAVNTEGVYSEPRPIGTRYLTRNL
AAV9H    (711) VEFAVNTEGVYSEPRPIGTRYLTRNL
AAV9R    (711) VEFAVNTEGVYSEPRPIGTRYLTRNL
AAV9I    (711) VEFAVNTEGVYSEPRPIGTRYLTRNL
AAVHR    (711) VEFAVNTEGVYSEPRPIGTRYLTRNL
Consensus(711) VEFAVNTEGVYSEPRPIGTRYLTRNL
```

FIG. 1
CONTINUED

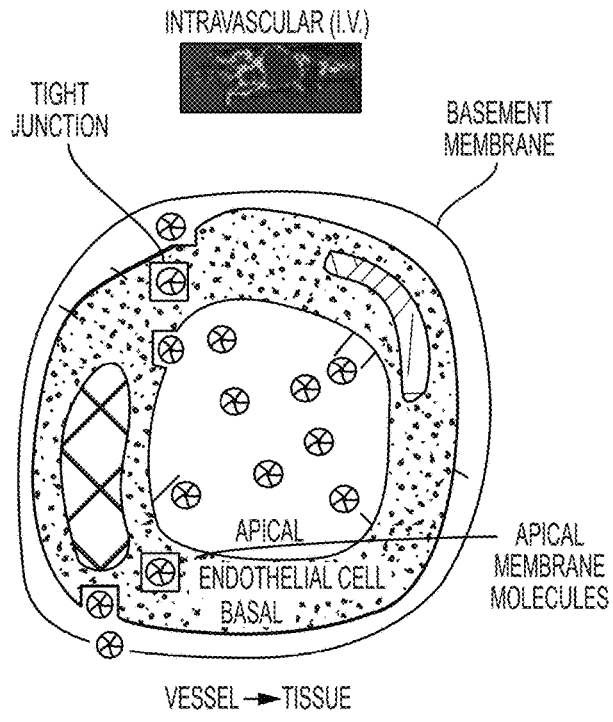
FIG. 2A
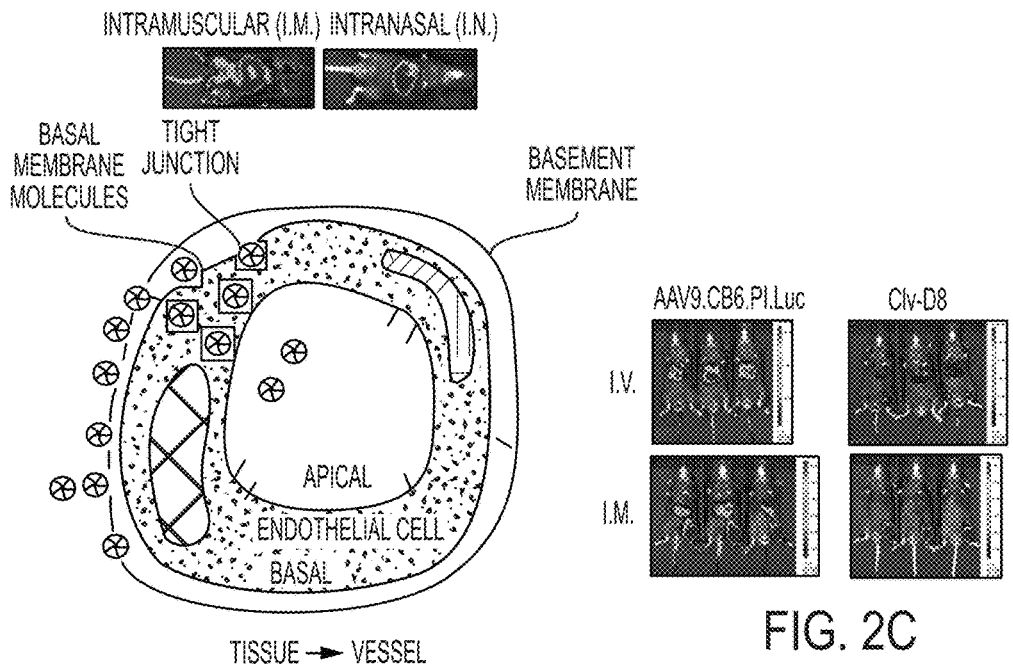
FIG. 2B
FIG. 2C

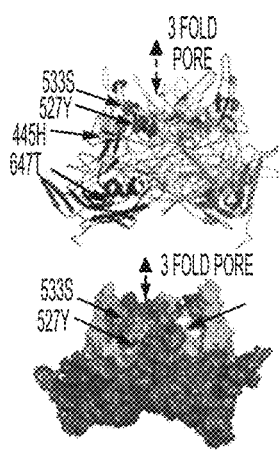
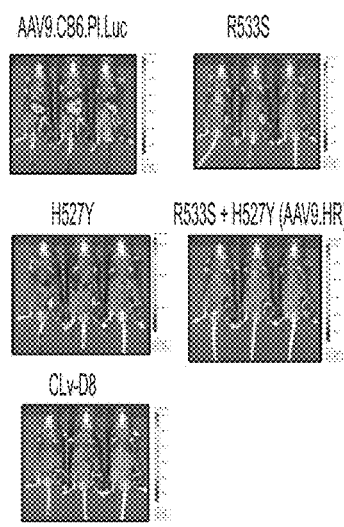
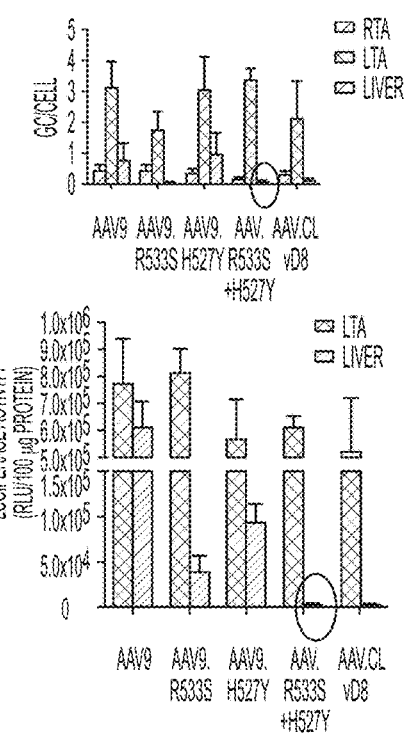
FIG. 4A
FIG. 4B
FIG. 4C

US 10,072,251 B2

RECOMBINANT AAVS HAVING USEFUL TRANSCYTOSIS PROPERTIES

RELATED APPLICATIONS

The application is a National Stage Application of PCT/US2015/016691, filed Feb. 19, 2015, and entitled "RECOMBINANT AAVS HAVING USEFUL TRANSCYTOSIS PROPERTIES", which claims the benefit under 35 U.S.C. § 119(e) to U.S. Provisional Application Ser. No. 61/942,002, entitled "RECOMBINANT AAVS HAVING USEFUL TRANSCYTOSIS PROPERTIES", filed on Feb. 19, 2014, the entire content of each of which is incorporated by reference herein.

FIELD

The disclosure in some aspects relates to isolated nucleic acids, compositions, and kits useful for identifying adeno-associated viruses in cells. In some aspects, the disclosure provides novel AAVs and methods of use thereof as well as related kits.

BACKGROUND

Adeno-associated virus (AAV) is a small (~26 nm) replication-defective, nonenveloped virus, that depends on the presence of a second virus, such as adenovirus or herpes virus, for its growth in cells. AAV was discovered in 1960s as a contaminant in adenovirus (a cold causing virus) preparations. Its growth in cells is dependent on the presence of adenovirus and, therefore, it was named as adeno-associated virus. AAV can infect both dividing and non-dividing cells and may incorporate its genome into that of the host cell. These features make AAV a very attractive candidate for creating viral vectors for gene therapy.

SUMMARY

The disclosure in some aspects relates to novel AAVs for gene therapy applications. Aspects of the disclosure relate to variants of AAV9 that have unique transcytosis properties. In some embodiments, recombinant AAVs (rAAVs) disclosed herein have a transduction efficiency similar to rAAV9 but improved safety profiles, particularly for muscle and lung gene delivery. Accordingly, in some embodiments, rAAV vectors are particularly useful for gene therapy of muscular, lung or other disorders. In some embodiments, a structural analysis of the ClvD8 capsid protein (a variant of the AAV9 capsid) was performed using the recently established AAV9 capsid structure as a template. In some embodiments, this analysis revealed differences in amino acids at position 647 and in other residues located at a position corresponding to AAV9 capsid protrusions that surrounds the icosahedral 3-fold axis of AAV9 VP3 protein. In some embodiments, amino acids in these protrusions play a role in receptor binding and cellular transduction.

In some embodiments, amino acids involved in peripheral (primarily liver) tissue transduction by IV delivery of rAAV9 were identified. In some embodiments, single and combinatory mutations for each of the amino acids on the AAV9 capsid that are mutated in AAV-ClvD8 were produced and evaluated for biodistribution profiles following delivery by intranasal or intramuscular injection. In some embodiments, a novel capsid mutant of AAV9, referred to as AAV9HR, produced local tissue-restricted expression and genome persistence by intramuscular and intranasal delivery, and produced low levels of expression in liver when delivered by intravascular (IV), intramuscular (IM) and intranasal (IN) delivery routes. In some embodiments, AAV9.HR displayed a blood clearance pattern similar to that of rAAV9 wt after IV, IM, and IN administration indicating that its ability to cross vascular barrier from tissue to vessel was not impaired.

Accordingly, aspects of the disclosure relate to recombinant AAVs (rAAVs) comprising an AAV capsid protein having an amino acid sequence selected from the group consisting of: SEQ ID NOs: 2-7, and compositions comprising the same. In some embodiments, compositions provided herein that comprise an rAAV further comprise a pharmaceutically acceptable carrier. In some embodiments, host cells are provided that contain a nucleic acid that comprises a coding sequence selected from the group consisting of: SEQ ID NO: 9-14 that is operably linked to a promoter, such that the cells are engineered to expess rAAV capsids. In some embodiments, compositions are provided that comprise a host cell and a sterile cell culture medium. In some embodiments, the compositions further comprise a cryopreservative.

Aspects of the disclosure relate to methods for delivering a transgene to a subject. In some embodiments, the methods involve administering a rAAV to a subject, in which the rAAV comprises: (i) a capsid protein having a sequence selected from SEQ ID NOs: 9 to 14, and (ii) at least one transgene, and in which the rAAV infects cells of a target tissue of the subject. In some embodiments, the target tissue is skeletal muscle, heart, liver, pancreas, brain or lung. In some embodiments, the rAAV is administered intravenously, transdermally, intraocularly, intrathecally, orally, intramuscularly, subcutaneously, intranasally, or by inhalation to a subject. In some embodiments, the subject is selected from a mouse, a rat, a rabbit, a dog, a cat, a sheep, a pig, and a non-human primate. In some embodiments, the subject is a human.

In some embodiments, at least one transgene of an rAAV encodes a protein. In some embodiments, the protein is an an antigen-binding protein, such as an immunoglobulin heavy chain or light chain, or fragment of either one. In some embodiments, the protein is a single chain Fv fragment or Fv-Fc fragment. Accordingly, in some embodiments, the rAAV can be used to infect cells of target tissue (e.g., muscle tissue) so as to engineer cells of the tissue to express an antigen-binding protein, such as an antibody or fragment thereof. In some embodiments, the protein is a central nervous system (CNS) protein. In some embodiments, the CNS protein is aspartoacylase (ASPA). In some embodiments, the ASPA is human ASPA. Accordingly, in some embodiments, the rAAV can be used to infect cells of a target tissue (e.g., CNS tissue) so as to engineer cells of the tissue to express ASPA.

In some embodiments, the protein is a secreted tumor suppressor protein. In some embodiments, the secreted tumor suppressor protein is selected from the group consisting of IGFBP7 and SRPX.

In other embodiments, the at least one transgene of an rAAV encodes a small interfering nucleic acid, such as a miRNA.

In some embodiments, the transgene comprises one or more elements that mediate tissue-specific expression. In some embodiments, the transgene of an rAAV expresses a transcript that comprises at least one binding site for a miRNA, wherein the miRNA inhibits activity of the transgene, in a tissue other than the target tissue, by hybridizing to the binding site. In some embodiments, the transgene of an rAAV comprises a tissue specific promoter or inducible promoter. In some embodiments, the tissue specific promoter is a liver-specific thyroxin binding globulin (TBG) promoter, a insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter.

Aspects of the disclosure relate to isolated nucleic acids encoding an AAV caspid protein having an amino acid sequence selected from the group consisting of: SEQ ID NOs: 2-7. In some embodiments, isolated nucleic acids are provided that comprise a sequence selected from the group consisting of: SEQ ID NO: 9-14. In some embodiments, Aspects of the disclosure relate to isolated AAV capsid protein comprising an amino acid sequence selected from the group consisting of: SEQ ID NOs: 2-7 and compositions comprising the same.

Aspects of the disclosure relate to kits for producing a rAAV. In some embodiments, the kits comprise a container housing an isolated nucleic acid having a sequence of any one of SEQ ID NO: 9-14. In some embodiments, the kits further comprise at least one container housing a recombinant AAV vector, wherein the recombinant AAV vector comprises a transgene. In some embodiments, the kits comprise a container housing a recombinant AAV having an isolated AAV capsid protein having an amino acid sequence as set forth in any of SEQ ID NOS: 2-7. In some embodiments, the kits further comprise instructions for producing the rAAV.

Aspects of the disclosure relate to methods of delivering rAAVs for the treatment of disease. In some embodiments, the disease is a central nervous system (CNS) disease. In some embodiments, the CNS disease is Canavan disease. Accordingly, in some embodiments the disclosure provides a method for treating Canavan disease, the method comprising administering to a subject a therapeutically effective amount of a rAAV to a subject, wherein the rAAV comprises (i) a capsid protein having a sequence selected from SEQ ID NOs: 10 to 14, and (ii) at least one transgene, wherein the at least one transgene encodes ASPA; and wherein the rAAV infects cells of a target tissue of the subject. In some embodiments of the method, the target tissue is CNS tissue. In some embodiments, the ASPA is human ASPA.

In some embodiments, the disease is cancer. Accordingly, in some embodiments, the disclosure provides a method for treating cancer, the method comprising administering to a subject a therapeutically effective amount of a rAAV to a subject, wherein the rAAV comprises: (i) a capsid protein having a sequence selected from SEQ ID NOs: 10 to 14, and (ii) at least one transgene, wherein the at least one transgene encodes a tumor suppressor protein; and wherein the rAAV infects cells of a target tissue of the subject.

In some embodiments, the tumor suppressor protein is selected from the group consisting of IGFBP7 and SRPX.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

Figure 1:
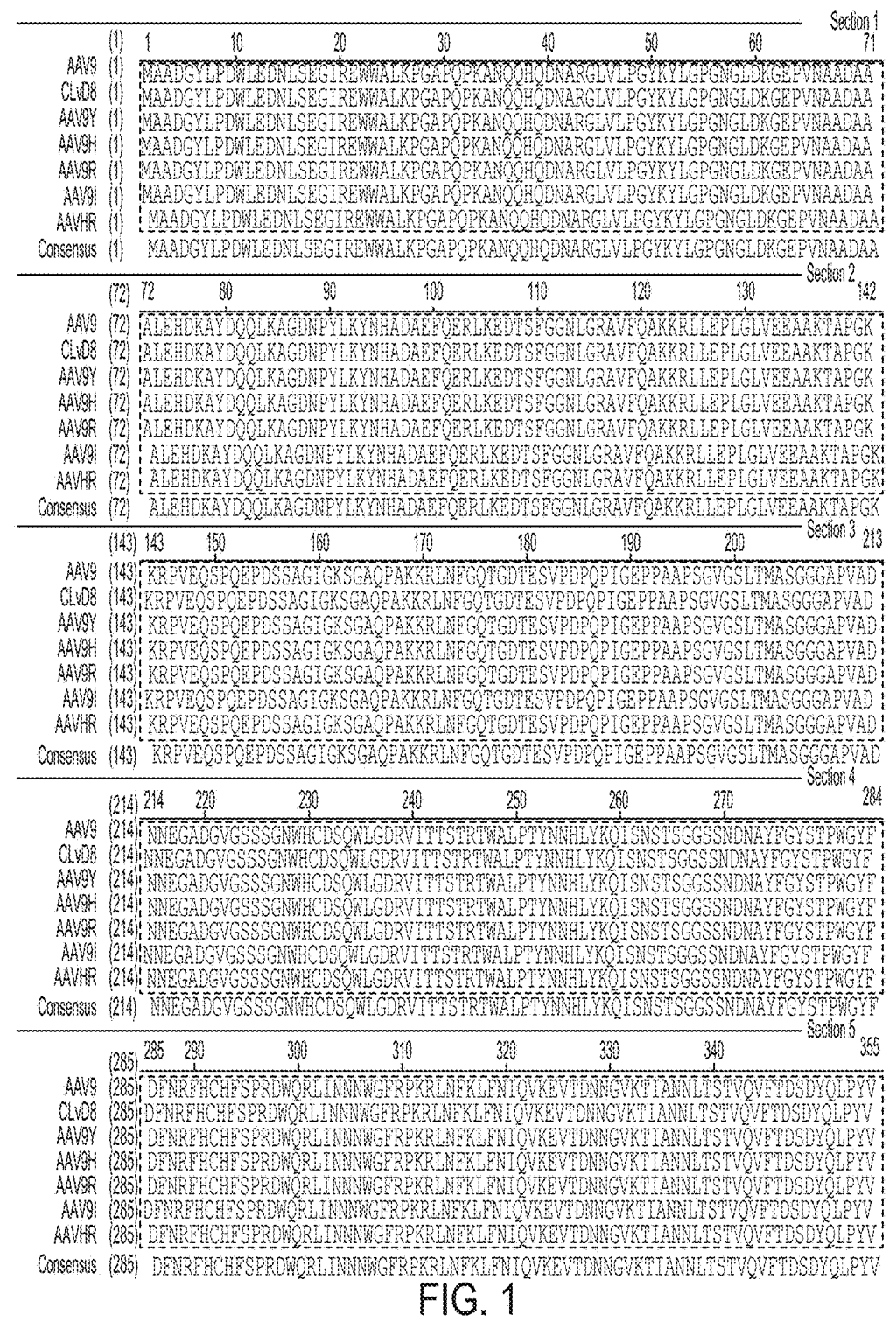

FIG. 1 depicts an alignment of AAV9 variants; sequences in the alignment are as follows: AAV9: SEQ ID NO:1, CLvD8: SEQ ID NO: 2, AAV9Y: SEQ ID NO: 6, AAV9H: SEQ ID NO: 3, AAV9R: SEQ ID NO: 5, AAV9I: SEQ ID NO: 4, AAV.HR: SEQ ID NO: 7, Consensus: SEQ ID NO: 15;

FIG. 2A-D depict results showing that Clv-D8 has reduced transcytosis capability compared with AAV9;

FIG. 4 depicts that AAV9.HR (derived from CLv-D8, Δ 2 a.a.)-mediated transgene expression is limited to injected muscle after IM injection;

DETAILED DESCRIPTION

Figure 2D:
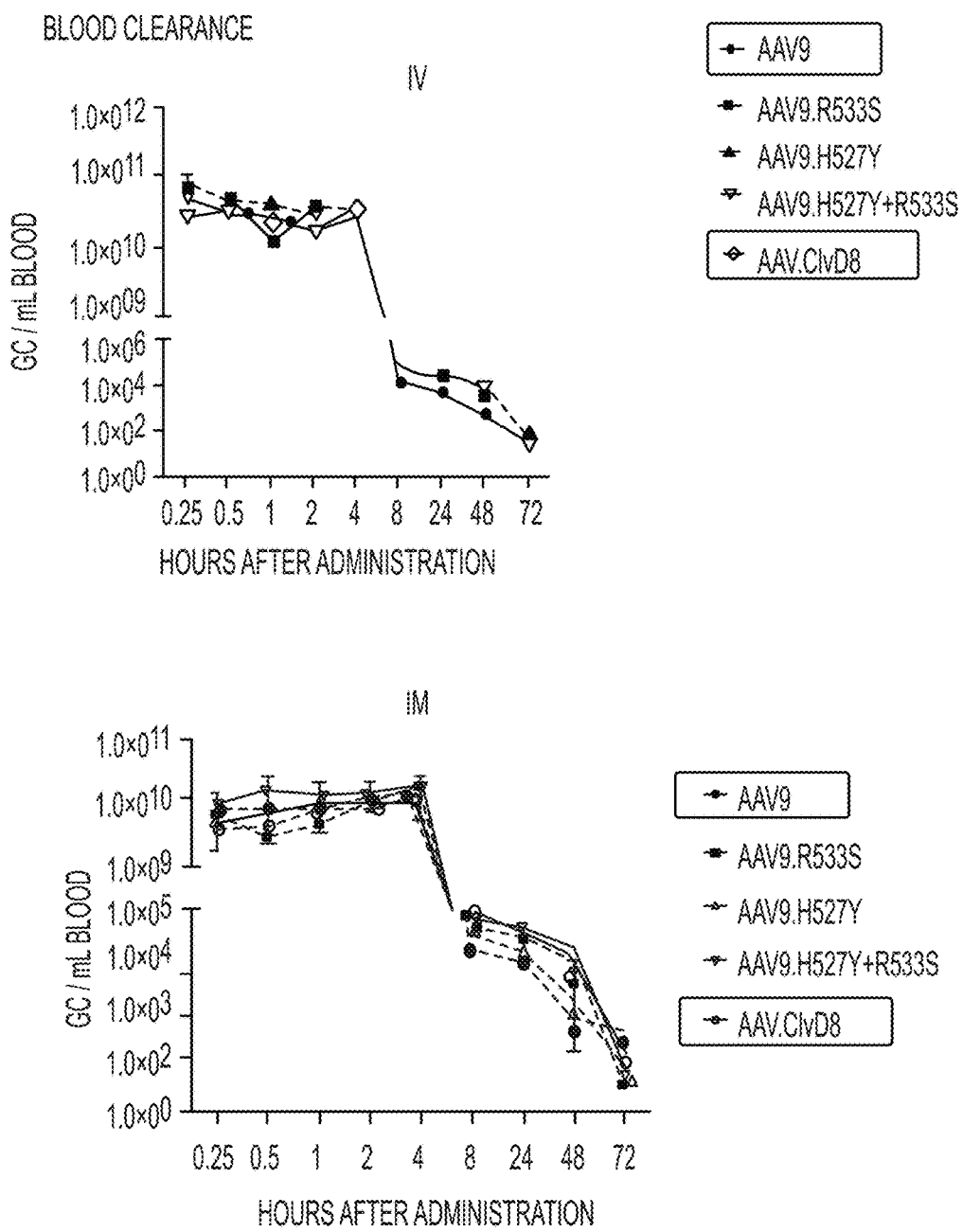

In some embodiments, recombinant AAVs are provided herein that overcome shortcomings of existing rAAV technologies in that they have distinct transcytosis properties that make them useful for certain gene therapy and research applications.

In some aspects of the disclosure new AAV capsid proteins are provided that have distinct tissue targeting capabilities. In some embodiments, an AAV capsid protein is isolated from the tissue to which an AAV comprising the capsid protein targets. In some aspects, methods for delivering a transgene to a target tissue in a subject are provided. The transgene delivery methods may be used for gene therapy (e.g., to treat disease) or research (e.g., to create a somatic transgenic animal model) applications.

Isolated AAV Capsid Proteins and Nucleic Acids Encoding the Same

AAVs are natural inhabitants in mammals. AAVs isolated from mammals, particularly non-human primates, are useful for creating gene transfer vectors for clinical development and human gene therapy applications. The disclosure provides in some aspects novel AAV capsid proteins that have been development through functional mutagenesis. Protein and amino acid sequences as well as other information regarding the AAVs capsid are set forth in the sequence listing.

In some embodiments, an AAV capsid is provided that has an amino acid sequence of SEQ ID NO: 1 with one or more of the following amino acid alterations: Y445H, H527Y, I647T, and R533S.

In some embodiments, an AAV capsid is provided that has an amino acid sequence of SEQ ID NO: 1 with one or more of the following amino acid alterations: Y445H, H527Y, I647T, and R533S and up to 5, up to 10, up to 20, up to 30, up to 40, up to 50, up to 100 other amino acid alternations (e.g., conservative amino acid substitutions).

An example of an isolated nucleic acid that encodes an AAV capsid protein is a nucleic acid having a sequence selected from the group consisting of: SEQ ID NO: 9-14 as well as nucleic acids having substantial homology thereto.

In some embodiments, isolated nucleic acids that encode AAV capsids are provided that have sequences selected from: SEQ ID NO: 9, 10, 11, 12, 13, and 14.

In some embodiments, nucleic acids are provided that encode an AAV capsid having one or more of the following amino acid alterations: Y445H, H527Y, I647T, and R533S based on the amino acid sequence of SEQ ID NO: 1.

In some embodiments, nucleic acids are provided that encode an AAV capsid having one or more of the following amino acid alterations: Y445H, H527Y, I647T, and R533S based on the amino acid sequence of SEQ ID NO: 1 and up to 5, up to 10, up to 20, up to 30, up to 40, up to 50, up to 100 other amino acid alternations.

In some embodiments, a fragment (portion) of an isolated nucleic acid encoding a AAV capsid sequence may be useful for constructing a nucleic acid encoding a desired capsid sequence. Fragments may be of any appropriate length (e.g., at least 9, at least 18, at least 36, at least 72, at least 144, at least 288, at least 576, at least 1152 or more nucleotides in length). The fragment may be a fragment that does not encode a peptide that is identical to a sequence of SEQ ID NO: 1. For example, a fragment of nucleic acid sequence encoding a variant amino acid (compared with a known AAV serotype) may be used to construct, or may be incorporated within, a nucleic acid sequence encoding an AAV capsid sequence to alter the properties of the AAV capsid. For example, a nucleic sequence encoding an AAV variant may comprise n amino acid variants (e.g., in which n=1, 2, 3, 4, 5, 6, 7, 8, 9, 10 or more) compared with a known AAV serotype (e.g., AAV9). A recombinant cap sequence may be constructed having one or more of the n amino acid variants by incorporating fragments of a nucleic acid sequence comprising a region encoding a variant amino acid into the sequence of a nucleic acid encoding the known AAV serotype. The fragments may be incorporated by any appropriate method, including using site directed mutagenesis. Thus, new AAV variants may be created having new properties.

In some cases, fragments of capsid proteins disclosed herein are provided. Such fragments may at least 10, at least 20, at least 50, at least 100, at least 200, at least 300, at least 400, at least 500 or more amino acids in length. In some embodiments, chimeric capsid proteins are provided that comprise one or more fragments of one or more capsid proteins disclosed herein.

"Homology" refers to the percent identity between two polynucleotides or two polypeptide moieties. The term "substantial homology", when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences. When referring to a polypeptide, or fragment thereof, the term "substantial homology" indicates that, when optimally aligned with appropriate gaps, insertions or deletions with another polypeptide, there is nucleotide sequence identity in about 90 to 100% of the aligned sequences. The term "highly conserved" means at least 80% identity, preferably at least 90% identity, and more preferably, over 97% identity. In some cases, highly conserved may refer to 100% identity. Identity is readily determined by one of skill in the art by, for example, the use of algorithms and computer programs known by those of skill in the art.

As described herein, alignments between sequences of nucleic acids or polypeptides are performed using any of a variety of publicly or commercially available Multiple Sequence Alignment Programs, such as "Clustal W", accessible through Web Servers on the internet. Alternatively, Vector NTI utilities may also be used. There are also a number of algorithms known in the art which can be used to measure nucleotide sequence identity, including those contained in the programs described above. As another example, polynucleotide sequences can be compared using BLASTN, which provides alignments and percent sequence identity of the regions of the best overlap between the query and search sequences. Similar programs are available for the comparison of amino acid sequences, e.g., the "Clustal X" program, BLASTP. Typically, any of these programs are used at default settings, although one of skill in the art can alter these settings as needed. Alternatively, one of skill in the art can utilize another algorithm or computer program which provides at least the level of identity or alignment as that provided by the referenced algorithms and programs. Alignments may be used to identify corresponding amino acids between two proteins or peptides. A "corresponding amino acid" is an amino acid of a protein or peptide sequence that has been aligned with an amino acid of another protein or peptide sequence. Corresponding amino acids may be identical or non-identical. A corresponding amino acid that is a non-identical amino acid may be referred to as a variant amino acid.

Alternatively for nucleic acids, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Recombinant AAVs

In some aspects, the disclosure provides isolated AAVs. As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected. In some embodiments, the rAAV comprises a capsid protein having an amino acid sequence as set forth in any one of SEQ ID NOs 2-7, or a protein having substantial homology thereto.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein (e.g., a nucleic acid having a sequence as set forth in any one of SEQ ID NOs 9-14) or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected.

Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA, miRNA inhibitor) from a transcribed gene.

The foregoing methods for packaging recombinant vectors in desired AAV capsids to produce the rAAVs of the disclosure are not meant to be limiting and other suitable methods will be apparent to the skilled artisan.

Recombinant AAV Vectors

"Recombinant AAV (rAAV) vectors" of the disclosure are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

As used herein, a "target tissue" refers to a tissue of interest, e.g., a tissue where it is desirable to deliver and/or express a transgene by AAV-mediated delivery. Target tissue may be healthy or diseased. A target tissue may be in vivo or ex vivo. In some embodiments, a target tissue contains one or more cell types present in an extracellular matrix. For example, a target tissue may comprise tumor or cancer cells and/or normal or non-transformed cells. A target tissue may be a tissue adversely affected by the improper function of a particular protein (e.g. non-functional ASPA in Canavan disease). In some embodiments, target tissue is blood, muscle, heart, pancreas and/or CNS tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be "operably" linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA, miRNA inhibitor).

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, a insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a $\alpha$-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (, Hansal et al., J. Immunol., 161:1063-8 (1998); immunoglobulin heavy chain promoter; T cell receptor $\alpha$-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, one or more bindings sites for one or more of miRNAs are incorporated in a transgene of a rAAV vector, to inhibit the expression of the transgene in one or more tissues of an subject harboring the transgene. The skilled artisan will appreciate that binding sites may be selected to control the expression of a trangene in a tissue specific manner. For example, binding sites for the liver-specific miR-122 may be incorporated into a transgene to inhibit expression of that transgene in the liver. The target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Recombinant AAV Vector: Transgene Coding Sequences

The composition of the transgene sequence of the rAAV vector will depend upon the use to which the resulting vector will be put. For example, one type of transgene sequence includes a reporter sequence, which upon expression produces a detectable signal. In another example, the trangene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

Reporter sequences that may be provided in a transgene include, without limitation, DNA sequences encoding $\beta$-lactamase, $\beta$-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for $\beta$-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of an rAAV.

In some aspects, the disclosure provides rAAV vectors for use in methods of preventing or treating one or more genetic deficiencies or dysfunctions in a mammal, such as for example, a polypeptide deficiency or polypeptide excess in a mammal, and particularly for treating or reducing the severity or extent of deficiency in a human manifesting one or more of the disorders linked to a deficiency in such polypeptides in cells and tissues. The method involves administration of an rAAV vector that encodes one or more therapeutic peptides, polypeptides, siRNAs, microRNAs, antisense nucleotides, etc. in a pharmaceutically-acceptable carrier to the subject in an amount and for a period of time sufficient to treat the deficiency or disorder in the subject suffering from such a disorder.

Thus, the disclosure embraces the delivery of rAAV vectors encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18.

The rAAV vectors may comprise a gene to be transferred to a subject to treat a disease associated with reduced expression, lack of expression or dysfunction of the gene. In some embodiments, the dysfunctional gene is ASPA and the disease is Canavan disease.

Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

In some embodiments, The rAAV vectors may comprise a gene encoding an antigen-binding protein, such as an immunoglobulin heavy chain or light chain or fragment thereof, e.g., that may be used for therapeutic purposes. In some embodiments, the protein is a single chain Fv fragment or Fv-Fc fragment. Accordingly, in some embodiments, the rAAV can be used to infect cells of a target tissue (e.g., muscle tissue) so as to engineer cells of the tissue to express an antigen-binding protein, such as an antibody or fragment thereof. In some embodiments, to generate rAAVs that express the antibodies or antigen binding fragments, cDNAs engineered to express such proteins will be suclonned into an appropriate plasmid backbone and packaged into an rAAV.

The rAAVs of the disclosure can be used to restore the expression of genes that are reduced in expression, silenced, or otherwise dysfunctional in a subject (e.g., a tumor suppressor that has been silenced in a subject having cancer). The rAAVs of the disclosure can also be used to knockdown the expression of genes that are aberrantly expressed in a subject (e.g., an oncogene that is expressed in a subject having cancer). In some embodiments, an rAAV vector comprising a nucleic acid encoding a gene product associated with cancer (e.g., tumor suppressors) may be used to treat the cancer, by administering a rAAV harboring the rAAV vector to a subject having the cancer. In some embodiments, an rAAV vector comprising a nucleic acid encoding a small interfering nucleic acid (e.g., shRNAs, miRNAs) that inhibits the expression of a gene product associated with cancer (e.g., oncogenes) may be used to treat the cancer, by administering a rAAV harboring the rAAV vector to a subject having the cancer. In some embodiments, an rAAV vector comprising a nucleic acid encoding a gene product associated with cancer (or a functional RNA that inhibits the expression of a gene associated with cancer) may be used for research purposes, e.g., to study the cancer or to identify therapeutics that treat the cancer. The following is a non-limiting list of exemplary genes known to be associated with the development of cancer (e.g., oncogenes and tumor suppressors): AARS, ABCB1, ABCC4, ABI2, ABL1, ABL2, ACK1, ACP2, ACY1, ADSL, AK1, AKR1C2, AKT1, ALB, ANPEP, ANXA5, ANXA7, AP2M1, APC, ARHGAP5, ARHGEF5, ARID4A, ASNS, ATF4, ATM, ATP5B, ATP5O, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5, CCYR61, CD24, CD44, CD59, CDC20, CDC25, CDC25A, CDC25B, CDC2L5, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAF1A, CIB1, CKMT1, CLK1, CLK2, CLK3, CLNS1A, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXG1A, FOXO1A, FRAP1, FRZB, FTL, FZD2, FZD5, FZD9, G22P1, GAS6, GCN5L2, GDF15, GNA13, GNAS, GNB2, GNB2L1, GPR39, GRB2, GSK3A, GSPT1, GTF2I, HDAC1, HDGF, HMMR, HPRT1, HRB, HSPA4, HSPA5, HSPA8, HSPB1, HSPH1, HYAL1, HYOU1, ICAM1, ID1, ID2, IDUA, IER3, IFITM1, IGF1R, IGF2R, IGFBP3, IGFBP4, IGFBP5, IL1B, ILK, ING1, IRF3, ITGA3, ITGA6, ITGB4, JAK1, JARID1A, JUN, JUNB, JUND, K-ALPHA-1, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINJ1, NMBR, NME1, NME2, NME3, NOTCH1, NOTCH2, NOTCH4, NPM1, NQO1, NR1D1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPP1CA, PPP2R5A, PRDX2, PRDX4, PRKAR1A, PRKCBP1, PRNP, PRSS15, PSMA1, PTCH, PTEN, PTGS1, PTMA, PTN, PTPRN, RAB5A, RAC1, RAD50, RAF1, RALBP1, RAP1A, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6KB1, RRM1, SARS, SELENBP1, SEMA3C, SEMA4D, SEPP1, SERPINH1, SFN, SFPQ, SFRS7, SHB, SHH, SIAH2, SIVA, SIVA TP53, SKI, SKIL, SLC16A1, SLC1A4, SLC20A1, SMO, SMPD1, SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFBI, TGFBR2, TGFBR3, THBS1, TIE, TIMP1, TIMP3, TJP1, TK1, TLE1, TNF, TNFRSF10A, TNFRSF10B, TNFRSF1A, TNFRSF1B, TNFRSF6, TNFSF7, TNK1, TOB1, TP53, TP53BP2, TP53I3, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCC1, YES1, YWHAB, YWHAZ, ZAP70, and ZNF9.

In some embodiments, rAAV vectors comprising a transgene encoding a tumor suppressor protein are useful for the treatment of cancer. As used herein, the term "tumor suppressor protein" refers to protein that inhibits the formation, development or maintainance of a tumor. In some embodiments, a tumor suppressor protein suppresses regulation of the cell cycle and/or promotes apoptosis. Loss or dysfunction of tumor suppressor proteins is a key step in the development of cancer. Accordingly, expression of tumor suppressor proteins inhibits or slows the growth of cancerous tumors and may therefore be a viable therapeutic strategy for treatment of cancer. In some embodiments, the tumor suppressor protein is a secreted tumor suppressor protein. Non-limiting examples of secreted tumor suppressor proteins include IGFBP7, SRPX, and others disclosed for example in Min Zhao, Jingchun Sun, Zhongming Zhao (2013) TSGene: a web resource for tumor suppressor genes. Nucleic Acids Research, 41: D970-D976.

A rAAV vector may comprise as a transgene, a nucleic acid encoding a protein or functional RNA that modulates apoptosis. The following is a non-limiting list of genes associated with apoptosis and nucleic acids encoding the products of these genes and their homologues and encoding small interfering nucleic acids (e.g., shRNAs, miRNAs) that inhibit the expression of these genes and their homologues are useful as transgenes in certain embodiments of the disclosure: RPS27A, ABL1, AKT1, APAF1, BAD, BAG1, BAG3, BAG4, BAK1, BAX, BCL10, BCL2, BCL2A1, BCL2L1, BCL2L10, BCL2L11, BCL2L12, BCL2L13, BCL2L2, BCLAF1, BFAR, BID, BIK, NAIP, BIRC2, BIRC3, XIAP, BIRC5, BIRC6, BIRC7, BIRC8, BNIP1, BNIP2, BNIP3, BNIP3L, BOK, BRAF, CARD10, CARD11, NLRC4, CARD14, NOD2, NOD1, CARD6, CARD8, CARD9, CASP1, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGF1R, LTA, LTBR, MCL1, NOL3, PYCARD, RIPK1, RIPK2, TNF, TNFRSF10A, TNFRSF10B, TNFRSF10C, TNFRSF10D, TNFRSF11B, TNFRSF12A, TNFRSF14, TNFRSF19, TNFRSF1A, TNFRSF1B, TNFRSF21, TNFRSF25, CD40, FAS, TNFRSF6B, CD27, TNFRSF9, TNFSF10, TNFSF14, TNFSF18, CD4OLG, FASLG, CD70, TNFSF8, TNFSF9, TP53, TP53BP2, TP73, TP63, TRADD, TRAF1, TRAF2, TRAF3, TRAF4, and TRAF5.

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

Useful transgene products also include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as transgenes or as targets for small interfering nucleic acids encoded by transgenes (e.g., miRNA sponges, antisense oligonucleotides, TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR- 518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548l, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551 a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891 a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. MicroRNA inhibitors can be expressed in cells from a transgenes of a rAAV vector, as discussed above. MicroRNA sponges specifically inhibit miRNAs through a complementary heptameric seed sequence (Ebert, M.S. Nature Methods, Epub Aug. 12, 2007;). In some embodiments, an entire family of miRNAs can be silenced using a single sponge sequence. TuD RNAs achieve efficient and long-term-suppression of specific miRNAs in mammalian cells (See, e.g., Takeshi Haraguchi, et al., Nucleic Acids Research, 2009, Vol. 37, No. 6 e43, the contents of which relating to TuD RNAs are incorporated herein by reference). Other methods for silencing miRNA function (derepression of miRNA targets) in cells will be apparent to one of ordinary skill in the art.

In some embodiments, the cloning capacity of the recombinant RNA vector may limited and a desired coding sequence may require the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Somatic Transgenic Animal Models Produced Using rAAV-Based Gene Transfer

The disclosure also involves the production of somatic transgenic animal models of disease using recombinant Adeno-Associated Virus (rAAV) based methods. The methods are based, at least in part, on the observation that AAV serotypes and variants thereof mediate efficient and stable gene transfer in a tissue specific manner in adult animals. The rAAV elements (capsid, promoter, transgene products) are combined to achieve somatic transgenic animal models that express a stable transgene in a time and tissue specific manner. The somatic transgenic animal produced by the methods of the disclosure can serve as useful models of human disease, pathological state, and/or to characterize the effects of gene for which the function (e.g., tissue specific, disease role) is unknown or not fully understood. For example, an animal (e.g., mouse) can be infected at a distinct developmental stage (e.g., age) with a rAAV comprising a capsid having a specific tissue targeting capability (e.g., liver, heart, pancreas, CNS) and a transgene having a tissue specific promoter driving expression of a gene involved in disease. Upon infection, the rAAV infects distinct cells of the target tissue and produces the product of the transgene.

In some embodiments, the sequence of the coding region of a transgene is modified. The modification may alter the function of the product encoded by the transgene. The effect of the modification can then be studied in vivo by generating a somatic transgenic animal model using the methods disclosed herein. In some embodiments, modification of the sequence of coding region is a nonsense mutation that results in a fragment (e.g., a truncated version). In other cases, the modification is a missense mutation that results in an amino acid substitution. Other modifications are possible and will be apparent to the skilled artisan.

In some embodiments, the transgene causes a pathological state. A transgene that causes a pathological state is a gene whose product has a role in a disease or disorder (e.g., causes the disease or disorder, makes the animal susceptible to the disease or disorder) and/or may induce the disease or disorder in the animal. The animal can then be observed to evaluate any number of aspects of the disease (e.g., progression, response to treatment, etc). These examples are not meant to be limiting, other aspects and examples are disclosed herein and described in more detail below.

The disclosure in some aspects, provide methods for producing somatic transgenic animal models through the targeted destruction of specific cell types. For example, models of type 1 diabetes can be produced by the targeted destruction of pancreatic Beta-islets. In other examples, the targeted destruction of specific cell types can be used to evaluate the role of specific cell types on human disease. In this regard, transgenes that encode cellular toxins (e.g., diphtheria toxin A (DTA)) or pro-apoptotic genes (NTR, Box, etc.) can be useful as transgenes for functional ablation of specific cell types. Other exemplary transgenes, whose products kill cells are embraced by the methods disclosed herein and will be apparent to one of ordinary skill in the art.

The disclosure in some aspects, provides methods for producing somatic transgenic animal models to study the long-term effects of over-expression or knockdown of genes. The long term over expression or knockdown (e.g., by shRNA, miRNA, miRNA inhibitor, etc.) of genes in specific target tissues can disturb normal metabolic balance and establish a pathological state, thereby producing an animal model of a disease, such as, for example, cancer. The disclosure in some aspects, provides methods for producing somatic transgenic animal models to study the long-term effects of over-expression or knockdown of gene of potential oncogenes and other genes to study tumorigenesis and gene function in the targeted tissues. Useful transgene products include proteins that are known to be associated with cancer and small interfering nucleic acids inhibiting the expression of such proteins. Other suitable transgenes may be readily selected by one of skill in the art provided that they are useful for creating animal models of tissue-specific pathological state and/or disease.

Recombinant AAV Administration Methods

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g, Macaque). In some embodiments a host animal does not include a human.

Delivery of the rAAVs to a mammalian subject may be by, for example, intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. Moreover, in certain instances, it may be desirable to deliver the virions to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000). Recombinant AAVs may also be delivered indirectly to the CNS, for example by intravenous injection.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVS are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, a effective amount of the rAAV is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas or CNS tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the rAAV-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered trangenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500.ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (ie., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder).

The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for producing specific somatic animal models.

In some cases, the methods involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some cases, RNA from the transfected cells provides a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells may also be infected with a helper virus, such as an Adenovirus or a Herpes Virus. In a specific embodiment, the helper functions are provided by an adenovirus. The adenovirus may be a wild-type adenovirus, and may be of human or non-human origin, preferably non-human primate (NHP) origin. Similarly adenoviruses known to infect non-human animals (e.g., chimpanzees, mouse) may also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions may be utilized. Such recombinant viruses are known in the art and may be prepared according to published techniques. See, e.g., U.S. Pat. No. 5,871,982 and U.S. Pat. No. 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells may also be transfected with a vector (e.g., helper vector) which provides helper functions to the AAV. The vector providing helper functions may provide adenovirus functions, including, e.g., E1a, E1b, E2a, E4ORF6. The sequences of adenovirus gene providing these functions may be obtained from any known adenovirus serotype, such as serotypes 2, 3, 4, 7, 12 and 40, and further including any of the presently identified human types known in the art. Thus, in some embodiments, the methods involve transfecting the cell with a vector expressing one or more genes necessary for AAV replication, AAV gene transcription, and/or AAV packaging.

In some cases, a novel isolated capsid gene can be used to construct and package recombinant AAV vectors, using methods well known in the art, to determine functional characteristics associated with the novel capsid protein encoded by the gene. For example, novel isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the novel isolated capsid gene can be determined by examining the expression of the reporter gene in various tissues (e.g., heart, liver, kidneys) of the animal. Other methods for characterizing the novel isolated capsid genes are disclosed herein and still others are well known in the art.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit may involve methods for detecting a latent AAV in a cell. In addition, kits of the disclosure may include, instructions, a negative and/or positive control, containers, diluents and buffers for the sample, sample preparation tubes and a printed or electronic table of reference AAV sequence for sequence comparisons.

EXAMPLES

Example 1

Development of Novel AAV Vectors for Muscular and Lung Gene Delivery: An Engineered Novel Capsid Variant of AAV9 for Muscle and Lung-Directed Transgene Expression AAV-ClvD8 is an AAV9 variety with significantly reduced transcytosis property. Structural analysis of the ClvD8 capsid was performed using newly established AAV9 capsid structure as a template. This analysis revealed that other than the alteration at position 647, the other mutated amino acid (a.a.) residues in Clv-D8 (compared with AAV9) are located on the AAV9 capsid protrusions that surround the icosahedral 3-fold axis of AAV9 VP3 protein, which plays a role in receptor binding and cellular transduction.

In an attempt to map the a.a. residual(s) responsible for peripheral (primarily liver) tissue transduction by IV delivery of rAAV9, single and combinatory mutations for each of the a.a. on the AAV9 capsid that are mutated in AAV-ClvD8 were produced. Corresponding luciferase expressing vectors were delivered into C57BL/6 mice by intravascular (IV), intranasal (IN) and intramuscular (IM) injections to compare their luciferase transduction and vector genome biodistribution profiles with rAAV9 wild type (wt).

Using this approach, a novel capsid mutant of AAV9 was produced that is identified herein as AAV9.HR that generated significantly lower luciferase expression and vector genome abundance (VGA) in liver by all three routes and local tissue-restricted expression and genome persistence by IM and IN delivery. Other mutants that were produced using this method are identified herein as AAV9H, AAV9I, AAV9R, and AAV9Y (as depicted in FIG. 1).

FIG. 2A-C depicts that Clv-D8, which is a chimpanzee-derived AAV9-relative (Δ 4 a.a.), has abolished transcytosis capability. FIG. 2D shows that the blood clearance pattern is not change between AAV9 and CLv-D8, and other mutants of AAV9 (i.e., R533S, H527Y, and double R533S+H527Y compared with AAV9, referred to as AAV9R, AAV9H and AAV9HR, respectively) for IV or IM administration.

Figure 3:
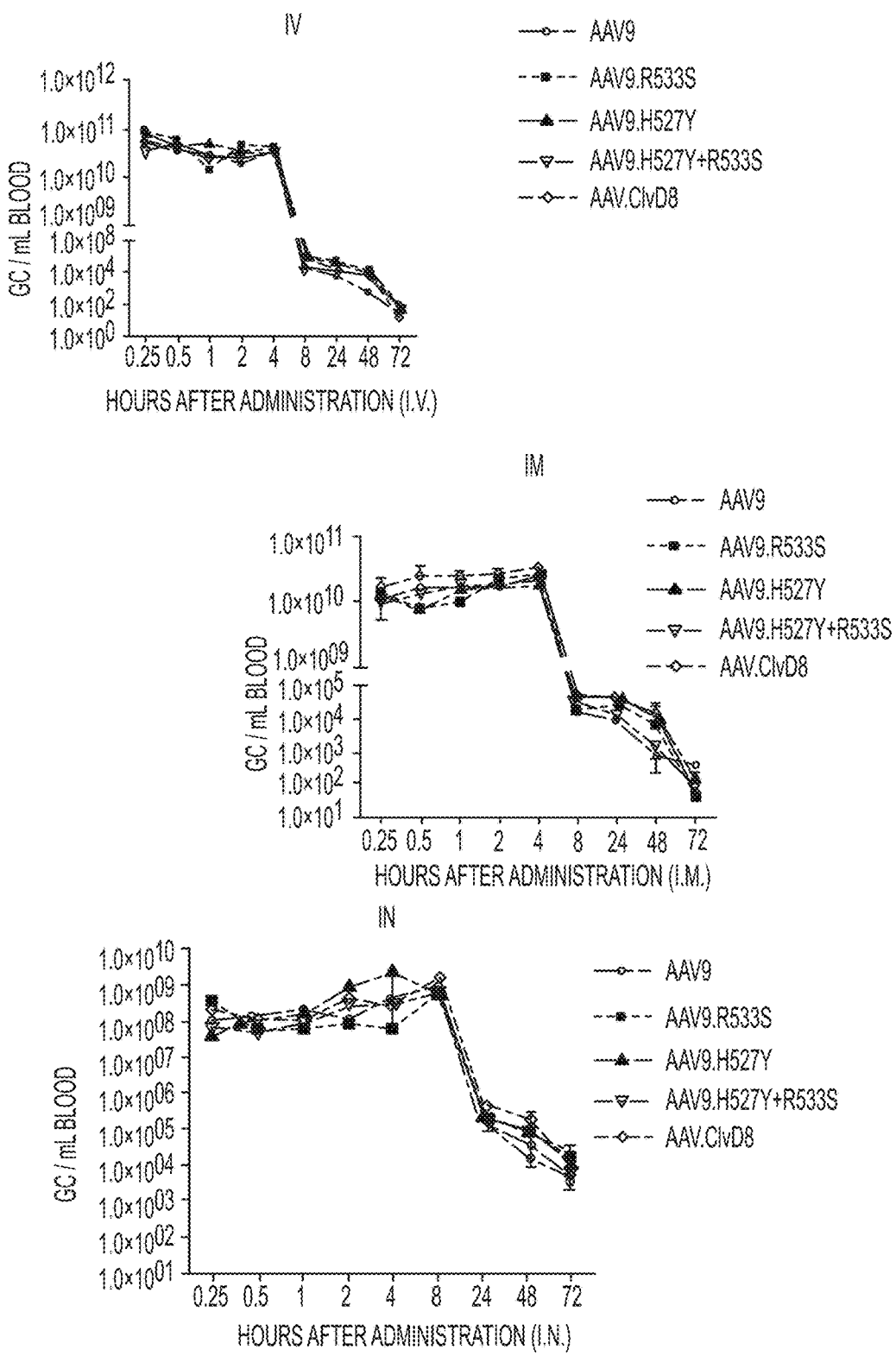
FIG. 3 depicts that AAV9.HR (derived from CLv-D8, Δ2 a.a.) shows similar blood clearance pattern compared to wt AAV9 after IV, IN and IM injection.

AAV9.HR (derived from CLv-D8, Δ 2 a.a.) displayed a blood clearance pattern similar to that of rAAV9 wt after IV, IM, and IN administration suggesting that its ability to cross vascular barrier from tissue to vessel was not impaired. Six-week old male C57BL/6 mice were injected via left tibialis anterior with AAV9 and its mutants (1.0 e11 GC/mouse, n=3). At specific time points (0-72 hrs), 5 µl of tail vein blood were collected, diluted 1000-fold into PBS and then proceeded for qPCR analysis. Standards were spiked with normal mouse blood (1000-fold dilution) without treatment. See FIG. 3.

Luciferase assays were performed to evaluate the distribution of AAVs in mice after IM injection. It was found that although AAV9.HR can enter vessel after IM injection, it is limited in its ability to enter major organ, such as liver, by transcytosis. See FIG. 4. The AAV9.HR mediated transgene expression is essentially limited in injected muscle.

Figure 5:
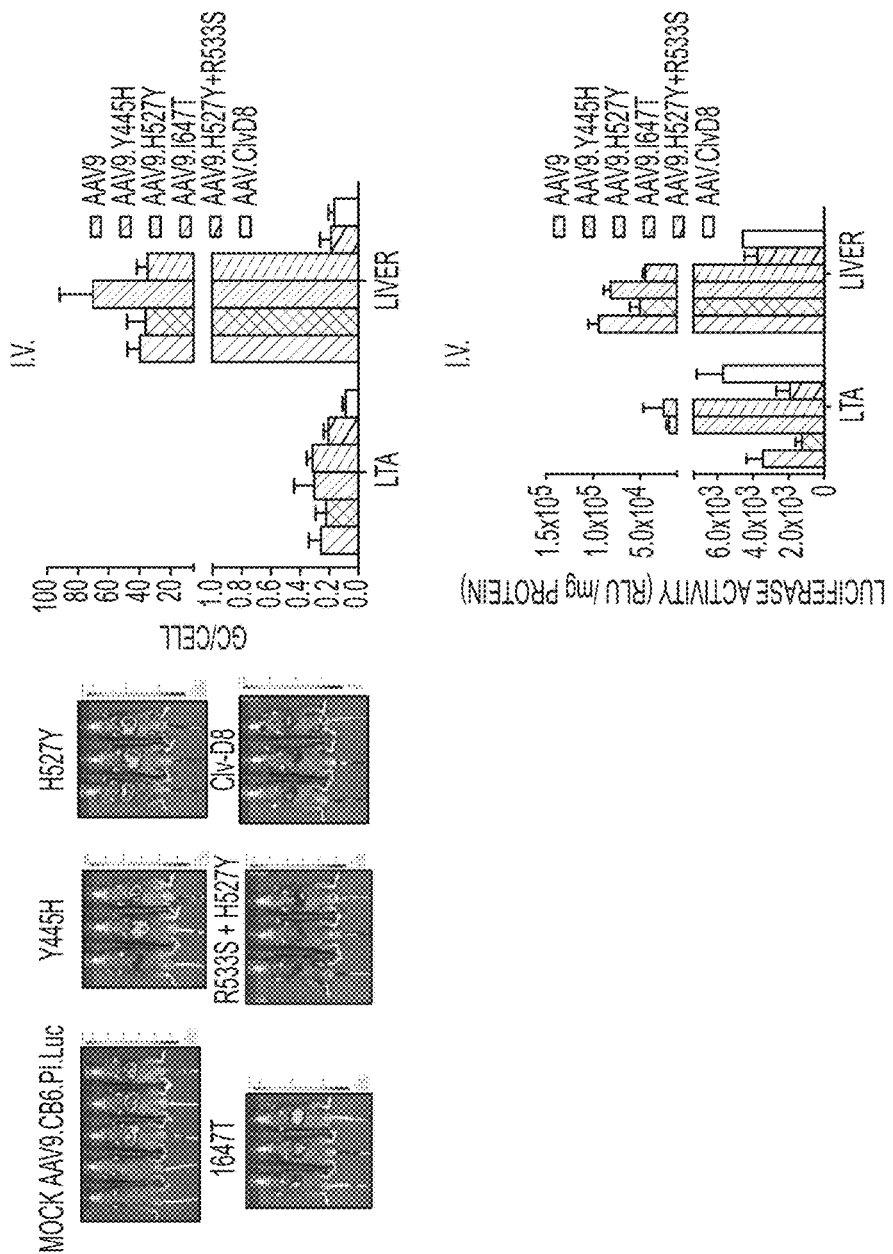
FIG. 5 depicts that AAV9.HR (derived from CLv-D8, Δ 2 a.a.)-mediated liver transgene expression is significantly lower than wtAAV9 after IV injection.
Figure 7:
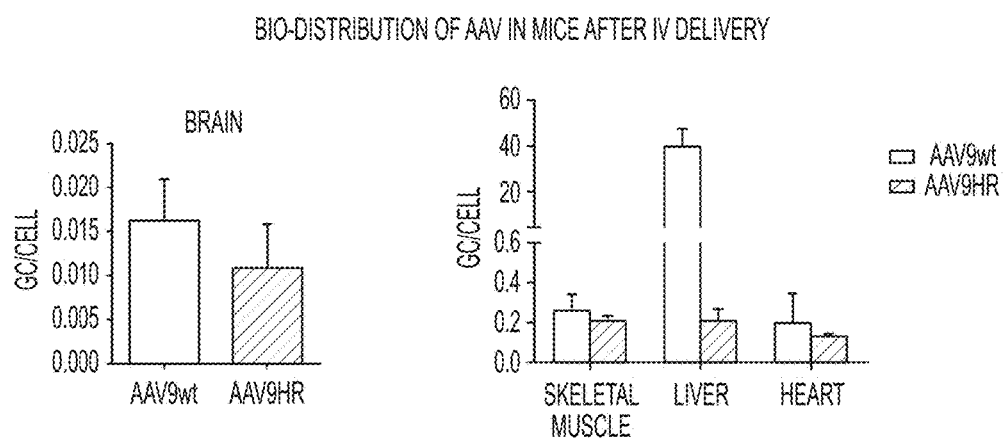
FIG. 7 depicts results of assays in which six-week old male C57BL/6 mice were injected via tail vein (1.0 e11 GC/mouse) with AAV9 wt and AAV9.HR encoding luciferase gene; four weeks later, specific organs were harvested for qPCR analysis.
Figure 8:
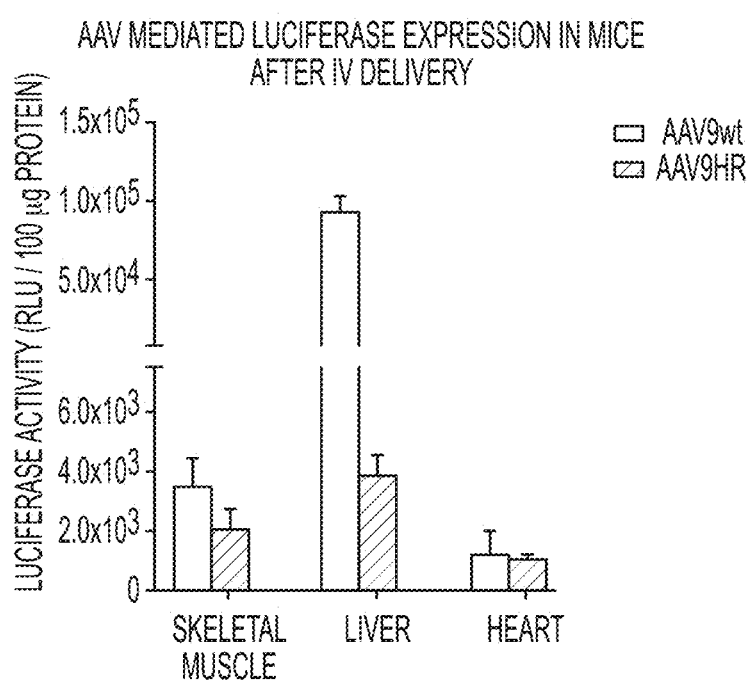
FIG. 8 depicts results of assays in which six-week old male C57BL/6 mice were injected via tail vein (1.0 e11 GC/mouse) with AAV9 wt and AAV9.HR encoding luciferase gene; four weeks later, specific organs were processed for luciferase activity analysis.

In another experiment, six-week old male C57BL/6 mice were injected via tail vein (1.0 e11 GC/mouse) with AAV9 and its mutant vectors encoding luciferase gene. Four weeks later, specific organs were harvested for qPCR and luciferase activity analysis. The results are depicted in FIG. 5. It was found that AAV9.HR-mediated liver transgene expression is much lower than wtAAV9 after IV injection. (See also FIGS. 7 and 8.)

Figure 6:
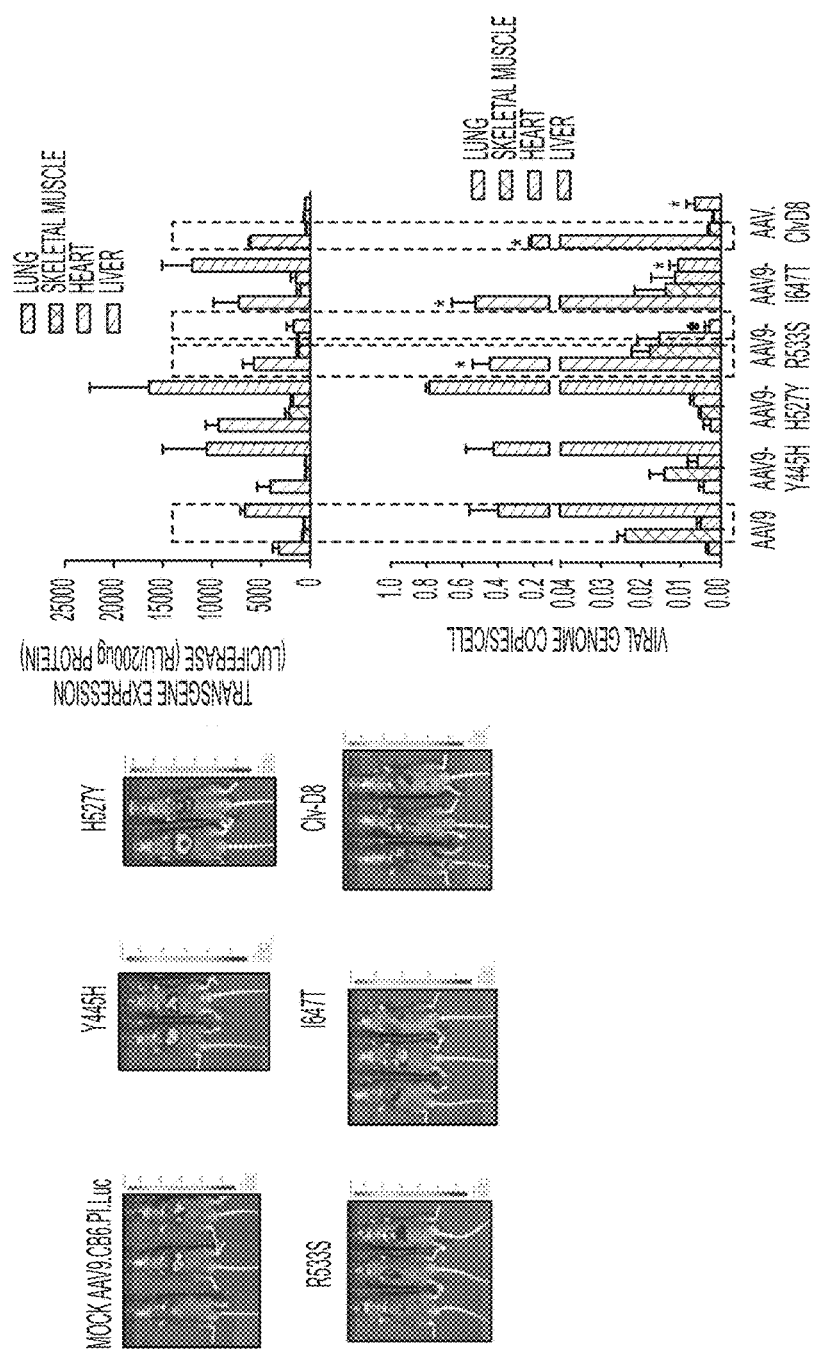
FIG. 6 depicts that AAV9.HR (derived from CLv-D8, Δ 2 a.a.)-mediated transgene expression is limited to lung after IN delivery.
Figure 9:
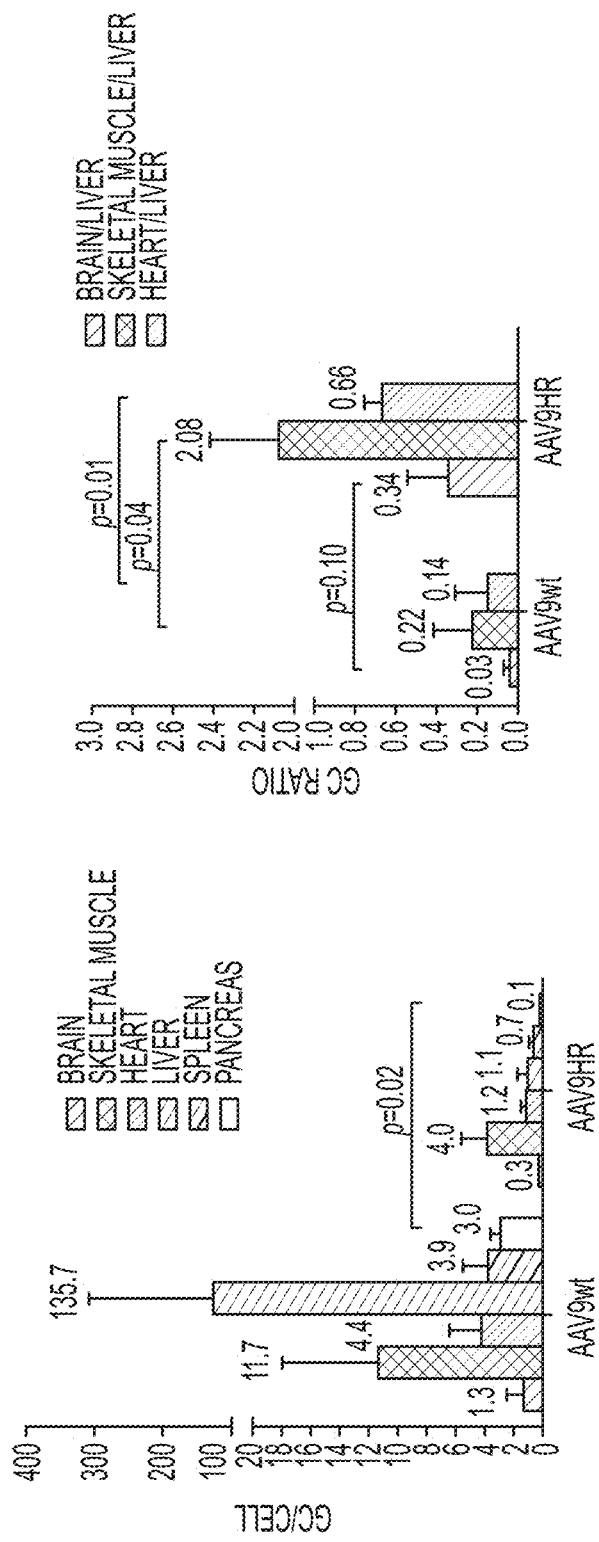
FIG. 9 depicts results of assays in which four-week-old C57BL/6 mice were injected (IV, Retro-orbital injection, 1e12 GC/mouse,) with scAAV9 wt.CB6.PI.EGFP (n=3) or scAAV9.HR.CB6.PI.EGFP (n=3); three weeks after administration, organs were collected and gDNA were extracted for qPCR analysis (Student's t-test (unpaired, two-tailed))

In another experiment, six-week old male C57BL/6 mice were injected via intranasal delivery (1.0 e11 GC/mouse) with AAV9 and its mutant vectors encoding luciferase gene. Four weeks later, specific organs were harvested for qPCR and luciferase activity analysis. The results are depicted in FIG. 6. It was found that AAV9.HR mediated transgene expression is limited in lung after IN delivery Further assays were conducted in which four-week-old C57BL/6 mice were injected (IV, Retro-orbital injection, 1e12 GC/mouse,) with scAAV9 wt.CB6.PI.EGFP (n=3) or scAAV9HR.CB6.PI.EGFP (n=3); three weeks after administration, organs were collected and gDNA were extracted for qPCR analysis (Student's t-test (unpaired, two-tailed)). The results of these assay are depicted in FIG. 9 and illustrate differences in the biodistribution of AAV9 compared with its mutant vectors following IV administration.

Figure 10:
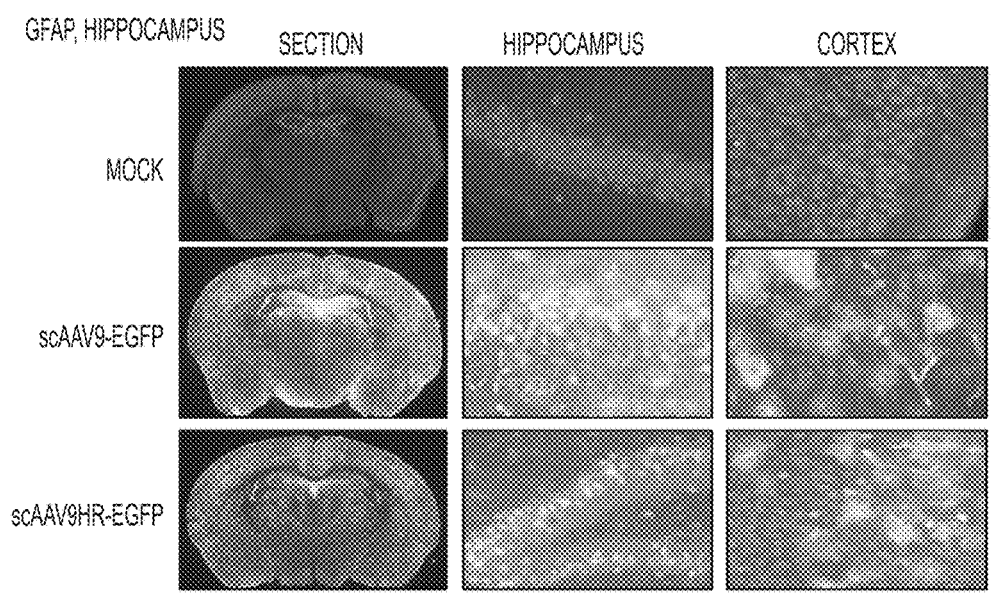
FIG. 10 depicts a comparison of AAV9 and AAV9.HR-mediated neuron transduction after IV (RO) delivery into D1 mice at $4\times10^{11}$ GC/mouse at 3 weeks post-injection.
Figure 11:
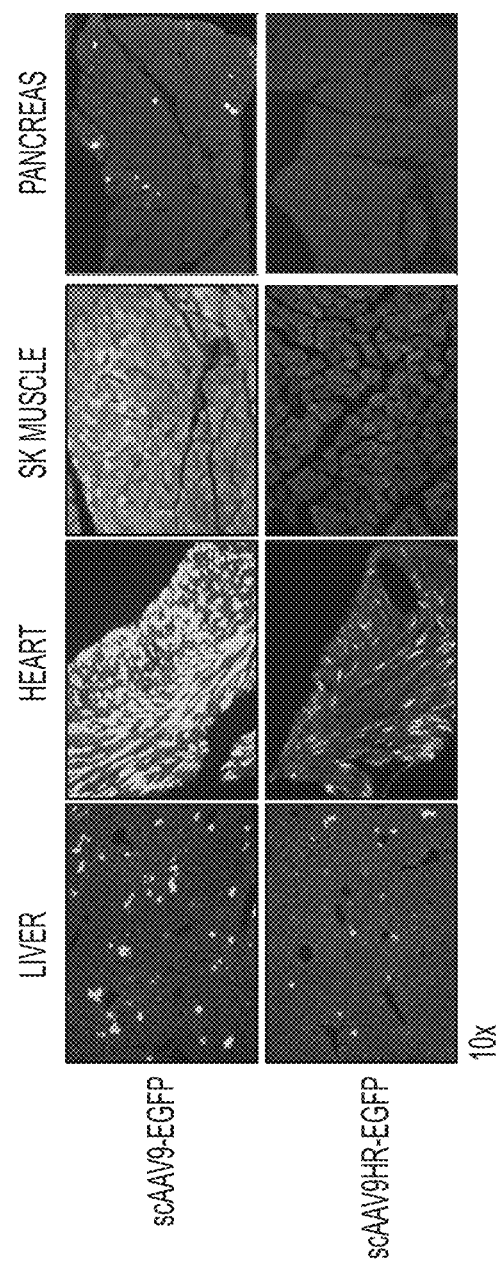
FIG. 11 depicts AAV9.HR mediated EGFP expression in brain after IV (RO) delivery into D1 mice at $4\times10^{11}$ GC/mouse at 3 weeks post-injection.

A comparison was also made of AAV9 and AAV9HR-mediated neuron transduction after IV (RO) delivery into D1 C57B16 mice at $4 \times 10^{11}$ GC/mouse. Gene transfer was analyzed at 3 weeks post-injection. Comparable CNS gene transfer between these two vectors, as depicted in FIG. 10. The rAAV9.HR even leads to more neuron transduction (high ration of transduced neuron/astrocyte) in certain areas (hippocampus, cortex etc.) It was also found that rAAV9.HR leads to peripheral organs detargeting, as depicted in FIG. 11.

Figure 12:
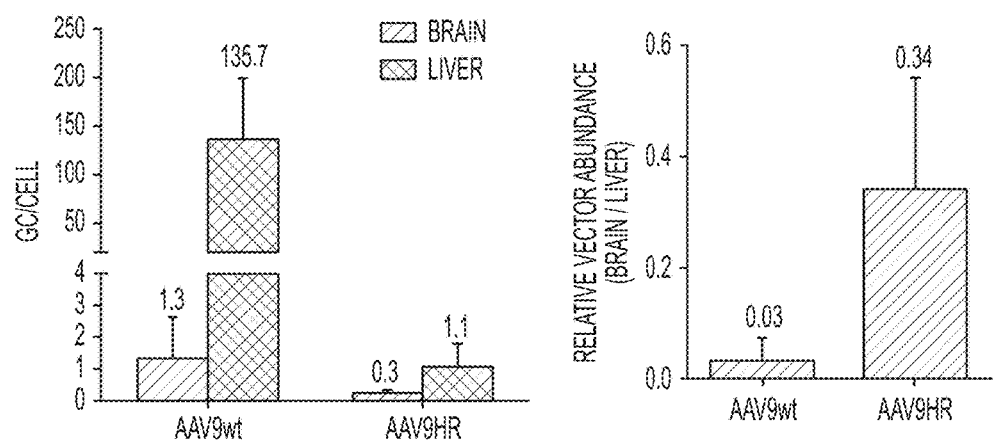
FIG. 12 depicts bio-distribution of AAV9 and AAV9.HR in adult mice (High Dose, eGFP)

A comparison was also made of AAV9 and AAV9HR-mediated biodistribution after IV (RO) delivery into D1 C57B16 mice at $1 \times 10^{12}$ GC/mouse (a higher dose). Gene transfer was analyzed at 3 weeks post-injection. (FIG. 12.) Comparable vector genome abundance in CNS in adult animals between rAAV9 and rAAV9HR. AAV9.HR leads to ~135-fold less vector genome abundance and significantly diminished transgene expression in liver (data not shown here) and other peripheral organs as compared to rAAV9

This work represents a significant advance in understanding vector biology of AAV9 and developing novel vectors with transduction efficiency similar to rAAV9 but improved safety profile for muscle and lung gene delivery and gene therapy of muscular, lung or other disorders.

Example 2

This example describes the use of AAV9.HR for CNS-directed gene therapy by intravenous (IV) injection.

Figure 13A:
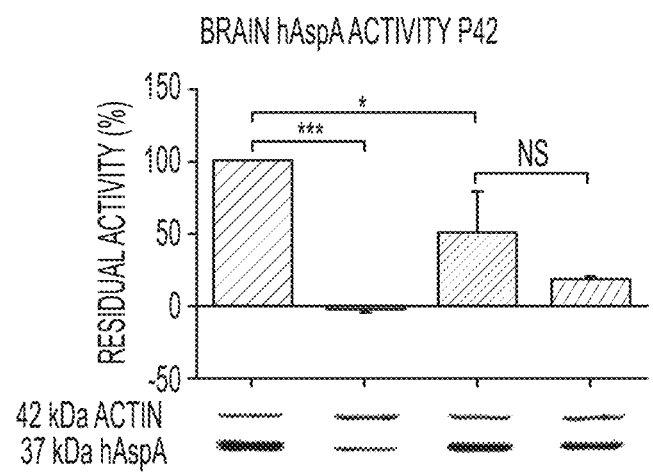
FIG. 13A-B depict hAspA enzyme expression (western blot) and activity after intravenous injection.
Figure 13B:
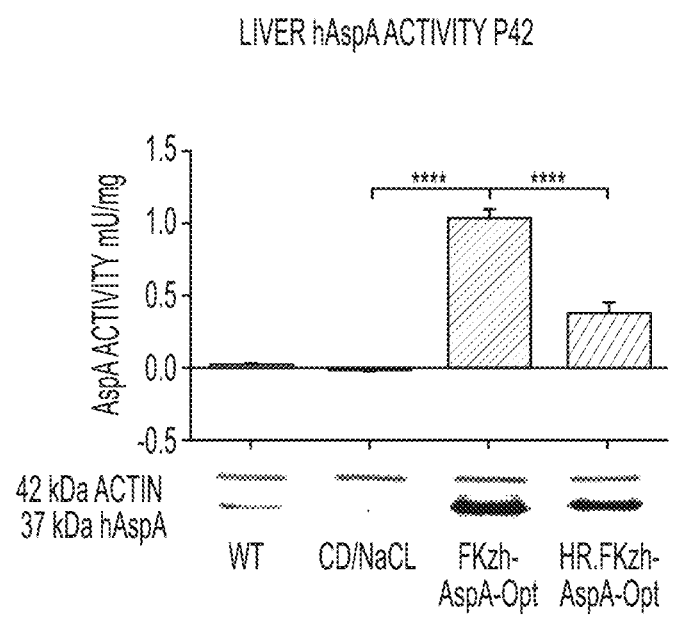

A mouse model of Canavan disease was used in this study. Healthy control (WT) and Canavan disease (CD) mice were administered a dose of $4 \times 10^{11}$ genome copies (GC) of an rAAV vector containing the human aspartoacylase (AspA) gene (AAV9-FKzhAspA-OPT or AAV9.HR-FKzhAspA-OPT) at age p1 by intravenous injection. All untreated CD mice died by week 4. Enzymatic assays and western blot were performed on WT and treated CD mice at age p42. Administration of either construct prevented death of CD mice. FIG. 13A shows no significant difference in enzymatic activity of AspA in the brains of mice administered AAV9 or AAV9.HR. However, administration of the AAV9.HR construct did result in less off-target (e.g. liver tissue) expression of ASPA compared to the AAV9 construct, as shown in FIG. 13B.

Figure 14A:
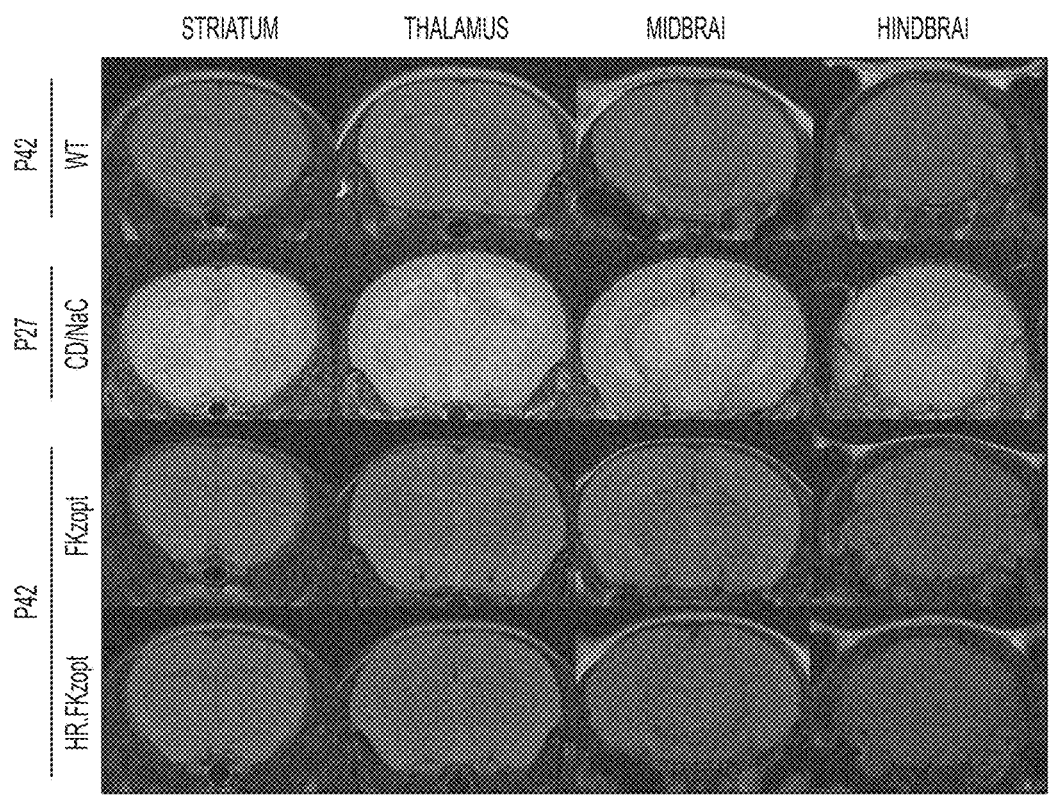
FIG. 14A-B depict MRI and MRS of mice at P42 after intravenous injection of AAV9 and AAV9.HR constructs. WT: wild-type; CD: Canavan disease; FKzhAspA-Opt: full kozak human AspA/AAV9 construct; HR.FKzhAspA-Opt: full kozak human AspA/AAV9.HR construct.
Figure 14B:
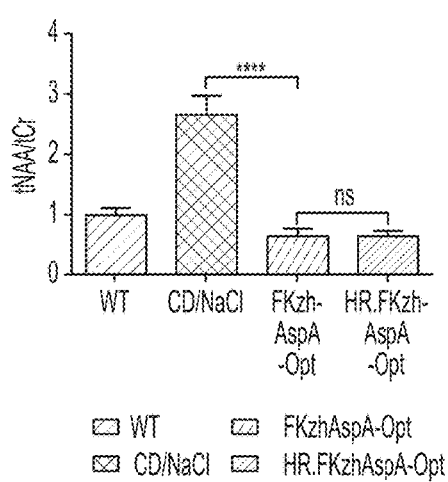

FIG. 14A shows similar localization patterns of hAspA expression in the brains of mice (age p42) after administration via AAV9 or AAV9.HR as measured by magnetic resonance imaging (MRI). Magnetic resonance spectroscopy (MRS) data demonstrates that hAspA expressed by both constructs is able to degrade N-acetyl-L-aspartic acid (NAA) (FIG. 14B).

Figure 15A:
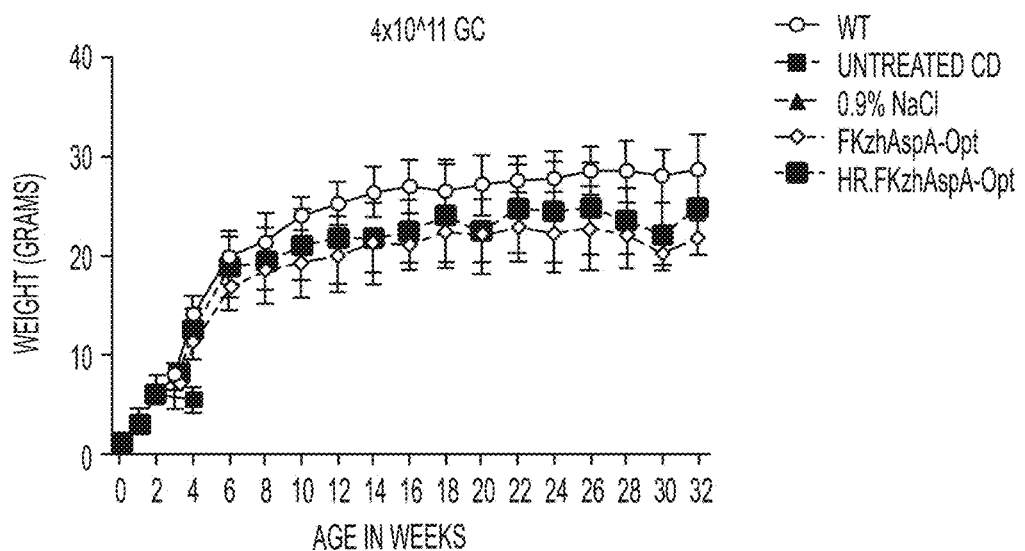
FIG. 15A-B depict weight and age of mice treated with vehicle (NaCl), FKzhAspA-Opt or HR.FKzhAspA-Opt by intravenous injection. Untreated CD mice died at 4 weeks of age.
Figure 15B:
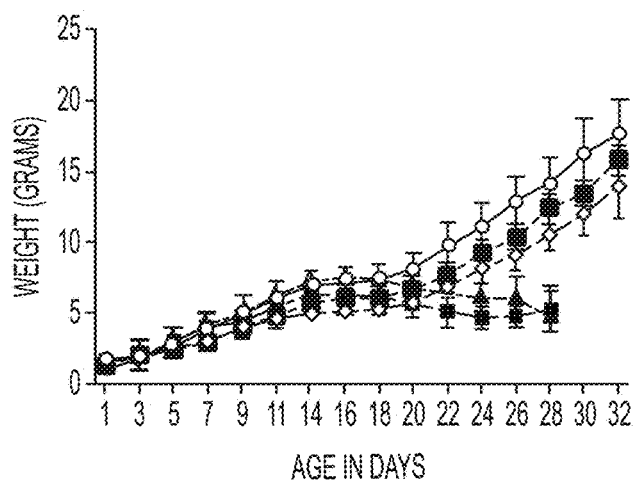

FIG. 15 shows that mice administered the HR.FKzhAspA-Opt construct showed no significant difference in growth (as measured by weight) to either wild-type (WT) or AAV9.FKzhAspA-Opt treated mice. Untreated and vehicle-only treated CD mice died by 4 weeks of age.

Figure 16:
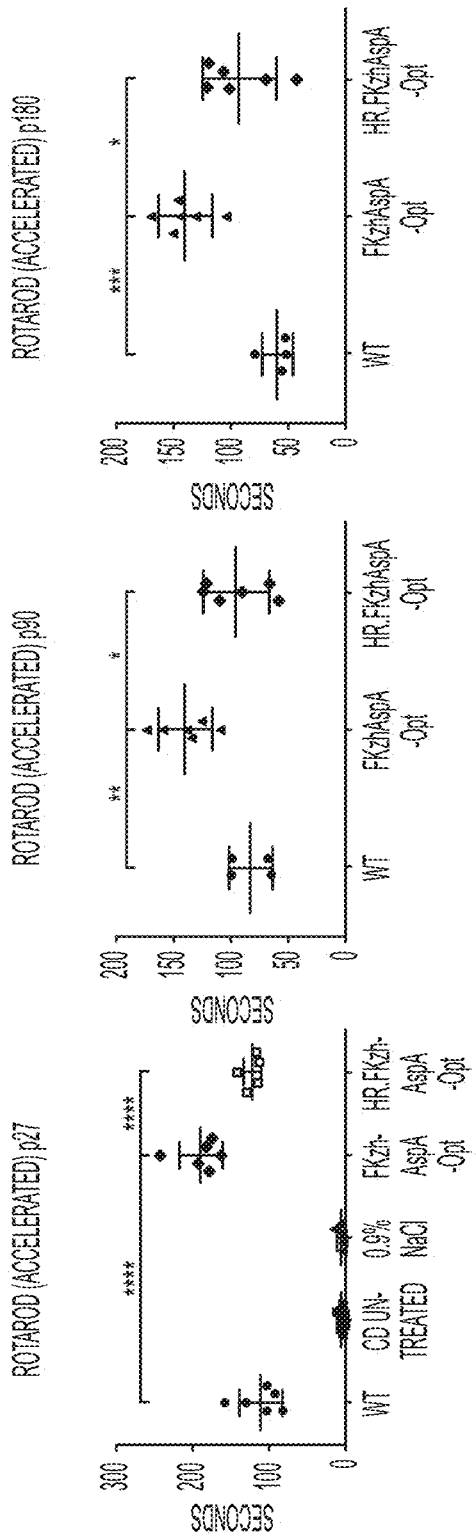
FIG. 16 depicts rotarod assessment of mice treated with vehicle (NaCl), FKzhAspA-Opt or HR.FKzhAspA-Opt by intravenous injection.
Figure 17:
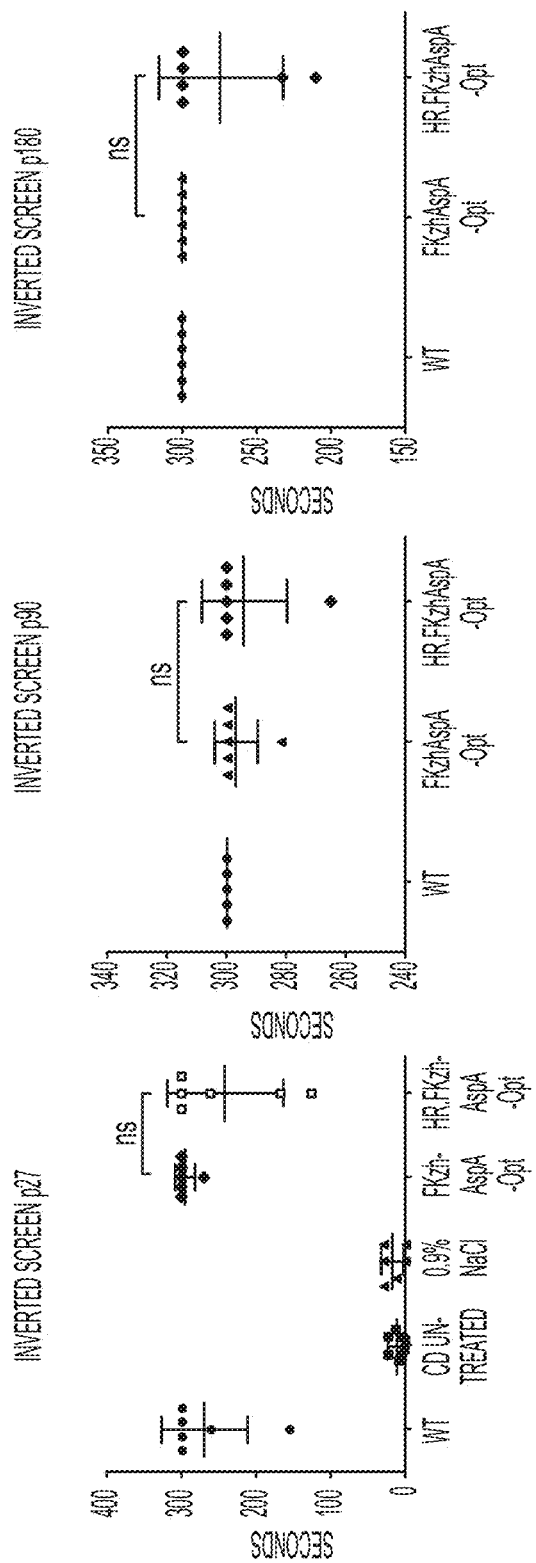
FIG. 17 depicts inverted screen assessment of mice treated with vehicle (NaCl), FKzhAspA-Opt or HR.FKzhAspA-Opt by intravenous injection.
Figure 18:
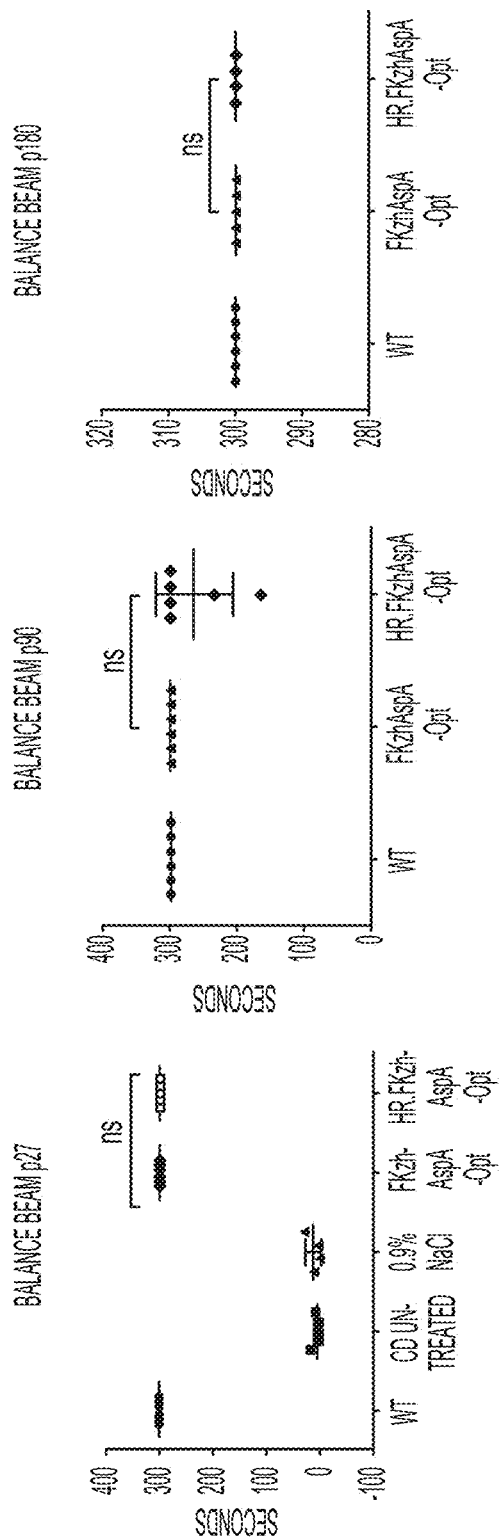
FIG. 18 depicts balance beam assessment of mice treated with vehicle (NaCl), FKzhAspA-Opt or HR.FKzhAspA-Opt by intravenous injection.

Administration of HR.FKzhAspA-Opt to CD mice also improved motor and behavioral phenotypes (FIGS. 16-18).

The results described above demonstrate that a CNS-targeted transgene (hASPA) delivered by an intravenously injected AAV9.HR vector is functionally expressed and localized in a similar manner to AAV9-delivered hAspA. However, the AAV.HR vecotor provides the advantage of lower off-target expression that AAV9. The results further show that AAV9.HR-hAspA is effective in prolonging the life and improving motor phenotype in a mouse model of Canavan disease.

Example 3

This example describes the expression of secreted tumor suppressor proteins using AAV.HR vectors for cancer therapy.

Activated oncogenes can induce cellular senescence and/or apoptosis in vitro and in vivo. Oncogene-induced senescence and/or apoptosis may be a cellular mechanism to prevent proliferation of cells at risk for neoplastic transformation. One gene involved in this process is the BRAF oncogene, which is a serine-threonine protein kinase. BRAF is a downstream effector of RAS and signals through the MAP kinase pathway. Oncogenic BRAF-activating mutations (e.g. BRAFV600E) substantially increase protein kinase activity, resulting in constitutive ERK signaling. These activating BRAF mutations are found in 70% of melanomas, 15% of colorectal cancers, 30% of ovarian cancers and 40% of papillary thyroid carcinomas. Several factors are involved in BRAF-mediated senescence/apoptosis (Table 1).

TABLE 1

| Factors involved in BRAF-mediated Senescence/Apoptosis | | | | |
|---|---|---|---|---|
| BIN1 | ILIR1 | RAP1GAP | TP53 | SMARCB1 |
| BNIP3L | HSPA9B | PEA15 | NF2 | |
| BUB1 | IGFBP7 | DMTF1 | FOXA1 | |
| MEN1 | HIRA | IRF1 | FBXO31 | |

Previous studies have shown IGFBP7 suppresses growth of BRAFV600E-positive tumors in mouse xenografts. Furthermore, IGFBP7 suppresses melanoma metastasis and enhances survival in mice with tumor xenografts. Another protein that has potential use as a cancer therapeutic is Sushi repeat-containing protein (SRPX), which has been shown to be down-regulated in many human lung cancers. SRPX is predicted to be a secreted protein.

Figure 19A:
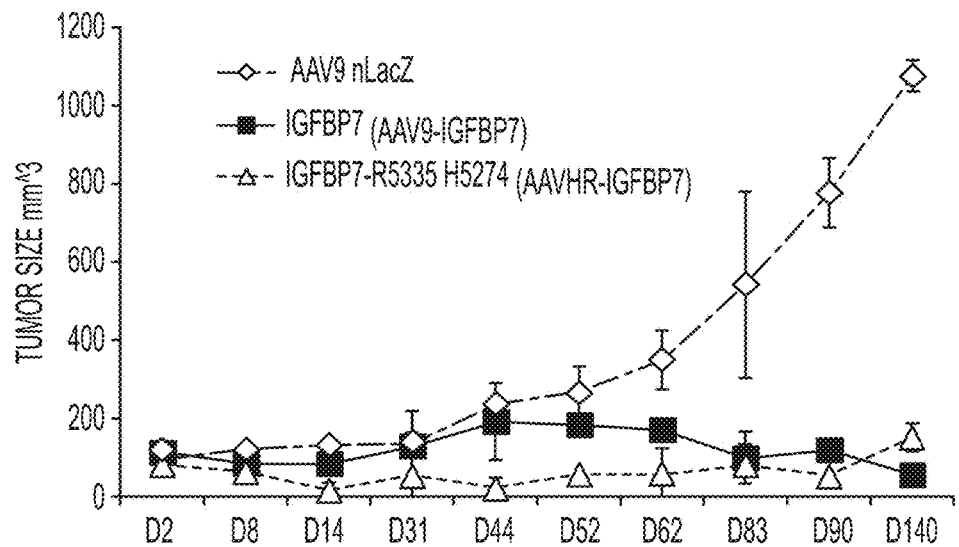
FIG. 19A-B depict AAV.HR-IGFBP7 delivery by intramuscular injection leads to tumor suppression in a dose dependent manner.
Figure 19B:
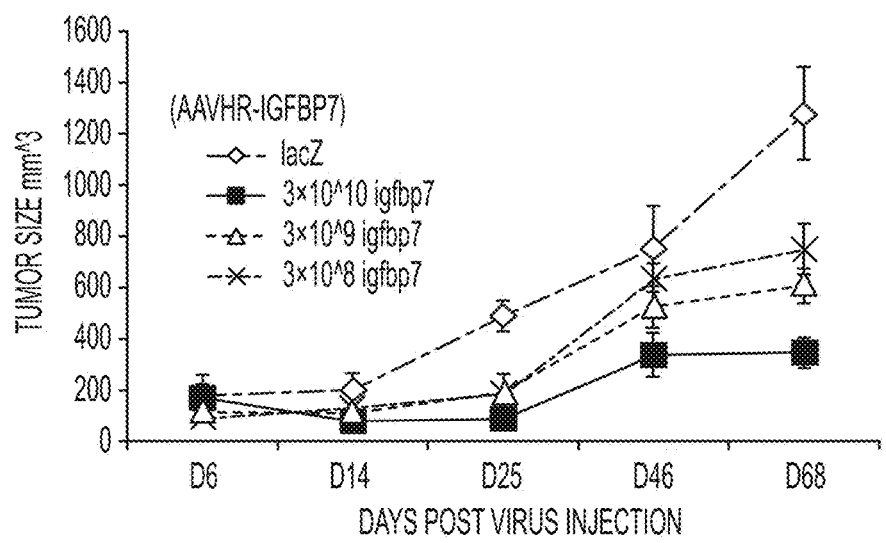
Figure 20A:
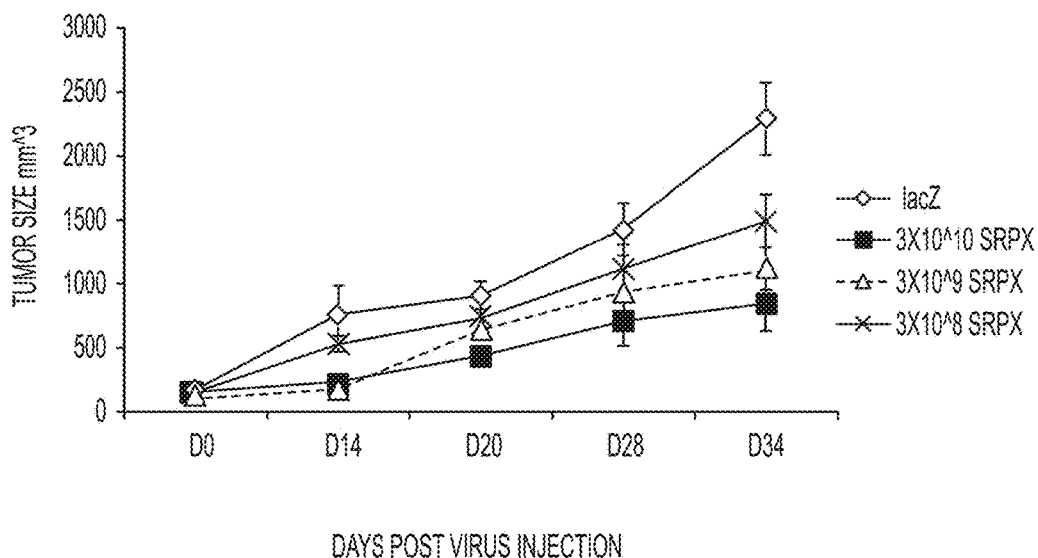
FIG. 20 depicts a dose curve for AAV.HR-SRPX induced tumor suppression in Balb/c Nu/Nu mice.
Figure 20B:
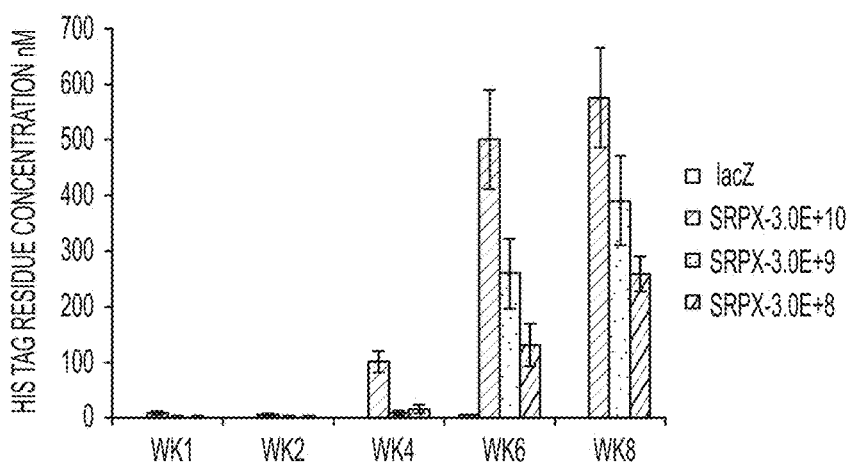
Figure 21:
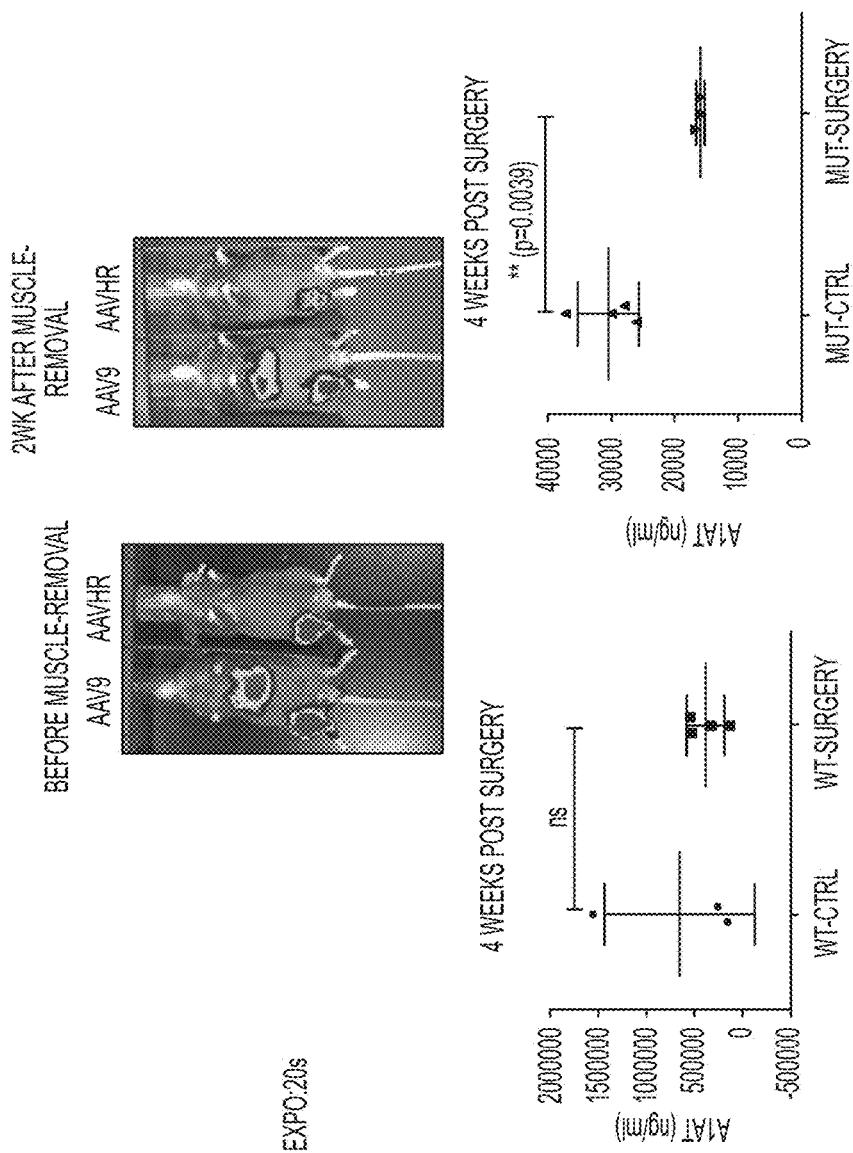
FIG. 21 depicts reversibility of AAV-mediated delivery of transgene.
Figure 22:
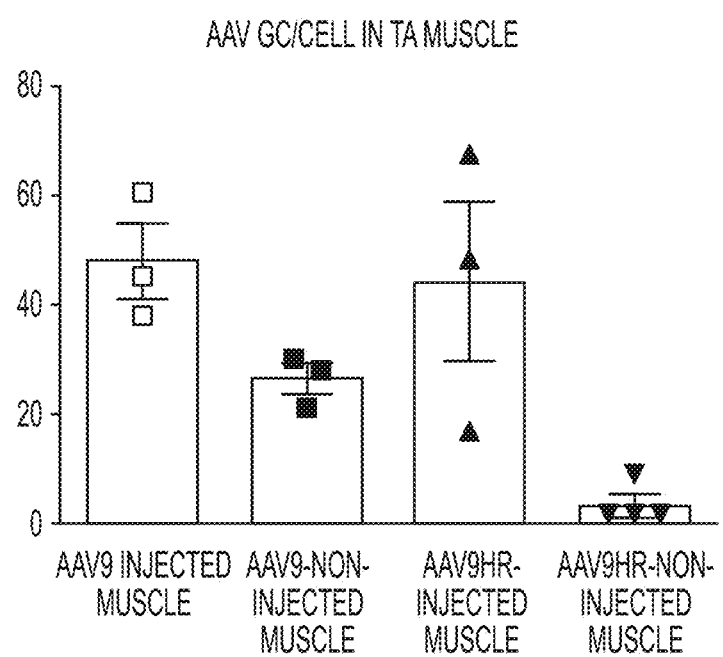
FIG. 22 depicts AAV genomes are restricted in injection site after delivery of AAV.HR vectors.

FIG. 19A shows that AAV9.HR-IGFBP7 has tumor suppression activity comparable to IGFBP delivered by WT AAV9. FIG. 19B shows the dose-dependent effect of AAV.HR-IGFBP7 on tumor suppression. The tumor suppressing activity of SRPX was also demonstrated. FIG. 20A shows the concentration-dependent effect of AAV9.HR-SRPX delivery on tumor size in Balb/c Nu/Nu mice. FIG. 20B shows dose-dependent expression of SRPX delivered by AAV9.HR vector. Due to the reduced transcytosis properties exhibited by the AAV9.HR vector, transgene delivery is reversible, whereas delivery by WT AAV9 vector persists even after removal of the injected tissue (FIG. 21). FIG. 22 demonstrates that AAV9.HR vector genomes do not migrate away from the tissue into which they are delivered.

Figure 23:
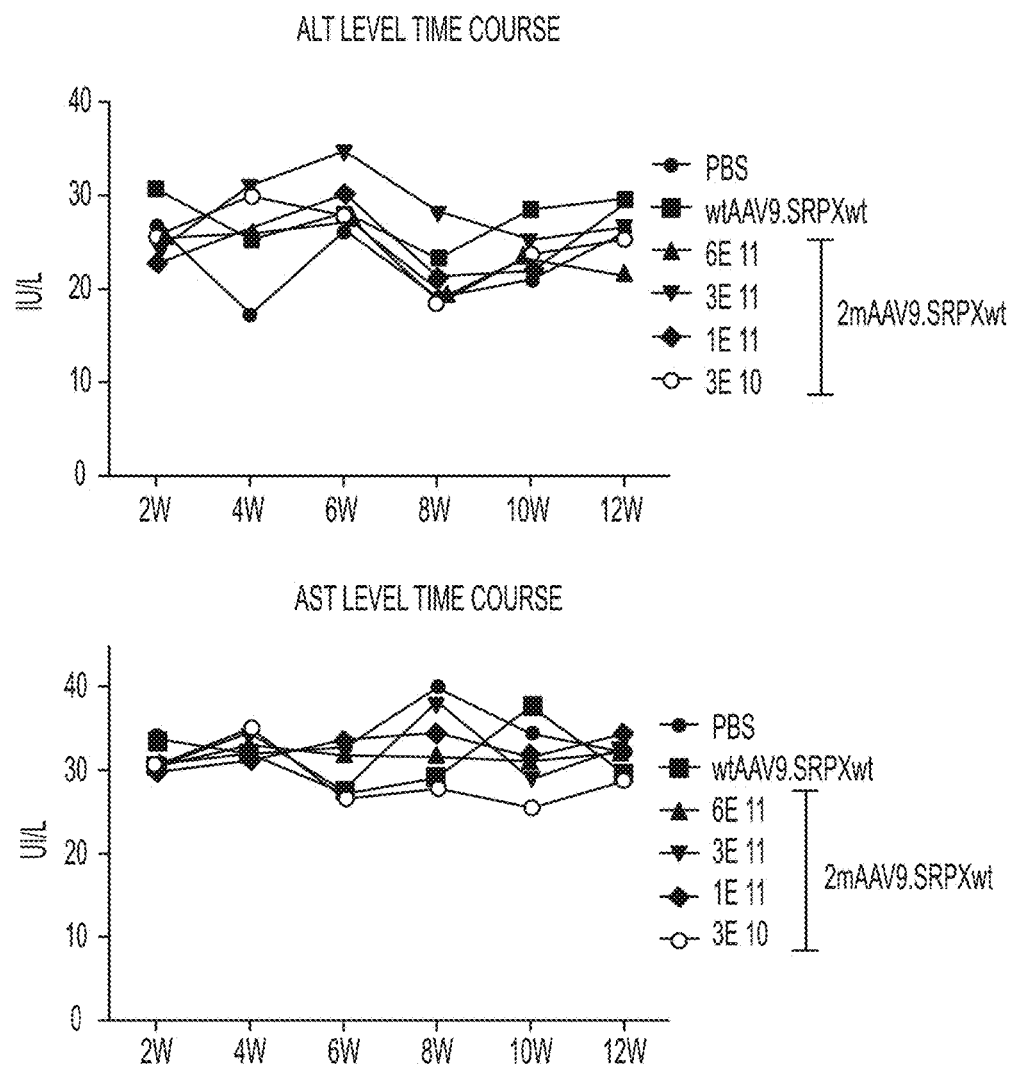
FIG. 23 depicts a toxicity assay for AAVHR.SRPXwt; ALT: Alanine transaminase; AST: aspartate aminotransferase.
Figure 24:
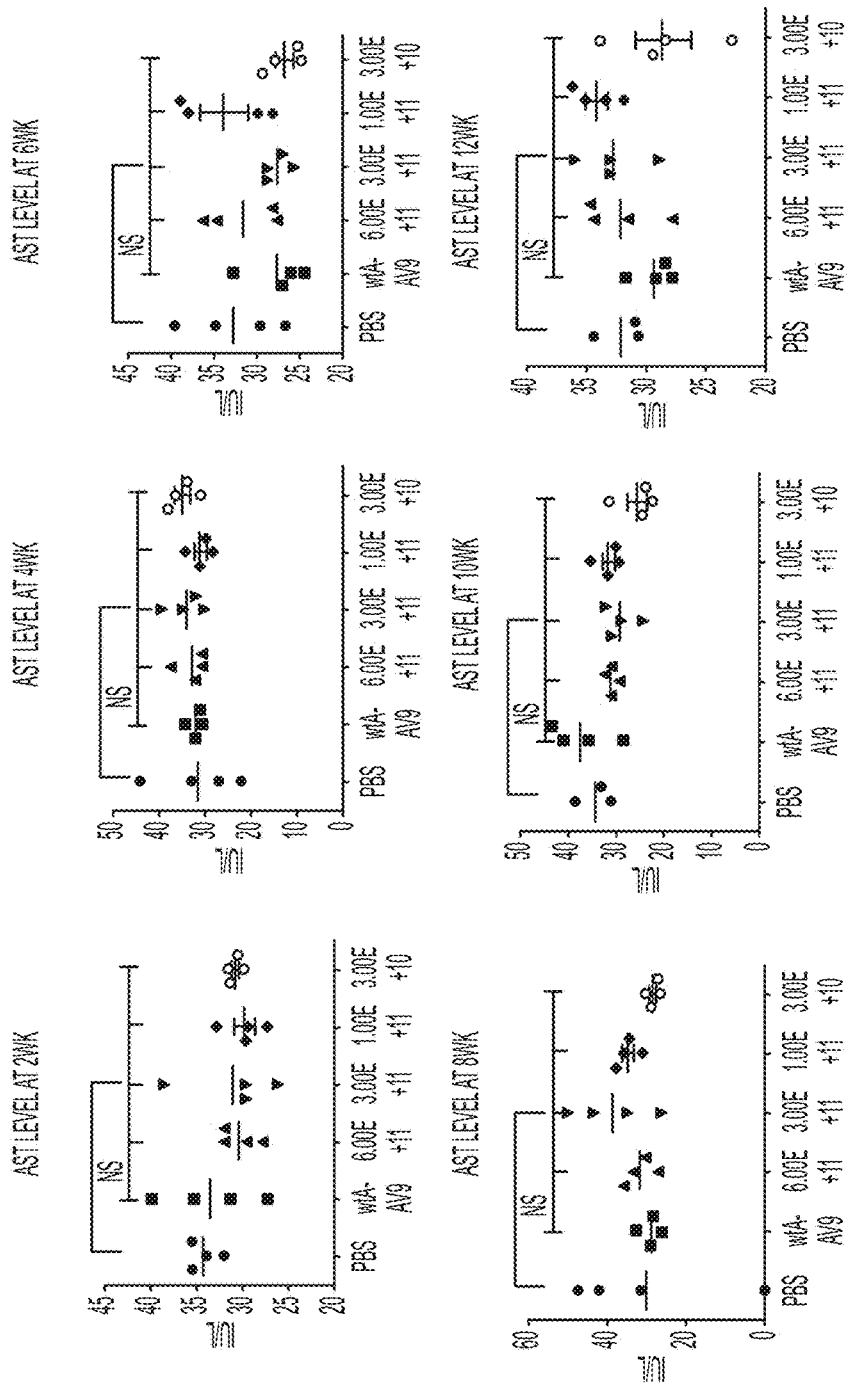
FIG. 24 depicts AST level at each time point (2-weeks to 12-weeks post-injection) of the toxicity assay.
Figure 25:
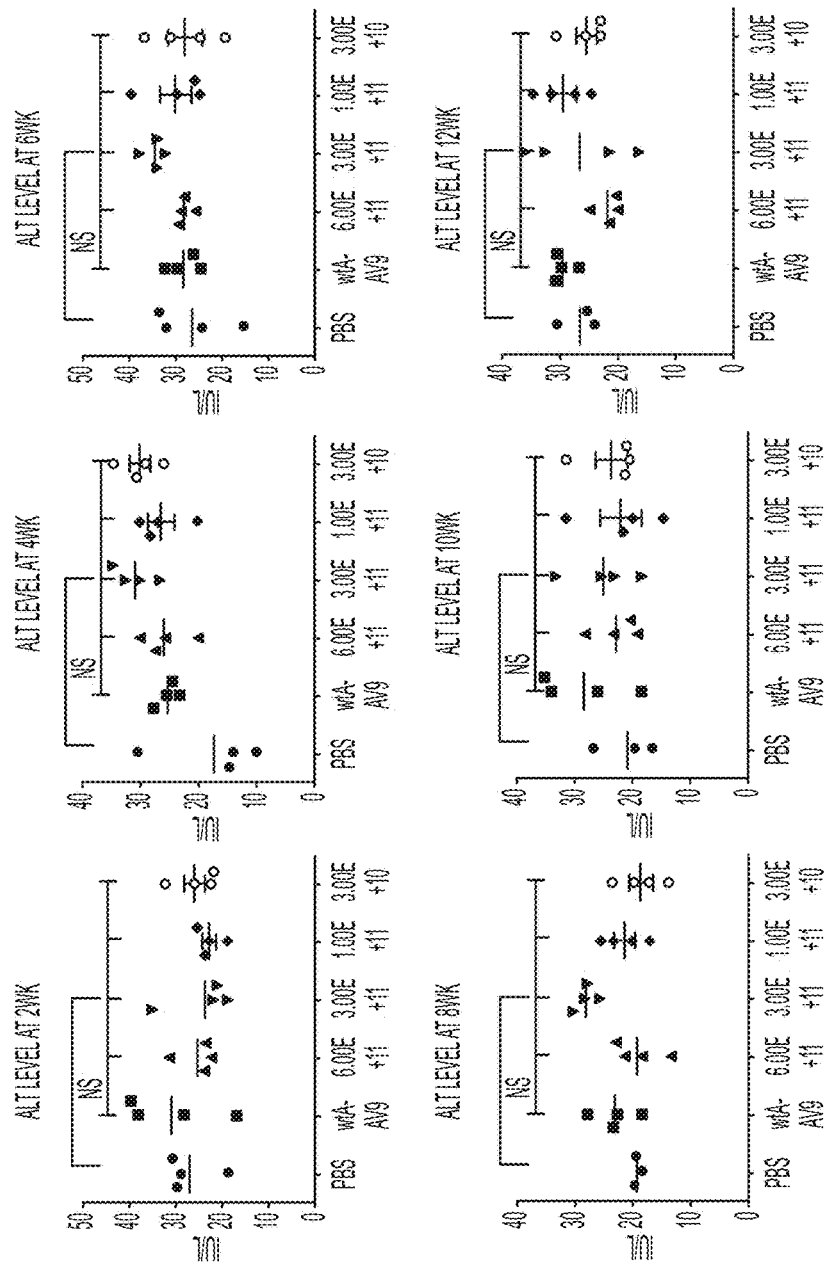
FIG. 25 depicts ALT level at each time point (2-weeks to 12-weeks post-injection) of the toxicity assay.

The toxicity of transgene delivery by AAV.HR vectors was assessed by measurement of alanine transaminase (ALT) and aspartate aminotransferase (AST) (FIG. 23-25). AAV9.HR exhibits a similar toxicity profile to WT AAV9 at several dosages. These results indicate that AAV.HR is a safe and efficient vector for muscle delivering of the secreted tumor suppressor proteins as cancer therapeutics.

SEQUENCES

>SEQ ID NO: 1-AAV9 CAPSID
MAADGYLPDWLEDNLSEGIREWWALKPGAPQPKANQQHQDNARGLVLPGY
KYLGPGNGLDKGEPVNAADAAALEHDKAYDQQLKAGDNPYLKYNHADAEF
QERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGS
LTMASGGGAPVADNNEGADGVGSSSGNWHCDSQWLGDRVITTSTRTWALP
TYNNHLYKQISNSTSGGSSNDNAYFGYSTPWGYFDFNRFHCHFSPRDWQR
LINNNWGFRPKRLNFKLFNIQVKEVTDNNGVKTIANNLTSTVQVFTDSDY
QLPYVLGSAHEGCLPPFPADVFMIPQYGYLTLNDGSQAVGRSSFYCLEYF
PSQMLRTGNNFQFSYEFENVPFHSSYAHSQSLDRLMNPLIDQYLYYLSKT
INGSGQNQQTLKFSVAGPSNMAVQGRNYIPGPSYRQQRVSTTVTQNNNSE
FAWPGASSWALNGRNSLMNPGPAMASHKEGEDRFFPLSGSLIFGKQGTGR
DNVDADKVMITNEEEIKTTNPVATESYGQVATNHQSAQAQAQTGWVQNQG
ILPGMVWQDRDVYLQGPIWAKIPHTDGNFHPSPLMGGFGMKHPPPQILIK
NTPVPADPPTAFNKDKLNSFITQYSTGQVSVEIEWELQKENSKRWNPEIQ
YTSNYYKSNNVEFAVNTEGVYSEPRPIGTRYLTRNL

>SEQ ID NO: 2-CLVD8 CAPSID
MAADGYLPDWLEDNLSEGIREWWALKPGAPQPKANQQHQDNARGLVLPGY
KYLGPGNGLDKGEPVNAADAAALEHDKAYDQQLKAGDNPYLKYNHADAEF
QERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGS
LTMASGGGAPVADNNEGADGVGSSSGNWHCDSQWLGDRVITTSTRTWALP
TYNNHLYKQISNSTSGGSSNDNAYFGYSTPWGYFDFNRFHCHFSPRDWQR
LINNNWGFRPKRLNFKLFNIQVKEVTDNNGVKTIANNLTSTVQVFTDSDY
QLPYVLGSAHEGCLPPFPADVFMIPQYGYLTLNDGSQAVGRSSFYCLEYF
PSQMLRTGNNFQFSYEFENVPFHSSYAHSQSLDRLMNPLIDQYLHYLSKT
INGSGQNQQTLKFSVAGSNMAVQGRNYIPGPSYRQQRVSTTVTQNNNSEF
AWPGASSWALNGRNSLMNPGPAMASYKEGEDSFFPLSGSLIFGKQGTGRD
NVDADKVMITNEEEIKTTNPVATESYGQVATNHQSAQAQAQTGWVQNQGI
LPGMVWQDRDVYLQGPIWAKIPHTDGNFHPSPLMGGFGMKHPPPQTLIKN
TPVPADPPTAFNKDKLNSFITQYSTGQVSVEIEWELQKENSKRWNPEIQY
TSNYYKSNNVEFAVNTEGVYSEPRPIGTRYLTRNL

>SEQ ID NO: 3-AAV9H CAPSID
MAADGYLPDWLEDNLSEGIREWWALKPGAPQPKANQQHQDNARGLVLPGY
KYLGPGNGLDKGEPVNAADAAALEHDKAYDQQLKAGDNPYLKYNHADAEF
QERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGS
LTMASGGGAPVADNNEGADGVGSSSGNWHCDSQWLGDRVITTSTRTWALP
TYNNHLYKQISNSTSGGSSNDNAYFGYSTPWGYFDFNRFHCHFSPRDWQR
LINNNWGFRPKRLNFKLFNIQVKEVTDNNGVKTIANNLTSTVQVFTDSDY
QLPYVLGSAHEGCLPPFPADVFMIPQYGYLTLNDGSQAVGRSSFYCLEYF
PSQMLRTGNNFQFSYEFENVPFHSSYAHSQSLDRLMNPLIDQYLYYLSKT
INGSGQNQQTLKFSVAGPSNMAVQGRNYIPGPSYRQQRVSTTVTQNNNSE
FAWPGASSWALNGRNSLMNPGPAMASYKEGEDRFFPLSGSLIFGKQGTGR
DNVDADKVMITNEEEIKTTNPVATESYGQVATNHQSAQAQAQTGWVQNQG
ILPGMVWQDRDVYLQGPIWAKIPHTDGNFHPSPLMGGFGMKHPPPQILIK
NTPVPADPPTAFNKDKLNSFITQYSTGQVSVEIEWELQKENSKRWNPEIQ
YTSNYYKSNNVEFAVNTEGVYSEPRPIGTRYLTRNL

>SEQ ID NO: 4-AAV9I CAPSID
MAADGYLPDWLEDNLSEGIREWWALKPGAPQPKANQQHQDNARGLVLPGY
KYLGPGNGLDKGEPVNAADAAALEHDKAYDQQLKAGDNPYLKYNHADAEF
QERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGS
LTMASGGGAPVADNNEGADGVGSSSGNWHCDSQWLGDRVITTSTRTWALP
TYNNHLYKQISNSTSGGSSNDNAYFGYSTPWGYFDFNRFHCHFSPRDWQR
LINNNWGFRPKRLNFKLFNIQVKEVTDNNGVKTIANNLTSTVQVFTDSDY
QLPYVLGSAHEGCLPPFPADVFMIPQYGYLTLNDGSQAVGRSSFYCLEYF
PSQMLRTGNNFQFSYEFENVPFHSSYAHSQSLDRLMNPLIDQYLYYLSKT
INGSGQNQQTLKFSVAGPSNMAVQGRNYIPGPSYRQQRVSTTVTQNNNSE
FAWPGASSWALNGRNSLMNPGPAMASHKEGEDRFFPLSGSLIFGKQGTGR
DNVDADKVMITNEEEIKTTNPVATESYGQVATNHQSAQAQAQTGWVQNQG
ILPGMVWQDRDVYLQGPIWAKIPHTDGNFHPSPLMGGFGMKHPPPQTLIK
NTPVPADPPTAFNKDKLNSFITQYSTGQVSVEIEWELQKENSKRWNPEIQ
YTSNYYKSNNVEFAVNTEGVYSEPRPIGTRYLTRNL

>SEQ ID NO: 5-AAV9R CAPSID
MAADGYLPDWLEDNLSEGIREWWALKPGAPQPKANQQHQDNARGLVLPGY
KYLGPGNGLDKGEPVNAADAAALEHDKAYDQQLKAGDNPYLKYNHADAEF
QERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGS
LTMASGGGAPVADNNEGADGVGSSSGNWHCDSQWLGDRVITTSTRTWALP
TYNNHLYKQISNSTSGGSSNDNAYFGYSTPWGYFDFNRFHCHFSPRDWQR
LINNNWGFRPKRLNFKLFNIQVKEVTDNNGVKTIANNLTSTVQVFTDSDY
QLPYVLGSAHEGCLPPFPADVFMIPQYGYLTLNDGSQAVGRSSFYCLEYF
PSQMLRTGNNFQFSYEFENVPFHSSYAHSQSLDRLMNPLIDQYLYYLSKT
INGSGQNQQTLKFSVAGPSNMAVQGRNYIPGPSYRQQRVSTTVTQNNNSE
FAWPGASSWALNGRNSLMNPGPAMASHKEGEDSFFPLSGSLIFGKQGTGR
DNVDADKVMITNEEEIKTTNPVATESYGQVATNHQSAQAQAQTGWVQNQG
ILPGMVWQDRDVYLQGPIWAKIPHTDGNFHPSPLMGGFGMKHPPPQILIK
NTPVPADPPTAFNKDKLNSFITQYSTGQVSVEIEWELQKENSKRWNPEIQ
YTSNYYKSNNVEFAVNTEGVYSEPRPIGTRYLTRNL

>SEQ ID NO: 6-AAV9Y CAPSID
MAADGYLPDWLEDNLSEGIREWWALKPGAPQPKANQQHQDNARGLVLPGY
KYLGPGNGLDKGEPVNAADAAALEHDKAYDQQLKAGDNPYLKYNHADAEF
QERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGS
LTMASGGGAPVADNNEGADGVGSSSGNWHCDSQWLGDRVITTSTRTWALP
TYNNHLYKQISNSTSGGSSNDNAYFGYSTPWGYFDFNRFHCHFSPRDWQR
LINNNWGFRPKRLNFKLFNIQVKEVTDNNGVKTIANNLTSTVQVFTDSDY
QLPYVLGSAHEGCLPPFPADVFMIPQYGYLTLNDGSQAVGRSSFYCLEYF
PSQMLRTGNNFQFSYEFENVPFHSSYAHSQSLDRLMNPLIDQYLHYLSKT
INGSGQNQQTLKFSVAGPSNMAVQGRNYIPGPSYRQQRVSTTVTQNNNSE
FAWPGASSWALNGRNSLMNPGPAMASHKEGEDRFFPLSGSLIFGKQGTGR
DNVDADKVMITNEEEIKTTNPVATESYGQVATNHQSAQAQAQTGWVQNQG
ILPGMVWQDRDVYLQGPIWAKIPHTDGNFHPSPLMGGFGMKHPPPQILIK
NTPVPADPPTAFNKDKLNSFITQYSTGQVSVEIEWELQKENSKRWNPEIQ
YTSNYYKSNNVEFAVNTEGVYSEPRPIGTRYLTRNL

>SEQ ID NO: 7-AAV9.HR CAPSID
MAADGYLPDWLEDNLSEGIREWWALKPGAPQPKANQQHQDNARGLVLPGY
KYLGPGNGLDKGEPVNAADAAALEHDKAYDQQLKAGDNPYLKYNHADAEF
QERLKEDTSFGGNLGRAVFQAKKRLLEPLGLVEEAAKTAPGKKRPVEQSP
QEPDSSAGIGKSGAQPAKKRLNFGQTGDTESVPDPQPIGEPPAAPSGVGS
LTMASGGGAPVADNNEGADGVGSSSGNWHCDSQWLGDRVITTSTRTWALP

TYNNHLYKQISNSTSGGSSNDNAYFGYSTPWGYFDFNRFHCHFSPRDWQR
LINNNWGFRPKRLNFKLFNIQVKEVTDNNGVKTIANNLTSTVQVFTDSDY
QLPYVLGSAHEGCLPPFPADVFMIPQYGYLTLNDGSQAVGRSSFYCLEYF
PSQMLRTGNNFQFSYEFENVPFHSSYAHSQSLDRLMNPLIDQYLYYLSKT
INGSGQNQQTLKFSVAGPSNMAVQGRNYIPGPSYRQQRVSTTVTQNNNSE
FAWPGASSWALNGRNSLMNPGPAMASYKEGEDSFFPLSGSLIFGKQGTGR
DNVDADKVMITNEEEIKTTNPVATESYGQVATNHQSAQAQAQTGWVQNQG
ILPGMVWQDRDVYLQGPIWAKIPHTDGNFHPSPLMGGFGMKHPPPQILIK
NTPVPADPPTAFNKDKLNSFITQYSTGQVSVEIEWELQKENSKRWNPEIQ
YTSNYYKSNNVEFAVNTEGVYSEPRPIGTRYLTRNL

>SEQ ID NO: 8-NUCLEIC ACID ENCODING AAV9 CAPSID
ATGGCTGCCGATGGTTATCTTCCAGATTGGCTCGAGGACAACCTTAGTGA
AGGAATTCGCGAGTGGTGGGCTTTGAAACCTGGAGCCCCTCAACCCAAGG
CAAATCAACAACATCAAGCAACGCTCGAGGTCTTGTGCTTCCGGGTTAC
AAATACCTTGGACCCGGCAACGGACTCGACAAGGGGGAGCCGGTCAACGC
AGCAGACGCGGCGGCCCTCGAGCACGACAAGGCCTACGACCAGCAGCTCA
AGGCCGGAGACAACCCGTACCTCAAGTACAACCACGCCGACGCCGAGTTC
CAGGAGCGGCTCAAAGAAGATACGTCTTTTGGGGGCAACCTCGGGCGAGC
AGTCTTCCAGGCCAAAAGAGGCTTCTTGAACCTCTTGGTCTGGTTGAGG
AAGCGGCTAAGACGGCTCCTGGAAAGAAGAGGCCTGTAGAGCAGTCTCCT
CAGGAACCGGACTCCTCCGCGGGTATTGGCAAATCGGGTGCACAGCCCGC
TAAAAAGAGACTCAATTTCGGTCAGACTGGCGACACAGAGTCAGTCCCAG
ACCCTCAACCAATCGGAGAACCTCCCGCAGCCCCCTCAGGTGTGGGATCT
CTTACAATGGCTTCAGGTGGTGGCGCACCAGTGGCAGACAATAACGAAGG
TGCCGATGGAGTGGGTAGTTCCTCGGGAAATTGGCATTGCGATTCCCAAT
GGCTGGGGGACAGAGTCATCACCACCAGCACCCGAACCTGGGCCCTGCCC
ACCTACAACAATCACCTCTACAAGCAAATCTCCAACAGCACATCTGGAGG
ATCTTCAAATGACAACGCCTACTTCGGCTACAGCACCCCCTGGGGGTATT
TTGACTTCAACAGATTCCACTGCCACTTCTCACCACGTGACTGGCAGCGA
CTCATCAACAACAACTGGGGATTCCGGCCTAAGCGACTCAACTTCAAGCT
CTTCAACATTCAGGTCAAAGAGGTTACGGACAACAATGGAGTCAAGACCA
TCGCCAATAACCTTACCAGCACGGTCCAGGTCTTCACGGACTCAGACTAT
CAGCTCCCGTACGTGCTCGGGTCGGCTCACGAGGGCTGCCTCCCGCCGTT
CCCAGCGGACGTTTTCATGATTCCTCAGTACGGGTATCTGACGCTTAATG
ATGGAAGCCAGGCCGTGGGTCGTTCGTCCTTTTACTGCCTGGAATATTTC
CCGTCGCAAATGCTAAGAACGGGTAACAACTTCCAGTTCAGCTACGAGTT
TGAGAACGTACCTTTCCATAGCAGCTACGCTCACAGCCAAAGCCTGGACC
GACTAATGAATCCACTCATCGACCAATACTTGTACTATCTCTCAAAGACT
ATTAACGGTTCTGGACAGAATCAACAAACGCTAAAATTCAGTGTGGCCGG
ACCCAGCAACATGGCTGTCCAGGGAAGAAACTACATACCTGGACCCAGCT
ACCGACAACAACGTGTCTCAACCACTGTGACTCAAAACAACAACAGCGAA
TTTGCTTGGCCTGGAGCTTCTTCTTGGGCTCTCAATGGACGTAATAGCTT
GATGAATCCTGGACCTGCTATGGCCAGCCACAAAGAAGGAGAGGACCGTT
TCTTTCCTTTGTCTGGATCTTTAATTTTTGGCAAACAAGGAACTGGAAGA
GACAACGTGGATGCGGACAAAGTCATGATAACCAACGAAGAAGAAATTAA
AACTACTAACCCGGTAGCAACGGAGTCCTATGGACAAGTGGCCACAAACC
ACCAGAGTGCCCAAGCACAGGCGCAGACCGGCTGGGTTCAAAACCAAGGA
ATACTTCCGGGTATGGTTTGGCAGGACAGAGATGTGTACCTGCAAGGACC
CATTTGGGCCAAAATTCCTCACACGGACGGCAACTTTCACCCTTCTCCGC
TGATGGGAGGGTTTGGAATGAAGCACCCGCCTCCTCAGATCCTCATCAAA
AACACACCTGTACCTGCGGATCCTCCAACGGCTTCAACAAGGACAAGCT
GAACTCTTTCATCACCCAGTATTCTACTGGCCAAGTCAGCGTGGAGATCG
AGTGGGAGCTGCAGAAGGAAAACAGCAAGCGCTGGAACCCGGAGATCCAG
TACACTTCCAACTATTACAAGTCTAATAATGTTGAATTTGCTGTTAATAC
TGAAGGTGTATATAGTGAACCCCGCCCCATTGGCACCAGATACCTGACTC
GTAATCTG

>SEQ ID NO: 9-NUCLEIC ACID ENCODING CLVD8 CAPSID
ATGGCTGCCGATGGTTATCTTCCAGATTGGCTCGAGGACAACCTTAGTGA
AGGAATTCGCGAGTGGTGGGCTTTGAAACCTGGAGCCCCTCAACCCAAGG
CAAATCAACAACATCAAGCAACGCTCGAGGTCTTGTGCTTCCGGGTTAC
AAATACCTTGGACCCGGCAACGGACTCGACAAGGGGGAGCCGGTCAACGC
AGCAGACGCGGCGGCCCTCGAGCACGACAAGGCCTACGACCAGCAGCTCA
AGGCCGGAGACAACCCGTACCTCAAGTACAACCACGCCGACGCCGAGTTC
CAGGAGCGGCTCAAAGAAGATACGTCTTTTGGGGGCAACCTCGGGCGAGC
AGTCTTCCAGGCCAAAAGAGGCTTCTTGAACCTCTTGGTCTGGTTGAGG
AAGCGGCTAAGACGGCTCCTGGAAAGAAGAGGCCTGTAGAGCAGTCTCCT
CAGGAACCGGACTCCTCCGCGGGTATTGGCAAATCGGGTGCACAGCCCGC
TAAAAAGAGACTCAATTTCGGTCAGACTGGCGACACAGAGTCAGTCCCAG
ACCCTCAACCAATCGGAGAACCTCCCGCAGCCCCCTCAGGTGTGGGATCT
CTTACAATGGCTTCAGGTGGTGGCGCACCAGTGGCAGACAATAACGAAGG
TGCCGATGGAGTGGGTAGTTCCTCGGGAAATTGGCATTGCGATTCCCAAT
GGCTGGGGGACAGAGTCATCACCACCAGCACCCGAACCTGGGCCCTGCCC
ACCTACAACAATCACCTCTACAAGCAAATCTCCAACAGCACATCTGGAGG
ATCTTCAAATGACAACGCCTACTTCGGCTACAGCACCCCCTGGGGGTATT
TTGACTTCAACAGATTCCACTGCCACTTCTCACCACGTGACTGGCAGCGA
CTCATCAACAACAACTGGGGATTCCGGCCTAAGCGACTCAACTTCAAGCT
CTTCAACATTCAGGTCAAAGAGGTTACGGACAACAATGGAGTCAAGACCA
TCGCCAATAACCTTACCAGCACGTGGCCAGGTCTTCACGGACTCAGACTAT
CAGCTCCCGTACGTGCTCGGGTCGGCTCACGAGGGCTGCCTCCCGCCGTT
CCCAGCGGACGTTTTCATGATTCCTCAGTACGGGTATCTGACGCTTAATG
ATGGAAGCCAGGCCGTGGGTCGTTCGTCCTTTTACTGCCTGGAATATTTC
CCGTCGCAAATGCTAAGAACGGGTAACAACTTCCAGTTCAGCTACGAGTT
TGAGAACGTACCTTTCCATAGCAGCTACGCTCACAGCCAAAGCCTGGACC
GACTAATGAATCCACTCATCGACCAATACTTGTACTATCTCTCAAAGACT
ATTAACGGTTCTGGACAGAATCAACAAACGCTAAAATTCAGTGTGGCCGG
ACCCAGCAACATGGCTGTCCAGGGAAGAAACTACATACCTGGACCCAGCT
CCGACAACAACGTGTCTCAACCACTGTGACTCAAAACAACAACAGCGAAT
TTGCTTGGCCTGGAGCTTCTTCTTGGGCTCTCAATGGACGTAATAGCTTG
ATGAATCCTGGACCTGCTATGGCCAGCTACAAAGAAGGAGAGGACCGTTT
CTTTCCTTTGTCTGGATCTTTAATTTTTGGCAAACAAGGAACTGGAAGAC
AACGTGGATGCGGACAAAGTCATGATAACCAACGAAGAAGAAATTAAAAC
TACTAACCCGGTAGCAACGGAGTCCTATGGACAAGTGGCCACAAACCACC
AGAGTGCCCAAGCACAGGCGCAGACCGGCTGGGTTCAAAACCAAGGAATA
CTTCCGGGTATGGTTTGGCAGGACAGAGATGTGTACCTGCAAGGACCCAT
TTGGGCCAAAATTCCTCACACGGACGGCAACTTTCACCCTTCTCCGCTGA
TGGGAGGGTTTGGAATGAAGCACCCGCCTCCTCAGATCCTCATCAAAACA
CACCTGTACCTGCGGATCCTCCAACGGCTTCAACAAGGACAAGCTGAACT
CTTTCATCACCCAGTATTCTACTGGCCAAGTCAGCGTGGAGATCGAGTGG
GAGCTGCAGAAGGAAAACAGCAAGCGCTGGAACCCGGAGATCCAGTACAC
TTCCAACTATTACAAGTCTAATAATGTTGAATTTGCTGTTAATACTGAAG
GTGTATATAGTGAACCCCGCCCCATTGGCACCAGATACCTGACTCGTAAT
CTG

>SEQ ID NO: 10-NUCLEIC ACID ENCODING AAV9H CAPSID
ATGGCTGCCGATGGTTATCTTCCAGATTGGCTCGAGGACAACCTTAGTGA
AGGAATTCGCGAGTGGTGGGCTTTGAAACCTGGAGCCCCTCAACCCAAGG
CAAATCAACAACATCAAGCAACGCTCGAGGTCTTGTGCTTCCGGGTTAC
AAATACCTTGGACCCGGCAACGGACTCGACAAGGGGGAGCCGGTCAACGC
AGCAGACGCGGCGGCCCTCGAGCACGACAAGGCCTACGACCAGCAGCTCA
AGGCCGGAGACAACCCGTACCTCAAGTACAACCACGCCGACGCCGAGTTC
CAGGAGCGGCTCAAAGAAGATACGTCTTTTGGGGGCAACCTCGGGCGAGC
AGTCTTCCAGGCCAAAAGAGGCTTCTTGAACCTCTTGGTCTGGTTGAGG
AAGCGGCTAAGACGGCTCCTGGAAAGAAGAGGCCTGTAGAGCAGTCTCCT
CAGGAACCGGACTCCTCCGCGGGTATTGGCAAATCGGGTGCACAGCCCGC
TAAAAAGAGACTCAATTTCGGTCAGACTGGCGACACAGAGTCAGTCCCAG
ACCCTCAACCAATCGGAGAACCTCCCGCAGCCCCCTCAGGTGTGGGATCT
CTTACAATGGCTTCAGGTGGTGGCGCACCAGTGGCAGACAATAACGAAGG
TGCCGATGGAGTGGGTAGTTCCTCGGGAAATTGGCATTGCGATTCCCAAT
GGCTGGGGGACAGAGTCATCACCACCAGCACCCGAACCTGGGCCCTGCCC
ACCTACAACAATCACCTCTACAAGCAAATCTCCAACAGCACATCTGGAGG
ATCTTCAAATGACAACGCCTACTTCGGCTACAGCACCCCCTGGGGGTATT
TTGACTTCAACAGATTCCACTGCCACTTCTCACCACGTGACTGGCAGCGA
CTCATCAACAACAACTGGGGATTCCGGCCTAAGCGACTCAACTTCAAGCT
CTTCAACATTCAGGTCAAAGAGGTTACGGACAACAATGGAGTCAAGACCA
TCGCCAATAACCTTACCAGCACGGTCCAGGTCTTCACGGACTCAGACTAT
CAGCTCCCGTACGTGCTCGGGTCGGCTCACGAGGGCTGCCTCCCGCCGTT
CCCAGCGGACGTTTTCATGATTCCTCAGTACGGGTATCTGACGCTTAATG
ATGGAAGCCAGGCCGTGGGTCGTTCGTCCTTTTACTGCCTGGAATATTTC
CCGTCGCAAATGCTAAGAACGGGTAACAACTTCCAGTTCAGCTACGAGTT
TGAGAACGTACCTTTCCATAGCAGCTACGCTCACAGCCAAAGCCTGGACC
GACTAATGAATCCACTCATCGACCAATACTTGTACTATCTCTCAAAGACT
ATTAACGGTTCTGGACAGAATCAACAAACGCTAAAATTCAGTGTGGCCGG
ACCCAGCACATGGCTGTCCAGGGAAGAAACTACATACCTGGACCCAGCTC
CGACAACAACGTGTCTCAACCACTGTGACTCAAAACAACAACAGCGAATT
TGCTTGGCCTGGAGCTTCTTCTTGGGCTCTCAATGGACGTAATAGCTTGA
TGAATCCTGGACCTGCTATGGCCAGCTACAAAGAAGGAGGACCGTTTC
TTTCCTTTGTCTGGATCTTTAATTTTTGGCAAACAAGGAAGACAA
CAACGTGGATGCGGACAAAGTCATGATAACCAACGAAGAAGAAATTAAA
ACTACTAACCCGGTAGCAACGGAGTCCTATGGACAAGTGGCCACAAACCA
CCAGAGTGCCCAAGCACAGGCGCAGACCGGCTGGGTTCAAAACCAAGGAA
TACTTCCGGGTATGGTTTGGCAGGACAGAGATGTGTACCTGCAAGGACCC
ATTTGGGCCAAAATTCCTCACACGGACGGCAACTTTCACCCTTCTCCGCT
GATGGGAGGGTTTGGAATGAAGCACCCGCCTCCTCAGATCCTCATCAAAA
CACACCTGTACCTGCGGATCCTCCAACGGCTTCAACAAGGACAAGCTG
AACTCTTTCATCACCCAGTATTCTACTGGCCAAGTCAGCGTGGAGATCGA
GTGGGAGCTGCAGAAGGAAAACAGCAAGCGCTGGAACCCGGAGATCCAGT
ACACTTCCAACTATTACAAGTCTAATAATGTTGAATTTGCTGTTAATACT
GAAGGTGTATATAGTGAACCCCGCCCCATTGGCACCAGATACCTGACTCG
TAATCTG

>SEQ ID NO: 11-NUCLEIC ACID ENCODING AAV9I CAPSID
ATGGCTGCCGATGGTTATCTTCCAGATTGGCTCGAGGACAACCTTAGTGA

| SEQUENCES |
|---|
| AGGAATTCGCGAGTGGTGGGCTTTGAAACCTGGAGCCCCTCAACCCAAGG |
| CAAATCAACAACATCAAGCAACGCTCGAGGTCTTGTGCTTCCGGGTTAC |
| AAATACCTTGGACCCGGCAACGGACTCGACAAGGGGGAGCCGGTCAACGC |
| AGCAGACGCGGCGGCCCTCGAGCACGACAAGGCCTACGACCAGCAGCTCA |
| AGGCCGGAGACAACCCGTACCTCAAGTACAACCACGCCGACGCCGAGTTC |
| CAGGAGCGGCTCAAAGAAGATACGTCTTTTGGGGGCAACCTCGGGCGAGC |
| AGTCTTCCAGGCCAAAAAGAGGCTTCTTGAACCTCTTGGTCTGGTTGAGG |
| AAGCGGCTAAGACGGCTCCTGGAAAGAAGAGGCCTGTAGAGCAGTCTCCT |
| CAGGAACCGGACTCCTCCGCGGGTATTGCAAATCGGGTGCACAGCCCGC |
| TAAAAAGAGACTCAATTTCGGTCAGACTGGCGACACAGAGTCAGTCCCAG |
| ACCCTCAACCAATCGGAGAACCTCCCGCAGCCCCCTCAGGTGTGGGATCT |
| CTTACAATGGCTTCAGGTGGTGGCGCACCAGTGGCAGACAATAACGAAGG |
| TGCCGATGGAGTGGGTAGTTCCTCGGGAAATTGGCATTGCGATTCCCAAT |
| GGCTGGGGGACAGAGTCATCACCACCAGCACCCGAACCTGGGCCCTGCCC |
| ACCTACAACAATCACCTCTACAAGCAAATCTCCAACAGCACATCTGGAGG |
| ATCTTCAAATGACAACGCCTACTTCGGCTACAGCACCCCCTGGGGGTATT |
| TTGACTTCAACAGATTCCACTGCCACTTCTCACCACGTGACTGGCAGCGA |
| CTCATCAACAACAACTGGGGATTCCGGCCTAAGCGACTCAACTTCAAGCT |
| CTTCAACATTCAGGTCAAAGAGGTTACGGACAACAATGGAGTCAAGACCA |
| TCGCCAATAACCTTACCAGCACGGTCCAGGTCTTCACGGACTCAGACTAT |
| CAGCTCCCGTACGTGCTCGGGTCGGCTCACGAGGGCTGCCTCCCGCCGTT |
| CCCAGCGGACGTTTTCATGATTCCTCAGTACGGGTATCTGACGCTTAATG |
| ATGGAAGCCAGGCCGTGGGTCGTTCGTCCTTTTACTGCCTGGAATATTTC |
| CCGTCGCAAATGCTAAGAACGGGTAACAACTTCCAGTTCAGCTACGAGTT |
| TGAGAACGTACCTTTCCATAGCAGCTACGCTCACAGCCAAAGCCTGGACC |
| GACTAATGAATCCACTCATCGACCAATACTTGTACTATCTCTCAAAGACT |
| ATTAACGGTTCTGGACAGAATCAACAAACGCTAAAATTCAGTGTGGCCGG |
| ACCCAGCAACATGGCTGTCCAGGGAAGAAACTACATACCTGGACCCAGCT |
| ACCGACAACAACGTGTCTCAACCACTGTGACTCAAAACAACAACAGCGAA |
| TTTGCTTGGCCTGGAGCTTCTTCTTGGGCTCTCAATGGACGTAATAGCTT |
| GATGAATCCTGGACCTGCTATGGCCAGCCACAAAGAAGGAGAGGACCGTT |
| TCTTTCCTTTGTCTGGATCTTTAATTTTTGGCAAACAAGGAACTGGAAGA |
| GACAACGTGGATGCGGACAAAGTCATGATAACCAACGAAGAAGAAATTAA |
| AACTACTAACCCGGTAGCAACGGAGTCCTATGGACAAGTGGCCACAAACC |
| ACCAGAGTGCCCAAGCACAGGCGCAGACCGGCTGGGTTCAAAACCAAGGA |
| ATACTTCCGGGTATGGTTTGGCAGGACAGAGATGTGTACCTGCAAGGACC |
| CATTTGGGCCAAAATTCCTCACACGGACGGCAACTTTCACCCTTCTCCGC |
| TGATGGGAGGGTTTGGAATGAAGCACCCGCCTCCTCAGACCCTCATCAAA |
| AACACACCTGTACCTGCGGATCCTCCAACGGCCTTCAACAAGGACAAGCT |
| GAACTCTTTCATCACCCAGTATTCTACTGGCCAAGTCAGCGTGGAGATCG |
| AGTGGGAGCTGCAGAAGGAAAACAGCAAGCGCTGGAACCCGGAGATCCAG |
| TACACTTCCAACTATTACAAGTCTAATAATGTTGAATTTGCTGTTAATAC |
| TGAAGGTGTATATAGTGAACCCCGCCCCATTGGCACCAGATACCTGACTC |
| GTAATCTG |
| |
| >SEQ ID NO: 12-NUCLEIC ACID ENCODING AAV9R CAPSID |
| ATGGCTGCCGATGGTTATCTTCCAGATTGGCTCGAGGACAACCTTAGTGA |
| AGGAATTCGCGAGTGGTGGGCTTTGAAACCTGGAGCCCCTCAACCCAAGG |
| CAAATCAACAACATCAAGCAACGCTCGAGGTCTTGTGCTTCCGGGTTAC |
| AAATACCTTGGACCCGGCAACGGACTCGACAAGGGGGAGCCGGTCAACGC |
| AGCAGACGCGGCGGCCCTCGAGCACGACAAGGCCTACGACCAGCAGCTCA |
| AGGCCGGAGACAACCCGTACCTCAAGTACAACCACGCCGACGCCGAGTTC |
| CAGGAGCGGCTCAAAGAAGATACGTCTTTTGGGGGCAACCTCGGGCGAGC |
| AGTCTTCCAGGCCAAAAAGAGGCTTCTTGAACCTCTTGGTCTGGTTGAGG |
| AAGCGGCTAAGACGGCTCCTGGAAAGAAGAGGCCTGTAGAGCAGTCTCCT |
| CAGGAACCGGACTCCTCCGCGGGTATTGCAAATCGGGTGCACAGCCCGC |
| TAAAAAGAGACTCAATTTCGGTCAGACTGGCGACACAGAGTCAGTCCCAG |
| ACCCTCAACCAATCGGAGAACCTCCCGCAGCCCCCTCAGGTGTGGGATCT |
| CTTACAATGGCTTCAGGTGGTGGCGCACCAGTGGCAGACAATAACGAAGG |
| TGCCGATGGAGTGGGTAGTTCCTCGGGAAATTGGCATTGCGATTCCCAAT |
| GGCTGGGGGACAGAGTCATCACCACCAGCACCCGAACCTGGGCCCTGCCC |
| ACCTACAACAATCACCTCTACAAGCAAATCTCCAACAGCACATCTGGAGG |
| ATCTTCAAATGACAACGCCTACTTCGGCTACAGCACCCCCTGGGGGTATT |
| TTGACTTCAACAGATTCCACTGCCACTTCTCACCACGTGACTGGCAGCGA |
| CTCATCAACAACAACTGGGGATTCCGGCCTAAGCGACTCAACTTCAAGCT |
| CTTCAACATTCAGGTCAAAGAGGTTACGGACAACAATGGAGTCAAGACCA |
| TCGCCAATAACCTTACCAGCACGGTCCAGGTCTTCACGGACTCAGACTAT |
| CAGCTCCCGTACGTGCTCGGGTCGGCTCACGAGGGCTGCCTCCCGCCGTT |
| CCCAGCGGACGTTTTCATGATTCCTCAGTACGGGTATCTGACGCTTAATG |
| ATGGAAGCCAGGCCGTGGGTCGTTCGTCCTTTTACTGCCTGGAATATTTC |
| CCGTCGCAAATGCTAAGAACGGGTAACAACTTCCAGTTCAGCTACGAGTT |
| TGAGAACGTACCTTTCCATAGCAGCTACGCTCACAGCCAAAGCCTGGACC |
| GACTAATGAATCCACTCATCGACCAATACTTGTACTATCTCTCAAAGACT |
| ATTAACGGTTCTGGACAGAATCAACAAACGCTAAAATTCAGTGTGGCCGG |
| ACCCAGCAACATGGCTGTCCAGGGAAGAAACTACATACCTGGACCCAGCT |
| ACCGACAACAACGTGTCTCAACCACTGTGACTCAAAACAACAACAGCGAA |
| TTTGCTTGGCCTGGAGCTTCTTCTTGGGCTCTCAATGGACGTAATAGCTT |
| GATGAATCCTGGACCTGCTATGGCCAGCCACAAAGAAGGAGAGGACAGTT |
| TCTTTCCTTTGTCTGGATCTTTAATTTTTGGCAAACAAGGAACTGGAAGA |
| GACAACGTGGATGCGGACAAAGTCATGATAACCAACGAAGAAGAAATTAA |
| AACTACTAACCCGGTAGCAACGGAGTCCTATGGACAAGTGGCCACAAACC |
| ACCAGAGTGCCCAAGCACAGGCGCAGACCGGCTGGGTTCAAAACCAAGGA |
| ATACTTCCGGGTATGGTTTGGCAGGACAGAGATGTGTACCTGCAAGGACC |
| CATTTGGGCCAAAATTCCTCACACGGACGGCAACTTTCACCCTTCTCCGC |
| TGATGGGAGGGTTTGGAATGAAGCACCCGCCTCCTCAGACCCTCATCAAA |
| AACACACCTGTACCTGCGGATCCTCCAACGGCCTTCAACAAGGACAAGCT |
| GAACTCTTTCATCACCCAGTATTCTACTGGCCAAGTCAGCGTGGAGATCG |
| AGTGGGAGCTGCAGAAGGAAAACAGCAAGCGCTGGAACCCGGAGATCCAG |
| TACACTTCCAACTATTACAAGTCTAATAATGTTGAATTTGCTGTTAATAC |
| TGAAGGTGTATATAGTGAACCCCGCCCCATTGGCACCAGATACCTGACTC |
| GTAATCTG |
| |
| >SEQ ID NO: 13-NUCLEIC ACID ENCODING AAV9Y CAPSID |
| ATGGCTGCCGATGGTTATCTTCCAGATTGGCTCGAGGACAACCTTAGTGA |
| AGGAATTCGCGAGTGGTGGGCTTTGAAACCTGGAGCCCCTCAACCCAAGG |
| CAAATCAACAACATCAAGCAACGCTCGAGGTCTTGTGCTTCCGGGTTAC |
| AAATACCTTGGACCCGGCAACGGACTCGACAAGGGGGAGCCGGTCAACGC |
| AGCAGACGCGGCGGCCCTCGAGCACGACAAGGCCTACGACCAGCAGCTCA |
| AGGCCGGAGACAACCCGTACCTCAAGTACAACCACGCCGACGCCGAGTTC |
| CAGGAGCGGCTCAAAGAAGATACGTCTTTTGGGGGCAACCTCGGGCGAGC |
| AGTCTTCCAGGCCAAAAAGAGGCTTCTTGAACCTCTTGGTCTGGTTGAGG |
| AAGCGGCTAAGACGGCTCCTGGAAAGAAGAGGCCTGTAGAGCAGTCTCCT |
| CAGGAACCGGACTCCTCCGCGGGTATTGCAAATCGGGTGCACAGCCCGC |
| TAAAAAGAGACTCAATTTCGGTCAGACTGGCGACACAGAGTCAGTCCCAG |
| ACCCTCAACCAATCGGAGAACCTCCCGCAGCCCCCTCAGGTGTGGGATCT |
| CTTACAATGGCTTCAGGTGGTGGCGCACCAGTGGCAGACAATAACGAAGG |
| TGCCGATGGAGTGGGTAGTTCCTCGGGAAATTGGCATTGCGATTCCCAAT |
| GGCTGGGGGACAGAGTCATCACCACCAGCACCCGAACCTGGGCCCTGCCC |
| ACCTACAACAATCACCTCTACAAGCAAATCTCCAACAGCACATCTGGAGG |
| ATCTTCAAATGACAACGCCTACTTCGGCTACAGCACCCCCTGGGGGTATT |
| TTGACTTCAACAGATTCCACTGCCACTTCTCACCACGTGACTGGCAGCGA |
| CTCATCAACAACAACTGGGGATTCCGGCCTAAGCGACTCAACTTCAAGCT |
| CTTCAACATTCAGGTCAAAGAGGTTACGGACAACAATGGAGTCAAGACCA |
| TCGCCAATAACCTTACCAGCACGGTCCAGGTCTTCACGGACTCAGACTAT |
| CAGCTCCCGTACGTGCTCGGGTCGGCTCACGAGGGCTGCCTCCCGCCGTT |
| CCCAGCGGACGTTTTCATGATTCCTCAGTACGGGTATCTGACGCTTAATG |
| ATGGAAGCCAGGCCGTGGGTCGTTCGTCCTTTTACTGCCTGGAATATTTC |
| CCGTCGCAAATGCTAAGAACGGGTAACAACTTCCAGTTCAGCTACGAGTT |
| TGAGAACGTACCTTTCCATAGCAGCTACGCTCACAGCCAAAGCCTGGACC |
| GACTAATGAATCCACTCATCGACCAATACTTGCACTATCTCTCAAAGACT |
| ATTAACGGTTCTGGACAGAATCAACAAACGCTAAAATTCAGTGTGGCCGG |
| ACCCAGCAACATGGCTGTCCAGGGAAGAAACTACATACCTGGACCCAGCT |
| ACCGACAACAACGTGTCTCAACCACTGTGACTCAAAACAACAACAGCGAA |
| TTTGCTTGGCCTGGAGCTTCTTCTTGGGCTCTCAATGGACGTAATAGCTT |
| GATGAATCCTGGACCTGCTATGGCCAGCCACAAAGAAGGAGAGGACCGTT |
| TCTTTCCTTTGTCTGGATCTTTAATTTTTGGCAAACAAGGAACTGGAAGA |
| GACAACGTGGATGCGGACAAAGTCATGATAACCAACGAAGAAGAAATTAA |
| AACTACTAACCCGGTAGCAACGGAGTCCTATGGACAAGTGGCCACAAACC |
| ACCAGAGTGCCCAAGCACAGGCGCAGACCGGCTGGGTTCAAAACCAAGGA |
| ATACTTCCGGGTATGGTTTGGCAGGACAGAGATGTGTACCTGCAAGGACC |
| CATTTGGGCCAAAATTCCTCACACGGACGGCAACTTTCACCCTTCTCCGC |
| TGATGGGAGGGTTTGGAATGAAGCACCCGCCTCCTCAGACCCTCATCAAA |
| AACACACCTGTACCTGCGGATCCTCCAACGGCCTTCAACAAGGACAAGCT |
| GAACTCTTTCATCACCCAGTATTCTACTGGCCAAGTCAGCGTGGAGATCG |
| AGTGGGAGCTGCAGAAGGAAAACAGCAAGCGCTGGAACCCGGAGATCCAG |
| TACACTTCCAACTATTACAAGTCTAATAATGTTGAATTTGCTGTTAATAC |
| TGAAGGTGTATATAGTGAACCCCGCCCCATTGGCACCAGATACCTGACTC |
| GTAATCTG |
| |
| >SEQ ID NO: 14-NUCLEIC ACID ENCODING AAV9.HR CAPSID |
| ATGGCTGCCGATGGTTATCTTCCAGATTGGCTCGAGGACAACCTTAGTGA |
| AGGAATTCGCGAGTGGTGGGCTTTGAAACCTGGAGCCCCTCAACCCAAGG |
| CAAATCAACAACATCAAGCAACGCTCGAGGTCTTGTGCTTCCGGGTTAC |
| AAATACCTTGGACCCGGCAACGGACTCGACAAGGGGGAGCCGGTCAACGC |
| AGCAGACGCGGCGGCCCTCGAGCACGACAAGGCCTACGACCAGCAGCTCA |
| AGGCCGGAGACAACCCGTACCTCAAGTACAACCACGCCGACGCCGAGTTC |
| CAGGAGCGGCTCAAAGAAGATACGTCTTTTGGGGGCAACCTCGGGCGAGC |
| AGTCTTCCAGGCCAAAAAGAGGCTTCTTGAACCTCTTGGTCTGGTTGAGG |
| AAGCGGCTAAGACGGCTCCTGGAAAGAAGAGGCCTGTAGAGCAGTCTCCT |
| CAGGAACCGGACTCCTCCGCGGGTATTGCAAATCGGGTGCACAGCCCGC |
| TAAAAAGAGACTCAATTTCGGTCAGACTGGCGACACAGAGTCAGTCCCAG |
| ACCCTCAACCAATCGGAGAACCTCCCGCAGCCCCCTCAGGTGTGGGATCT |
| CTTACAATGGCTTCAGGTGGTGGCGCACCAGTGGCAGACAATAACGAAGG |

SEQUENCES

```
TGCCGATGGAGTGGGTAGTTCCTCGGGAAATTGGCATTGCGATTCCCAAT
GGCTGGGGGACAGAGTCATCACCACCAGCACCCGAACCTGGGCCCTGCCC
ACCTACAACAATCACCTCTACAAGCAAATCTCCAACAGCACATCTGGAGG
ATCTTCAAATGACAACGCCTACTTCGGCTACAGCACCCCCTGGGGGTATT
TTGACTTCAACAGATTCCACTGCCACTTCTCACCACGTGACTGGCAGCGA
CTCATCAACAACAACTGGGGATTCCGGCCTAAGCGACTCAACTTCAAGCT
CTTCAACATTCAGGTCAAAGAGGTTACGGACAACAATGGAGTCAAGACCA
TCGCCAATAACCTTACCAGCACGGTCCAGGTCTTCACGGACTCAGACTAT
CAGCTCCCGTACGTGCTCGGGTCGGCTCACGAGGGCTGCCTCCCGCCGTT
CCCAGCGGACGTTTTCATGATTCCTCAGTACGGGTATCTGACGCTTAATG
ATGGAAGCCAGGCCGTGGGTCGTTCGTCCTTTTACTGCCTGGAATATTTC
CCGTCGCAAATGCTAAGAACGGGTAACAACTTCCAGTTCAGCTACGAGTT
TGAGAACGTACCTTTCCATAGCAGCTACGCTCACAGCCAAAGCCTGGACC
GACTAATGAATCCACTCATCGACCAATACTTGTACTATCTCTCAAAGACT
ATTAACGGTTCTGGACAGAATCAACAAACGCTAAAATTCAGTGTGGCCGG
ACCCAGCAACATGGCTGTCCAGGGAGAGAAACTACATACCTGGACCCAGCT
ACCGACAACAACGTGTCTCAACCACTGTGACTCAAAACAACAACAGCGAA
TTTGCTTGGCCTGGAGCTTCTTCTTGGGCTCTCAATGGACGTAATAGCTT
GATGAATCCTGGACCTGCTATGGCCAGCTACAAAGAAGGAGAGGACAGTT
TCTTTCCTTTGTCTGGATCTTTAATTTTTGGCAAACAAGGAACTGGAAGA
GACAACGTGGATGCGGACAAAGTCATGATAACCAACGAAGAAGAAATTAA
AACTACTAACCCGGTAGCAACGGAGTCCTATGGACAAGTGGCCACAAACC
ACCAGAGTGCCCAAGCACAGGCGCAGACCGGCTGGGTTCAAAACCAAGGA
ATACTTCCGGGTATGGTTTGGCAGGACAGAGATGTGTACCTGCAAGGACC
CATTTGGGCCAAAATTCCTCACACGGACGGCAACTTTCACCCTTCTCCGC
TGATGGGAGGGTTTGGAATGAAGCACCCGCCTCCTCAGATCCTCATCAAA
AACACACCTGTACCTGCGGATCCTCCAACGGCCTTCAACAAGGACAAGCT
GAACTCTTTCATCACCCAGTATTCTACTGGCCAAGTCAGCGTGGAGATCG
AGTGGGAGCTGCAGAAGGAAAACAGCAAGCGCTGGAACCCGGAGATCCAG
TACACTTCCAACTATTACAAGTCTAATAATGTTGAATTTGCTGTTAATAC
TGAAGGTGTATATAGTGAACCCCGCCCCATTGGCACCAGATACCTGACTC
GTAATCTG

>SEQ ID NO: 15-Protein Alignment Consensus
Sequence from FIG. 1
MAADGYLPDWLEDNLSEGIREWWALKPGAPQPKANQQHQDNARGLVLPGY
KYLGPGNGLDKGEPVNAADAALEHDKAYDQQLKAGDNPYLKYNHADAEFQ
```

```
ERLKEDTSFGGNLGRAVFQAKKRLLEPLGLVEEAAKTAPGKKRPVEQSPQ
EPDSSAGIGKSGAQPAKKRLNFGQTGDTESVPDPQPIGEPPAAPSGVGSL
TMASGGGAPVADNNEGADGVGSSSGNWHCDSQWLGDRVITTSTRTWALPT
YNNHLYKQISNSTSGGSSNDNAYFGYSTPWGYFDFNRFHCHFSPRDWQRL
INNNWGFRPKRLNFKLFNIQVKEVTDNNGVKTIANNLTSTVQVFTDSDYQ
LPYVLGSAHEGCLPPFPADVFMIPQYGYLTLNDGSQAVGRSSFYCLEYFP
SQMLRTGNNFQFSYEFENVPFHSSYAHSQSLDRLMNPLIDQYLYYLSKTI
NGSGQNQQTLKFSVAGPSNMAVQGRNYIPGPSYRQQRVSTTVTQNNNSEF
AWPGASSWALNGRNSLMNPGPAMASHKEGEDRFFPLSGSLIFGKQGTGRD
NVDADKVMITNEEEIKTTNPVATESYGQVATNHQSAQAQAQTGWVQNQGI
LPGMVWQDRDVYLQGPIWAKIPHTDGNFHPSPLMGGFGMKHPPPQILIKN
TPVPADPPTAFNKDKLNSFITQYSTGQVSVEIEWELQKENSKRWNPEIQY
TSNYYKSNNVEFAVNTEGVYSEPRPIGTRYLTRNL
```

This disclosure is not limited in its application to the details of construction and the arrangement of components set forth in this description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

What is claimed is:

1. A recombinant AAV (rAAV) comprising an AAV capsid protein having an amino acid sequence selected from the group consisting of: SEQ ID NOs: 3-7.

2. A composition comprising the recombinant rAAV of claim 1.

3. The composition of claim 2 further comprising a pharmaceutically acceptable carrier.

4. A method for delivering a transgene to a subject comprising administering the rAAV of claim 1 to a subject, wherein the rAAV comprises
   at least one transgene, and wherein the rAAV infects cells of a target tissue of the subject.

5. The method of claim 4, wherein the at least one transgene encodes a CNS-protein or a secreted tumor suppressor protein.

6. The method of claim 5, wherein the CNS-protein is aspartoacylase (ASPA), or wherein the secreted tumor suppressor protein is IGFBP7 or SRPX.

7. The method of claim 6, wherein the ASPA is human ASPA.

8. The method of claim 4, wherein the at least one transgene encodes an immunoglobulin heavy chain or light chain or fragment thereof.

9. The method of claim 4, wherein the at least one transgene encodes a miRNA, miRNA sponge, or TuD RNA.

10. The method of claim 9, wherein the miRNA is expressed in a cell of the target tissue.

11. The method of claim 4, wherein the rAAV is administered to the subject intravenously, transdermally, intraocularly, intrathecally, orally, intramuscularly, subcutaneously, intranasally, or by inhalation.

12. An isolated nucleic acid comprising a sequence selected from the group consisting of: SEQ ID NOs: 10-14, or encoding an AAV capsid protein having an amino acid sequence selected from the group consisting of SEQ ID NOs: 3-7.

13. An isolated AAV capsid protein comprising an amino acid sequence selected from the group consisting of: SEQ ID NOs: 3-7.

14. A composition comprising the isolated AAV capsid protein of claim 13.

15. The composition of claim 14 further comprising a pharmaceutically acceptable carrier.

16. A method for treating Canavan disease, the method comprising administering to a subject a therapeutically effective amount of a rAAV to a subject, wherein the rAAV comprises:
   (i) the isolated capsid protein of claim 13, and
   (ii) at least one transgene, wherein the at least one transgene encodes ASPA;
   and wherein the rAAV infects cells of a target tissue of the subject.

17. The method of claim 16, wherein the target tissue is CNS tissue.

18. A method for treating cancer, the method comprising administering to a subject a therapeutically effective amount of a rAAV to a subject, wherein the rAAV comprises:
   (i) the isolated capsid protein of claim 13, and
   (ii) at least one transgene, wherein the at least one transgene encodes a tumor suppressor protein;
   and wherein the rAAV infects cells of a target tissue of the subject.

19. The method of claim 18, wherein the tumor suppressor protein is selected from the group consisting of IGFBP7 and SRPX.

* * * * *

SEQUENCE LISTING

```
<160> NUMBER OF SEQ ID NOS: 15

<210> SEQ ID NO 1
<211> LENGTH: 736
<212> TYPE: PRT
<213> ORGANISM: Adeno associated virus 9

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
```

-continued

```
                130               135               140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
            450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
```

```
Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
        645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 2
<211> LENGTH: 736
<212> TYPE: PRT
<213> ORGANISM: Adeno associated virus 9
<220> FEATURE:
<223> OTHER INFORMATION: Clvd8

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190
```

```
Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu His Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser Tyr Lys
            515                 520                 525

Glu Gly Glu Asp Ser Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605
```

```
Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Phe Gly Met
625                 630                 635                 640

Lys His Pro Pro Gln Thr Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 3
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240
```

```
Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser Tyr Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
```

```
                    660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
            690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 4
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 4

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
```

```
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                    325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
                530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Met
625                 630                 635                 640
Lys His Pro Pro Pro Gln Thr Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
                690                 695                 700
Tyr Tyr Lys Ser Asn Asn Val Glu Phe Ala Val Asn Thr Glu Gly Val
705                 710                 715                 720
```

Tyr Ser Glu Pro Arg Pro Ile Gly Thr Arg Tyr Leu Thr Arg Asn Leu
            725                 730                 735

<210> SEQ ID NO 5
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Ser Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 6
<211> LENGTH: 736
<212> TYPE: PRT
<213> ORGANISM: Artificial Sequence
<220> FEATURE:

<223> OTHER INFORMATION: Synthetic polypeptide

<400> SEQUENCE: 6

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400
```

```
Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu His Tyr Leu Ser
        435                 440                 445

Lys Thr Ile Asn Gly Ser Gln Asn Gln Gln Thr Leu Lys Phe Ser
    450                 455                 460

Val Ala Gly Pro Ser Asn Met Ala Val Gln Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30
```

-continued

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
    195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
    435                 440                 445

Lys Thr Ile Asn Gly Ser Gly Gln Asn Gln Gln Thr Leu Lys Phe Ser 450                 455                 460
Val Ala Gly Pro Ser Asn Met Ala Val Gln Gly Arg Asn Tyr Ile Pro
465                 470                 475                 480

Gly Pro Ser Tyr Arg Gln Arg Val Ser Thr Thr Val Thr Gln Asn
            485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser Tyr Lys
            515                 520                 525

Glu Gly Glu Asp Ser Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 8
<211> LENGTH: 2208
<212> TYPE: DNA
<213> ORGANISM: Adeno associated virus 9

<400> SEQUENCE: 8
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag tcttgtgct tccgggttac aaataccttg acccggcaa cggactcgac    180 aaggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540

```
tcagtcccag accctcaacc aatcggagaa cctcccgcag cccccctcagg tgtgggatct    600 cttacaatgg cttcaggtgg tggcgcacca gtggcagaca ataacgaagg tgccgatgga    660
gtgggtagtt cctcgggaaa ttggcattgc gattcccaat ggctggggga cagagtcatc    720
accaccagca cccgaacctg ggccctgccc acctacaaca tcacctcta caagcaaatc      780 tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactgggg attccggcct aagcgactca acttcaagct cttcaacatt       960
caggtcaaag aggttacgga caacaatgga gtcaagacca tcgccaataa ccttaccagc   1020
acggtccagg tcttcacgga ctcagactat cagctcccgt acgtgctcgg gtcggctcac    1080
gagggctgcc tcccgccgtt cccagcggac gttttcatga ttcctcagta cgggtatctg    1140
acgcttaatg atggaagcca ggccgtgggt cgttcgtcct tttactgcct ggaatatttc     1200
ccgtcgcaaa tgctaagaac gggtaacaac ttccagttca gctacgagtt tgagaacgta   1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa   1500
tttgcttggc ctggagcttc ttctgggct ctcaatggac gtaatagctt gatgaatcct     1560
ggacctgcta tggccagcca caagaagga gaggaccgtt tctttccttt gtctggatct      1620 ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcagaccg gctgggttca aaaccaagga   1800
atacttccgg gtatggtttg gcaggacaga gatgtgtacc tgcaaggacc catttgggcc    1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc    2040
gtggagatcg agtgggagct gcagaaggaa aacagcaagc gctggaaccc ggagatccag   2100
tacacttcca actattacaa gtctaataat gttgaatttg ctgttaatac tgaaggtgta      2160
tatagtgaac ccgccccat tggcaccaga tacctgactc gtaatctg                2208

<210> SEQ ID NO 9
<211> LENGTH: 2208
<212> TYPE: DNA
<213> ORGANISM: Adeno associated virus 9
<220> FEATURE:
<223> OTHER INFORMATION: Clvd8

<400> SEQUENCE: 9
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag tcttgtgct tccgggttac aaataccttg acccggcaa cggactcgac     180 aaggggagc cggtcaacgc agcagacgcg gcggccctcg agcacgacaa ggcctacgac   240
cagcagctca aggccggaga caaccccgtac ctcaagtaca accacgccga cgccgagttc    300
caggagcggc tcaaagaaga tacgtctttt ggggcaacc tcgggcgagc agtcttccag    360
gccaaaaaga ggcttcttga acctcttggt ctggttgagg aagcggctaa gacggctcct   420
```

```
ggaaagaaga ggcctgtaga gcagtctcct caggaaccgg actcctccgc gggtattggc      480
aaatcgggtg cacagcccgc taaaagagac ctcaatttcg gtcagactgg cgacacagag      540
tcagtcccag accctcaacc aatcggagaa cctcccgcag cccctcagg tgtgggatct       600 cttacaatgg cttcaggtgg tggcgcacca gtggcagaca ataacgaagg tgccgatgga      660
gtgggtagtt cctcgggaaa ttggcattgc gattcccaat ggctggggga cagagtcatc      720
accaccagca cccgaacctg ggccctgccc acctacaaca atcacctcta caagcaaatc      780
tccaacagca catctggagg atcttcaaat gacaacgcct acttcggcta cagcaccccc      840
tgggggtatt ttgacttcaa cagattccac tgccacttct caccacgtga ctggcagcga      900
ctcatcaaca caactgggga attccggcct aagcgactca acttcaagct cttcaacatt      960
caggtcaaag aggttacgga caacaatgga gtcaagacca tcgccaataa ccttaccagc     1020
acggtccagg tcttcacgga ctcagactat cagctcccgt acgtgctcgg tcggctcac      1080 gagggctgcc tcccgccgtt cccagcgac gttttcatga ttcctcagta cgggtatctg      1140
acgcttaatg atggaagcca ggccgtgggt cgttcgtcct tttactgcct ggaatatttc     1200
ccgtcgcaaa tgctaagaac gggtaacaac ttccagttca gctacgagtt tgagaacgta     1260 ccttttccata gcagctacgc tcacagccaa agcctggacc gactaatgaa tccactcatc     1320
gaccaatact tgcactatct ctcaaagact attaacggtt ctggacagaa tcaacaaacg     1380
ctaaaattca gtgtggccgg acccagcaac atggctgtcc agggaagaaa ctacatacct     1440
ggacccagct accgacaaca acgtgtctca accactgtga ctcaaaacaa caacagcgaa     1500
tttgcttggc ctggagcttc ttcttgggct ctcaatggac gtaatagctt gatgaatcct     1560
ggacctgcta tggccagcta caagaaggga gaggacagtt tctttcctt gtctggatct      1620 ttaattttg gcaaacaagg aactggaaga gacaacgtgg atgcggacaa agtcatgata     1680
accaacgaag aagaaattaa aactactaac ccggtagcaa cggagtccta tggacaagtg     1740
gccacaaacc accagagtgc ccaagcacag cgcagaccg gctgggttca aaaccaagga      1800
atacttccgg gtatggtttg gcaggacaga gatgtgtacc tgcaaggacc catttgggcc     1860
aaaattcctc acacggacgg caactttcac ccttctccgc tgatgggagg gtttggaatg     1920
aagcacccgc ctcctcagac cctcatcaaa aacacacctg tacctgcgga tcctccaacg     1980
gccttcaaca aggacaagct gaactctttc atcacccagt attctactgg ccaagtcagc     2040
gtggagatcg agtgggagct gcagaaggaa aacagcaagc gctggaaccc ggagatccag     2100
tacacttcca actattacaa gtctaataat gttgaatttg ctgttaatac tgaaggtgta     2160
tatagtgaac ccgcccccat tggcaccaga tacctgactc gtaatctg                  2208
```

<210> SEQ ID NO 10
<211> LENGTH: 2208
<212> TYPE: DNA
<213> ORGANISM: Artificial Sequence
<220> FEATURE:
<223> OTHER INFORMATION: Synthetic nucleic acid

<400> SEQUENCE: 10

```
atggctgccg atggttatct tccagattgg ctcgaggaca accttagtga aggaattcgc       60
gagtggtggg ctttgaaacc tggagcccct caacccaagg caaatcaaca acatcaagac      120
aacgctcgag tcttgtgct tccgggttac aaataccttg acccggcaa cggactcgac        180 aagggggagc cggtcaacgc agcagacgcg gcggcccctcg agcacgacaa ggcctacgac     240
```

```
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccccctcagg tgtgggatct   600 cttacaatgg cttcaggtgg tggcgcacca gtggcagaca taacgaagg tgccgatgga    660 gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactggggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg gtcggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcta caagaagga gaggaccgtt tctttccttt gtctggatct   1620 ttaattttg caaacaagg aactggaaga acaacgtgg atgcggacaa agtcatgata    1680
accaacgaag aagaaattaa aactactaac ccggtagcaa cggagtccta tggacaagtg   1740
gccacaaacc accagagtgc ccaagcacag gcgcagaccg gctgggttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctg              2208
```

<210> SEQ ID NO 11
<211> LENGTH: 2208
<212> TYPE: DNA
<213> ORGANISM: Artificial Sequence
<220> FEATURE:
<223> OTHER INFORMATION: Synthetic nucleic acid

<400> SEQUENCE: 11

```
atggctgccg atggttatct tccagattgg ctcgaggaca accttagtga aggaattcgc    60
gagtggtggg cttttgaaacc tggagcccct caacccaagg caaatcaaca acatcaagac   120
```

```
aacgctcgag gtcttgtgct tccgggttac aaataccttg acccggcaa cggactcgac      180 aaggggggagc cggtcaacgc agcagacgcg gcggccctcg agcacgacaa ggcctacgac    240
cagcagctca aggccggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccccctcagg tgtgggatct    600 cttacaatgg cttcaggtgg tggcgcacca gtggcagaca taacgaagg tgccgatgga    660 gtgggtagtt cctcgggaaa ttggcattgc gattcccaat ggctggggga cagagtcatc    720
accaccagca cccgaacctg ggccctgccc acctacaaca atcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg tcggctcac    1080 gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacataccct   1440 ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaaagga gaggaccgtt tctttccttt gtctggatct   1620 ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcagaccg gctgggttca aaaccaagga   1800
atacttccgg gtatggtttg gcaggacaga gatgtgtacc tgcaaggacc catttgggcc   1860
aaaattcctc acacggacgg caactttcac ccttctccgc tgatgggagg gtttggaatg   1920
aagcacccgc tcctcagac cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa aacagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctg               2208
```

<210> SEQ ID NO 12
<211> LENGTH: 2208
<212> TYPE: DNA
<213> ORGANISM: Artificial Sequence
<220> FEATURE:
<223> OTHER INFORMATION: Synthetic nucleic acid

<400> SEQUENCE: 12

```
atggctgccg atggttatct tccagattgg ctcgaggaca accttagtga aggaattcgc    60
gagtggtggg ctttgaaacc tggagcccct caacccaagg caaatcaaca acatcaagac   120
aacgctcgag gtcttgtgct tccgggttac aaataccttg acccggcaa cggactcgac   180
aaggggagc cggtcaacgc agcagacgcg gcggccctcg agcacgacaa ggcctacgac   240
cagcagctca aggccggaga caacccgtac ctcaagtaca ccacgccga cgccgagttc   300
caggagcggc tcaaagaaga tacgtctttt gggggcaacc tcgggcgagc agtcttccag   360
gccaaaaaga ggcttcttga acctcttggt ctggttgagg aagcggctaa dacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg tgtgggatct   600
cttacaatgg cttcaggtgg tggcgcacca gtggcagaca ataacgaagg tgccgatgga   660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tgggggtatt ttgacttcaa cagattccac tgccacttct caccacgtga ctggcagcga   900
ctcatcaaca caactgggg attccggcct aagcgactca acttcaagct cttcaacatt   960
caggtcaaag aggttacgga caacaatgga gtcaagacca tcgccaataa ccttaccagc  1020
acggtccagg tcttcacgga ctcagactat cagctcccgt acgtgctcgg tcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga gaggacagtt tctttccttt gtctggatct  1620
ttaattttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac cccgccccat tggcaccaga tacctgactc gtaatctg              2208
```

<210> SEQ ID NO 13
<211> LENGTH: 2208

```
<212> TYPE: DNA
<213> ORGANISM: Artificial Sequence
<220> FEATURE:
<223> OTHER INFORMATION: Synthetic nucleic acid

<400> SEQUENCE: 13
atggctgccg atggttatct tccagattgg ctcgaggaca accttagtga aggaattcgc     60
gagtggtggg ctttgaaacc tggagcccct caacccaagg caaatcaaca acatcaagac    120
aacgctcgag gtcttgtgct tccgggttac aaataccttg acccggcaa cggactcgac     180
aaggggagc cggtcaacgc agcagacgcg gcggccctcg agcacgacaa ggcctacgac     240
cagcagctca aggccggaga caacccgtac ctcaagtaca ccacgccga cgccgagttc     300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct     600
cttacaatgg cttcaggtgg tggcgcacca gtggcagaca taacgaagg tgccgatgga    660
gtgggtagtt cctcgggaaa ttggcattgc gattcccaat ggctggggga cagagtcatc    720
accaccagca cccgaacctg ggccctgccc acctacaaca tcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactgggg attccggcct aagcgactca acttcaagct cttcaacatt    960
caggtcaaag aggttacgga caacaatgga gtcaagacca cgccaataa ccttaccagc   1020
acggtccagg tcttcacgga ctcagactat cagctcccgt acgtgctcgg gtcggctcac   1080
gagggctgcc tcccgccgtt cccagcgac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgcactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caaagaagga gaggaccgtt tctttcctt gtctggatct    1620
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc caagcacag gcgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa acagcaagc gctggaaccc ggagatccag    2100
tacacttcca actattacaa gtctaataat gttgaatttg ctgttaatac tgaaggtgta    2160
```

| | |
|---|---:|
| tatagtgaac cccgccccat tggcaccaga tacctgactc gtaatctg | 2208 |

<210> SEQ ID NO 14
<211> LENGTH: 2208
<212> TYPE: DNA
<213> ORGANISM: Artificial Sequence
<220> FEATURE:
<223> OTHER INFORMATION: Synthetic nucleic acid

<400> SEQUENCE: 14

| | |
|---|---:|
| atggctgccg atggttatct tccagattgg ctcgaggaca accttagtga aggaattcgc | 60 |
| gagtggtggg cttttgaaacc tggagcccct caacccaagg caaatcaaca acatcaagac | 120 |
| aacgctcgag gtcttgtgct tccgggttac aaataccttg acccggcaa cggactcgac | 180 |
| aaggggagc cggtcaacgc agcagacgcg gcggccctcg agcacgacaa ggcctacgac | 240 |
| cagcagctca aggccggaga caacccgtac ctcaagtaca ccacgccga cgccgagttc | 300 |
| caggagcggc tcaaagaaga tacgtctttt gggggcaacc tcgggcgagc agtcttccag | 360 |
| gccaaaaaga ggcttcttga acctcttggt ctggttgagg aagcggctaa gacggctcct | 420 |
| ggaaagaaga ggcctgtaga gcagtctcct caggaaccgg actcctccgc gggtattggc | 480 |
| aaatcgggtg cacagcccgc taaaaagaga ctcaatttcg gtcagactgg cgacacagag | 540 |
| tcagtcccag accctcaacc aatcggagaa cctcccgcag cccccctcagg tgtgggatct | 600 |
| cttacaatgg cttcaggtgg tggcgcacca gtggcagaca taacgaaggt gccgatgga | 660 |
| gtgggtagtt cctcgggaaa ttggcattgc gattcccaat ggctggggga cagagtcatc | 720 |
| accaccagca cccgaacctg ggccctgccc acctacaaca tcacctctca aagcaaatc | 780 |
| tccaacagca catctggagg atcttcaaat gacaacgcct acttcggcta cagcaccccc | 840 |
| tgggggtatt ttgacttcaa cagattccac tgccacttct caccacgtga ctggcagcga | 900 |
| ctcatcaaca caactggggg attccggcct aagcgactca acttcaagct cttcaacatt | 960 |
| caggtcaaag aggttacgga caacaatgga gtcaagacca cgccaataa ccttaccagc | 1020 |
| acggtccagg tcttcacgga ctcagactat cagctcccgt acgtgctcgg tcggctcac | 1080 |
| gagggctgcc tcccgccgtt cccagcggac gttttcatga ttcctcagta cgggtatctg | 1140 |
| acgcttaatg atggaagcca ggccgtgggt cgttcgtcct tttactgcct ggaatatttc | 1200 |
| ccgtcgcaaa tgctaagaac gggtaacaac ttccagttca gctacgagtt tgagaacgta | 1260 |
| cctttccata gcagctacgc tcacagccaa agcctggacc gactaatgaa tccactcatc | 1320 |
| gaccaatact tgtactatct ctcaaagact attaacggtt ctggacagaa tcaacaaacg | 1380 |
| ctaaaattca gtgtggccgg acccagcaac atggctgtcc agggaagaaa ctacatacct | 1440 |
| ggacccagct accgacaaca acgtgtctca accactgtga ctcaaaacaa caacagcgaa | 1500 |
| tttgcttggc ctggagcttc ttcttgggct ctcaatggac gtaatagctt gatgaatcct | 1560 |
| ggacctgcta tggccagcta caagaaggga gaggacagtt tctttccttt gtctggatct | 1620 |
| ttaattttttg gcaaacaagg aactggaaga gacaacgtgg atgcggacaa agtcatgata | 1680 |
| accaacgaag aagaaattaa aactactaac ccggtagcaa cggagtccta tggacaagtg | 1740 |
| gccacaaacc accagagtgc caagcacag gcgcagaccg gctgggttca aaaccaagga | 1800 |
| atacttccgg gtatggtttg gcaggacaga gatgtgtacc tgcaaggacc catttgggcc | 1860 |
| aaaattcctc acacggacgg caactttcac ccttctccgc tgatgggagg gtttggaatg | 1920 |
| aagcacccgc ctcctcagat cctcatcaaa aacacacctg tacctgcgga tcctccaacg | 1980 |
| gccttcaaca aggacaagct gaactctttc atcacccagt attctactgg ccaagtcagc | 2040 |

```
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctg                2208
```

```
<210> SEQ ID NO 15
<211> LENGTH: 735
<212> TYPE: PRT
<213> ORGANISM: Artificial Sequence
<220> FEATURE:
<223> OTHER INFORMATION: Synthetic polypeptide

<400> SEQUENCE: 15
```

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Glu Arg Leu Lys Glu Asp Thr Ser Phe Gly Gly Asn
            100                 105                 110

Leu Gly Arg Ala Val Phe Gln Ala Lys Lys Arg Leu Leu Glu Pro Leu
        115                 120                 125

Gly Leu Val Glu Glu Ala Ala Lys Thr Ala Pro Gly Lys Lys Arg Pro
    130                 135                 140

Val Glu Gln Ser Pro Gln Glu Pro Asp Ser Ser Ala Gly Ile Gly Lys
145                 150                 155                 160

Ser Gly Ala Gln Pro Ala Lys Lys Arg Leu Asn Phe Gly Gln Thr Gly
                165                 170                 175

Asp Thr Glu Ser Val Pro Asp Pro Gln Pro Ile Gly Glu Pro Pro Ala
            180                 185                 190

Ala Pro Ser Gly Val Gly Ser Leu Thr Met Ala Ser Gly Gly Gly Ala
        195                 200                 205

Pro Val Ala Asp Asn Asn Glu Gly Ala Asp Gly Val Gly Ser Ser Ser
    210                 215                 220

Gly Asn Trp His Cys Asp Ser Gln Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Asn Ser Thr Ser Gly Gly Ser Ser Asn Asp Asn Ala
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Asp Asn Asn Gly Val Lys Thr Ile Ala Asn Asn
                325                 330                 335

Leu Thr Ser Thr Val Gln Val Phe Thr Asp Ser Asp Tyr Gln Leu Pro
            340                 345                 350

Tyr Val Leu Gly Ser Ala His Glu Gly Cys Leu Pro Pro Phe Pro Ala
            355                 360                 365

Asp Val Phe Met Ile Pro Gln Tyr Gly Tyr Leu Thr Leu Asn Asp Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Glu Phe
                405                 410                 415

Glu Asn Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Lys
            435                 440                 445

Thr Ile Asn Gly Ser Gly Gln Asn Gln Gln Thr Leu Lys Phe Ser Val
            450                 455                 460

Ala Gly Pro Ser Asn Met Ala Val Gln Gly Arg Asn Tyr Ile Pro Gly
465                 470                 475                 480

Pro Ser Tyr Arg Gln Gln Arg Val Ser Thr Thr Val Thr Gln Asn Asn
                485                 490                 495

Asn Ser Glu Phe Ala Trp Pro Gly Ala Ser Ser Trp Ala Leu Asn Gly
            500                 505                 510

Arg Asn Ser Leu Met Asn Pro Gly Pro Ala Met Ala Ser His Lys Glu
            515                 520                 525

Gly Glu Asp Arg Phe Phe Pro Leu Ser Gly Ser Leu Ile Phe Gly Lys
530                 535                 540

Gln Gly Thr Gly Arg Asp Asn Val Asp Ala Asp Lys Val Met Ile Thr
545                 550                 555                 560

Asn Glu Glu Glu Ile Lys Thr Thr Asn Pro Val Ala Thr Glu Ser Tyr
                565                 570                 575

Gly Gln Val Ala Thr Asn His Gln Ser Ala Gln Ala Gln Ala Gln Thr
            580                 585                 590

Gly Trp Val Gln Asn Gln Gly Ile Leu Pro Gly Met Val Trp Gln Asp
            595                 600                 605

Arg Asp Val Tyr Leu Gln Gly Pro Ile Trp Ala Lys Ile Pro His Thr
610                 615                 620

Asp Gly Asn Phe His Pro Ser Pro Leu Met Gly Gly Phe Gly Met Lys
625                 630                 635                 640

His Pro Pro Pro Gln Ile Leu Ile Lys Asn Thr Pro Val Pro Ala Asp
                645                 650                 655

Pro Pro Thr Ala Phe Asn Lys Asp Lys Leu Asn Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Tyr Lys Ser Asn Asn Val Glu Phe Ala Val Asn Thr Glu Gly Val Tyr
705                 710                 715                 720

Ser Glu Pro Arg Pro Ile Gly Thr Arg Tyr Leu Thr Arg Asn Leu
                725                 730                 735